United States Patent
Ito et al.

(10) Patent No.: US 10,898,555 B2
(45) Date of Patent: Jan. 26, 2021

(54) CELLULAR IMMUNITY INDUCING VACCINE

(71) Applicants: JAPANESE FOUNDATION FOR CANCER RESEARCH, Tokyo (JP); THE JIKEI UNIVERSITY, Tokyo (JP)

(72) Inventors: Masaki Ito, Tokyo (JP); Kiyotaka Shiba, Tokyo (JP)

(73) Assignees: JAPANESE FOUNDATION FOR CANCER RESEARCH, Tokyo (JP); THE JIKEI UNIVERSITY, Tokyo (JP)

(*) Notice: Subject to any disclaimer, the term of this patent is extended or adjusted under 35 U.S.C. 154(b) by 567 days.

(21) Appl. No.: 14/901,384

(22) PCT Filed: Jun. 30, 2014

(86) PCT No.: PCT/JP2014/067355
§ 371 (c)(1),
(2) Date: Feb. 29, 2016

(87) PCT Pub. No.: WO2015/002134
PCT Pub. Date: Jan. 8, 2015

(65) Prior Publication Data
US 2016/0166665 A1    Jun. 16, 2016

(30) Foreign Application Priority Data
Jul. 2, 2013 (JP) .................................. 2013-138688

(51) Int. Cl.
*A61K 39/00* (2006.01)
*C07K 19/00* (2006.01)
*C07K 14/47* (2006.01)
*C07K 14/74* (2006.01)

(52) U.S. Cl.
CPC .... *A61K 39/0011* (2013.01); *A61K 39/00115* (2018.08); *A61K 39/00117* (2018.08); *A61K 39/001106* (2018.08); *A61K 39/001124* (2018.08); *A61K 39/001151* (2018.08); *A61K 39/001153* (2018.08); *A61K 39/001156* (2018.08); *A61K 39/001162* (2018.08); *A61K 39/001186* (2018.08); *A61K 39/001188* (2018.08); *A61K 39/001191* (2018.08); *A61K 39/001192* (2018.08); *C07K 14/4748* (2013.01); *C07K 14/70539* (2013.01); *A61K 2039/62* (2013.01); *A61K 2039/64* (2013.01); *C07K 19/00* (2013.01); *Y02A 50/30* (2018.01)

(58) Field of Classification Search
CPC ............ A61K 39/0011; A61K 2039/62; A61K 2039/64; C07K 14/4748; C07K 14/70539; C07K 19/00
See application file for complete search history.

(56) References Cited

U.S. PATENT DOCUMENTS

| | | | |
|---|---|---|---|
| 2004/0171803 A1 | 9/2004 | Shiba et al. | |
| 2005/0136402 A1* | 6/2005 | Wang ................. | C07K 14/4748 435/6.14 |
| 2006/0093617 A1* | 5/2006 | Buyse .................. | C07K 14/005 424/189.1 |
| 2006/0216305 A1* | 9/2006 | Lal ........................ | A61K 39/21 424/188.1 |
| 2008/0260760 A1* | 10/2008 | Alexander ......... | A61K 39/0011 424/185.1 |
| 2009/0162405 A1* | 6/2009 | Qian .................. | A61K 39/0011 424/277.1 |
| 2010/0297187 A1* | 11/2010 | Stoloff ................ | A61K 39/005 424/272.1 |
| 2011/0159022 A1* | 6/2011 | Kerzerho ........... | A61K 39/0011 424/185.1 |

FOREIGN PATENT DOCUMENTS

JP    2002-119286 A    4/2002

OTHER PUBLICATIONS

Krug et al. (Cancer Immunol. Immunother, 59:1467-1479 (Year: 2010).*

(Continued)

*Primary Examiner* — Hong Sang
(74) *Attorney, Agent, or Firm* — Birch, Stewart, Kolasch & Birch, LLP

(57) ABSTRACT

A novel vaccine that can induce sufficiently high cell-mediated immunity is disclosed. The vaccine of the present invention contains, as an effective component, a polypeptide comprising a tandem repeat structure in which an MHC class I epitope region derived from an antigen protein and a spacer sequence are linked to each other alternately and repeatedly at least three times, or a recombinant vector which comprises a polynucleotide encoding said polypeptide and is capable of expressing said polypeptide in vivo. The spacer sequence is, for example, a sequence generated as an amino acid sequence inevitably encoded by a single base sequence which is designed such that the MHC class I epitope region derived from the antigen protein, an MHC class II epitope region derived from the antigen protein, and at least one higher-order-structure-stabilizing region are encoded by different reading frames in said single base sequence.

12 Claims, 12 Drawing Sheets

Specification includes a Sequence Listing.

(56) References Cited

OTHER PUBLICATIONS

Hailemichael et al., "Persistent antigen at vaccination sites induces tumor-specific CD8+ T cell sequestration, dysfunction and deletion," Nature Medicine (Apr. 1, 2013), vol. 19, pp. 465-472 (Abstract).
Khazaie et al., "Current developments with peptide-based human tumor vaccines," Current Opinion in Oncology (Nov. 2009), vol. 21, No. 6, pp. 524-530 (Abstract).
Perez et al., "A New Era in Anticancer Peptide Vaccines," Cancer (2010), vol. 116, pp. 2071-2080.
Slingluff, Jr., M.D., "The Present and Future of Peptide Vaccines for Cancer: Single or Multiple, Long or Short, Alone or in Combination?" Cancer J. (Sep. 2011), vol. 17, No. 5, pp. 343-350.
Yamada et al., "Next-generation peptide vaccines for advanced cancer," Cancer Science (Jan. 2013), vol. 104, No. 1, pp. 15-21.
International Search Report, issued in PCT/JP2014/067355, dated Sep. 16, 2014.

\* cited by examiner

Fig. 1

1) Original peptide sequence

```
 1                            11
 L   E   S   I   I   N   F   E   K   L   T      (SEQ ID NO:1)
Leu Glu Ser Ile Ile Asn Phe Glu Lys Leu Thr 1                                                          17
 I   S   Q   A   V   H   A   A   H   A   E   I   N   E   A   G   R   (SEQ ID NO:2)
Ile Ser Gln Ala Val His Ala Ala His Ala Glu Ile Asn Glu Ala Gly Arg
```

2) Reverse translation (SEQ ID NO:1)　L E S I I N F E K L T　　　　I S Q A V H A A H A E I N E A G R (SEQ ID NO:2)

```
       1                              33        1                                              51
5' TTA GAA TCT ATT ATT AAT TTT GAA AAA TTA ACT 3'  5' ATT TCT CAA GCT GTT CAT GCT GCT CAT GCT GAA ATT AAT GAA GCT GGT CGT 3'
   TTG GAG TCC ATC ATC AAC TTC GAG AAG TTG ACC       ATC TCC CAG GCC GTC CAC GCC GCC CAC GCC GAG ATC AAC GAG GCC GGC CGC
   CTT     TCA ATA ATA         CTT         ACA       ATA TCA     GCA GTA GCA GCA     GCA     ATA         GCA GGA CGA
   CTC     TCG                 CTC         ACG           TCG     GCG GTG GCG GCG     GCG                 GCG GGG CGG
   CTA     AGT                 CTA                       AGT                                                         AGA
   CTG     AGC                 CTG                       AGC                                                         AGG
```

3) Combination of DNA sequences (A library in processor)

(6x2x6x3x3x2x2x2x2x5x4) = 248,832     (3x6x2x4x4x2x4x4x2x4x2x3x2x2x4x4x6) = 169,869,312

4) Embedding specific motif within microgene using CyberGene (In silico calculation)

```
(SEQ ID NO:3)    R E Y H Q L R E A Y R         F S G S S C S S C R D Q R G W P   (SEQ ID NO:81)
(SEQ ID NO:6)    S R V S S T S R S L P         F L R Q F M Q L M Q R S T R L A   (SEQ ID NO:4)
(SEQ ID NO:80)   L E S I I N F E K L T E       I S Q A V H A A H A E I N E A G R (SEQ ID NO:2)
(SEQ ID NO:82)   CTCGAGAGTATCATCAACTTCGAGAAGCTTACCGAG  ATTTCTCAGGCAGTTCATGCAGCTCATGCAGAGATCAACGAGGCTGGCCGC (SEQ ID NO:83)
                 GAGCTCTCATAGTAGTTGAAGCTCTTCGAATGGCTC  TAAAGAGTCCGTCAAGTACGTCGAGTACGTCTCTAGTTGCTCCGACCGGCG
```

5) Design of microgene (#2101)

```
  R E Y H Q L R E A Y R F L R Q F M Q L M Q R S T R L A     (SEQ ID NO:14)
  S R V S S T S R S L P I S Q A V H A A H A E I N E A G R   (SEQ ID NO:13)
  L E S I I N F E K L T D F S G S S C S S C R D Q R G W P   (SEQ ID NO:12)
  CTCGAGAGTATCATCAACTTCGAGAAGCTTACCGATTTCTCAGGCAGTTCATGCAGCTCATGCAGAGATCAACGAGGCTGGCCGC (SEQ ID NO:11)
```

6) MPR primers

```
2101S  46 bp  CTCGAGAGTATCATCAACTTCGAGAAGCTTACCGATTTCTCAGGCT     (SEQ ID NO:19)
2101AS 49 bp  GCGGCCAGCCTCGTTGATCTCTGCATGAGCTGCATGAACTGCCTGAGAT  (SEQ ID NO:20)
```

7) Head-to-tail polymerization of microgene by MPR

Microgene #2101 (85bp)

CTCGAGAGTATCATCAACTTCGAGAAGCTTACCGATTTCTCAGGCAGTTCATGCAGCTCATGCAGAGATCAACGAGGCTGGCCGC (SEQ ID NO:11)

↓

(SEQ ID NO:19) CTCGAGAGTATCATCAACTTCGAGAAGCTTACCGATTTCTCAGGCT
                                              TAGAGTCCGTCAAGTACGTCGAGTACGTCTCTAGTTGCTCCGACCGGCG (SEQ ID NO:20)

↓

CTCGAGAGTATCATCAACTTCGAGAAGCTTACCGATTTCTCAGGCAGTTCATGCAGCTCATGCAGAGATCAACGAGGCTGGCCGC (SEQ ID NO:11)
GAGCTCTCATAGTAGTTGAAGCTCTTCGAATGGCTAAAGAGTCCGTCAAGTACGTCGAGTACGTCTCTAGTTGCTCCGACCGGCG

↓

—[ Microgene ]—[ ]—[ ]—[ ]—[ ]—

↓ Perturbations at junctions
deletion, insertion, random frameshifting

8) Translation

9) Combinatorial polymers of three reading frames

Fig.2

F182A (SEQ ID NO:26)
pI/Mw: 6.30 / 21051.12   190aa

MRGSHHHHHGSVDWGTPEINEAGR
LESIINFEKLTDFSGSSCSSCRDQRGWP
SRVSSTSRSLPISQAVHAAHAEINEAGR
SRVSSTSRSLPISHAEINEAG
LESIINFEKLTDLRQFTCRDQRGWP
LESIINFEKLTDFSGSSCSSCRDQRGW
PQSIINFEKLTDFSGSSCSSCRDQRWLA
LEGGSGVN

F182A: ○○●▽□■□■□●(▽/▼)●▽●▽◇

F36A (SEQ ID NO:29)
pI/Mw: 11.00 / 12066.23   115aa

MRGSHHHHHGSVDGTPTRLAA
SRVSSTSRSLPISQAVHAAHAEINEAGR
SRVSSTSRSLPISQAVHAAHAEINEAGR
 RVSSTSRSLPISQAVHAAHAEINEAGR
LESIINGDLG

F36A: ○○■□■□■◇

F37B (SEQ ID NO:32)
pI/Mw: 11.24 / 20505.98   182aa

MRGSHHHHHH
 TDPSTVPAYRFLRQFMQLMQRSTRLAA
SRVSSTSRSLPISQAVHAAHAEINEAGR
SRVSSTSRSLPISQAVHAAHAEINEAGR
SRVSSTSRSLPISQAVHAAHAEINEAGR
LESIINFEKLTDFSGSSCSSCRDQRGWPP
REYHQLREAYRFLRQFMQLMQRSTRLA
GIWVN

F37B: ○○▽□■□■□■●▽▲▽◇

F182B (SEQ ID NO:27)
pI/Mw: 10.73 / 22832.37   202aa

MRGSHHHHHHTDPSTVPQRSTRLAA
SRVSSTSRSLPISQAVHAAHAEINEAGR
REYHQLREAYRFLRQFMQLMQRSTRLAA
REYHQLREAYRFLMQRSTRLA
SRVSSTSRSLPISGSSHAEINEAGR
SRVSSTSEKLTDFSSSSCSSCRDQRGW
PQSIINFEKLTDSGSSCSSCRDQRGWP
SRGDLGLINLTKFSKEFRPA

F182B: ○○□■▲▼▲□■◇▽◇

F36B (SEQ ID NO:30)
pI/Mw: 11.65 / 14469.57   117aa

MRGSHHHHHHTDPSTVPQRGWPP
REYHQLREAYRFLRQFMQLMQRSTRLAA
REYHQLREAYRFLRQFMQLMQRSTRLA
AEYHQLREAYRFLRQFMQLMQRSTRLA
ASRVSSTGIWVN

F36B: ○○▲▼▲▼▲▽◇

F37C (SEQ ID NO:33)
pI/Mw: 11.24 / 22060.96   186aa

MRGSHHHHHH
GIRRQWRYPLTDFSGSSCSSCRDQRGWPP
REYHQLREAYRFLRQFMQLMQRSTRLAA
REYHQLREAYRFLRQFMQLMQRSTRLAA
REYHQLREAYRFLRQFMQLMQRSTRLAA
SRVSSTSRSLPISQAVHAAHAEINEAGR
LESIINFEKLTDFSGSSCSSCRDQRGW
RGSGLIN

F37C: ○○▽▲▼▲▼▲▼□■●▽◇

F182C (SEQ ID NO:28)
pI/Mw: 11.11 / 23900.19   194aa

MRGSHHHHHGIRRQWRYPRDQRGWPP
REYHQLREAYRFLRQFMQLMQRSTRLA
LESIINFEKLTDFSGSSCSSCRDQRGWP
LESIINFEKLTDFSCRDQRGWP
REYHQLREAYRSQAVHMQRSTRLAA
REYHQLREAYRFLRQFMQLMQRSTRLA
AEYHQLREAYRFLRQFMQLMQRSTRA
GPRRGDLGVRLN

F182C: ○○▲▼●▽●▽▲◇▲▼▽◇

F36C (SEQ ID NO:31)
pI/Mw: 8.64 / 13844.24    120aa

MRGSHHHHHGIRRQWRYPNEAGR
LESIINFEKLTDFSGSSCSSCRDQRGWP
LESIINFEKLTDFSGSSCSSCRDQRGW
PQSIINFEKLTDFSGSSCSSCRDQRGWP
PREYHQRGSGLIN

F36C: ○○●▽●▽●▽◇

F138A (SEQ ID NO:34)
pI/Mw: 8.55 / 17962.83    158aa

MRGSHHHHHG
SVDWGTLSGSSCSSCRDQRGC
SRVSSTSRSLPISQAVHAAHAEINEAGR
REYHQLREAYRFLRQFMQLMQRSTRLA
AESIINFEKLTDFSGSSCSSCRDQRGWP
LESIINFEKLTDFSGSSCSSCRDQRGWPP
REYHQLREAYGDLG

F138A: ○○□■▲▼●▽●▽▲◇

G142A (SEQ ID NO:35)
pI/Mw: 8.84 / 26673.74   239aa

MRGSHHHHHH
 GSVDWGTPISQAVHAAHAEINEAG
LESIINFEKLTDFSGSSCSSCRDQRGWP
SKVLSISKNSPISQAVHAAHAEINEAGR
LESIINFEKLTDFSGSSCSSCRDQRGWPP
RKYYQFRKTHRFLRQFMQLMQRSTRLAA
SKVLSISKNSPISQAVHAAHAEINEAGR
LESIINFEKLTDFSGSSCSSCRDQRGWP
LESIINFEKLTDFSGSSCSSCRDQRGWP
GIWVN

G142A: ○○■●▽◆■●▽□▼□■●▽●▽◇

G142C (SEQ ID NO:36)
pI/Mw: 11.39 / 28573.74   237aa

MRGSHHHHHG
IRRQWRYPDFSGSSCSSCRDQRWP
RKYYQFRKTHRFLRQFMQLMQRSTRLAA
LESIINFEKLTDFSGSSCSSCRDQRGWPP
RKYYQFRKTHRFLRQFMQLMQRSTRLAA
SKVLSISKNSPISQAVHAAHAEINEAGR
LESIINFEKLTDFSGSSCSSCRDQRGWPP
RKYYQFRKTHRFLRQFMQLMQRSTRLAA
RKYYQFRKTHRFLRQFMQLMQRSTRLAGDLG

G142C: ○○□▲▼●▽□▼□■●▽▲▼▲▽◇

● : LESIINFEKL     MHC class I (SEQ ID NO:1)
■ : ISQAVHAAHAEINEAGR   MHC class II (SEQ ID NO:2)
▲ : REYHQLREAYR    Alpha-helix (SEQ ID NO:3)
▼ : FLRQFMQLMQRSTRLA   Alpha-helix (SEQ ID NO:4)
◆ : SKVLSISKNSP    Beta-sheet (SEQ ID NO:5)
□ : SRVSSTSRSLP    (SEQ ID NO:6)
△ : RKYYQFRKTHR    (SEQ ID NO:7)
▽ : DFSGSSCSSCRDQRGWP  (SEQ ID NO:8)
○ : MRGSHHHHHH    His tag (SEQ ID NO:10)
(▽/▼) : TDLRQFTCRDQRGWP (SEQ ID NO:9)
◇ :               Random sequence

Fig.3

F58B (SEQ ID NO:37)
pI/Mw: 9.20 / 18250.23   163aa

MRGSHHHHHHTDPSTVPRGW
PQSIINFEKLTDFSGSSCSSCRDQRGWPP
REYHQLREAYRFLRQFMQLMQRSTRLAA
SRVSSTSRSLPISQAVHAAHAEINEAGR
LESIINFEKLTDFSGSSCSSCRDRGWP
RVSSTSRSLPISQAVHAAHAEINEAG
GDLG

F58B: ○●▽▲▼□■●▽□■

F58C (SEQ ID NO:38)
pI/Mw: 11.21 / 19389.83   166aa

MRGSHHHHHHGIRRQWRYPEAGR
RVSSTSRSLPISQAVHAAHAEINEAGR
LESIINFEKLTDFSGSSCSSCRDQRGWPP
REYHQLREAYRFLRQFMQLMQRSTRLAA
SRVSSTSRSLPISQAVHAAHAEINEAGR
EYHQLREAYRFLRQFMQLMQRSTRLA
GIWVN

F58C: ○□■●□▲▽■▲▽

F112A (SEQ ID NO:39)
pI/Mw: 11.16 / 23612.55   207aa

MRGSHHHHHH
GSVDGTREAYRFLRQFMQLMQRSTRLAA
REYHQLREAYRFLRQFMQLMQRSTRLAA
SRVSSTSRSLPISQAVHAAHAEINEAG
SRVSSTSRSLPISQAVHAAHAEINEAGR
SRVSSTSRSLPISQAVHAAHAEINEAGR
REYHQLREAYFLRQFMQLMQRSTRLA
LESIINFEKLTDFSGSCSSCRDQRGG
IWVN

F112A: ○▲▼▲□■□■▲▼●■

F112C (SEQ ID NO:40)
pI/Mw: 10.74 / 24985.26   211aa

MRGSHHHHHHG
IRRQWRYPRSLPISQGSSCSSCRDQRGWP
LESIINFEKLTDFSGSSCSSCRDQRGWP
REYHPLREAYRFLRQFMQLMQRSTRLA
REYHQLREAYRFLRQFMQLMQRSTRLAA
REYHQLREAYRFLRQFMQLMQRSTRLA
AESIINFEKLTYFSGSSCSSCRDQRGWP
SRVSSTSRSLPISQAVHAAHAEINEAGSGLIN

F112C: ○□●▽▲▽▲▽▲▽ □■

MT290 (SEQ ID NO:41)
pI/Mw: 10.09 / 12156.62   113aa

MRGSHHHHHGIRRRYPESLARAYGELASR
AESLARAYGELASRAESLARAYGELASRAE
SLARAYGELASRAESLARAYGELASRGKSC
KGVWRTCKPSGKSCKGGGSGLIN

MT297 (SEQ ID NO:42)
pI/Mw: 11.90/12251.95   104aa

MRGSHHHHHGSVDGTRTSKPNGKSYRVVW
RTSKPMGKSYRVVWRTSKPNGKSYRVVWRT
SKPNGKSYRVVWRTSKPNEKSYRVVWRTSK
PNRRVLQGRGIWVN

MT332 (SEQ ID NO:43)
pI/Mw: 11.69/16449.57   140aa

MRGSHHHHHGIRRRYPLQGRMENLQAERK
VLQGRMENLQAEKGSSGPYGESSGRERFFR
AVWRIFRQRKVLQGRMENLQAEKGSSGPYG
ESSGRERFFRAVWRIFRQRKGSSGPYGESS
GRERFFRAVWRIFRGSGLIN

●: LESIINFEKLT   MHC clas I (SEQ ID NO:1)
■: ISQAVHAAHAEINEAGR   MHC class II (SEQ ID NO:2)
▲: REYHQLREAYR   Alpha-helix (SEQ ID NO:3)
▼: FLRQFMQLMQRSTRLA   Alpha-helix (SEQ ID NO:4)
◆: SKVLSISKNSP   Beta-sheet (SEQ ID NO:5)
□: SRVSSTSRSLP   (SEQ ID NO:6)
△: RKYYQFRKTHR   (SEQ ID NO:7)
▽: DFSGSSCSSCRDQRGWP   (SEQ ID NO:8)
○: MRGSHHHHH   His tag (SEQ ID NO:10)
(▽/▼): TDLRQFTCRDQRGWP (SEQ ID NO:9)
◇: —   Random sequence

Fig.4 a

F37A (SEQ ID NO:44)
181aa, MW 20.3 KDa

MRGSHHHHHH
GSVDWGTRLPISQAVHAAHAEINEAGR
LESIINFEKLTDFSGSSCSSCRDQRGWP
LESIINFEKLTDFSGSSCSSCRDQRGWP
LESIINFEKLTDFSGSSCSSCRDQRGWP
PREYHQLREAYRFLRQFMQLMQRSTRLAA
SRVSSTSRSLPISQAVHAAHAEINEAGGDLG

F37A: ○○■●▽●▽●▽▲▽□■○ b

F182A: ○○▽■□■●(▽/▼)●▽●▽○
F182B: ○○□■▲▽▲□■□▽○
F182C: ○○▲▽●▽▲○▲▽▽○
F37A: ○○■●▽●▽●▽▲▽□■○
F37B: ○○▽■□■□■●▽▲▽○
F37C: ○○▽▲▽▲▽▲▽●▽○
F36A: ○○□■□■□■○
F36B: ○○▲▽▲▽▲▽○
F36C: ○○●▽●▽●▽○ c

F37A:    ○○■●▽●▽●▽▲▽□■◇ 181aa
F37AE2:  ○○■●▽●▽●▽▲▽□■◇ 183aa
MT819:   ○○■W▽●▽●▽▲▽□■◇ 184aa
MT820:   ○○■●▽W▽●▽▲▽□■◇ 184aa
MT821:   ○○■●▽●▽W▽▲▽□■◇ 184aa
MT822:   ○○■W▽W▽●▽▲▽□■◇ 185aa
MT823:   ○○■●▽W▽W▽▲▽□■◇ 185aa
MT824:   ○○■W▽●▽W▽▲▽□■◇ 185aa
MT825:   ○○■W▽W▽W▽▲▽□■◇ 186aa

W: LERMFPNAPYLT, WT1 MHC class I epitope (SEQ ID NO:65)

Fig.5

F37A (SEQ ID NO:44)
pI/Mw: 7.17/20313.51 181aa

MRGSHHHHHH
GSVDWGTRLPISQAVHAAHAEINEAGR
LESIINFEKLTDFSGSSCSSCRDQRGWP
LESIINFEKLTDFSGSSCSSCRDQRGWP
LESIINFEKLTDFSGSSCSSCRDQRGWPP
REYHQLREAYRFLRQFMQLMQRSTRLAA
SRVSSTSRSLPISQAVHAAHAEINEAG
GDLG

F37A: ○◇■▽●▽●▽▲▽□■◇

MT819 (SEQ ID NO:46)
pI/Mw: 8.3/20657.9 184aa

MRGSHHHHHH
GSVDWGTRLPISQAVHAAHAEINEAGR
LERMFPNAPYLTDFSGSSCSSCRDQRGWP
LESIINFEKLTDFSGSSCSSCRDQRGWP
LESIINFEKLTDFSGSSCSSCRDQRGWPP
REYHQLREAYRFLRQFMQLMQRSTRLAA
SRVSSTSRSLPISQAVHAAHAEINEAG
GSGLIN

MT819: ○◇■WV●▽●▽▲▽□■◇

MT822 (SEQ ID NO:49)
pI/Mw: 8.64/20803.1 185aa

MRGSHHHHHH
GSVDWGTRLPISQAVHAAHAEINEAGR
LERMFPNAPYLTDFSGSSCSSCRDQRGWP
LERMFPNAPYLTDFSGSSCSSCRDQRGWP
LESIINFEKLTDFSGSSCSSCRDQRGWPP
REYHQLREAYRFLRQFMQLMQRSTRLAA
SRVSSTSRSLPISQAVHAAHAEINEAG
GSGLIN

MT822: ○◇■W▽W▽●▽▲▽□■◇

F37AE2 (SEQ ID NO:45)
pI/Mw: 7.8/20517.8 183aa

MRGSHHHHHH
GSVDWGTRLPISQAVHAAHAEINEAGR
LESIINFEKLTDFSGSSCSSCRDQRGWP
LESIINFEKLTDFSGSSCSSCRDQRGWP
LESIINFEKLTDFSGSSCSSCRDQRGWPP
REYHQLREAYRFLRQFMQLMQRSTRLAA
SRVSSTSRSLPISQAVHAAHAEINEAG
GSGLIN

F37AE2: ○◇■▽●▽●▽▲▽□■◇

MT820 (SEQ ID NO:47)
pI/Mw: 8.3/20657.9 184aa

MRGSHHHHHH
GSVDWGTRLPISQAVHAAHAEINEAGR
LESIINFEKLTDFSGSSCSSCRDQRGWP
LERMFPNAPYLTDFSGSSCSSCRDQRGWP
LESIINFEKLTDFSGSSCSSCRDQRGWPP
REYHQLREAYRFLRQFMQLMQRSTRLAA
SRVSSTSRSLPISQAVHAAHAEINEAG
GSGLIN

MT820: ○◇■●▽W▽●▽▲▽□■◇

MT823 (SEQ ID NO:50)
pI/Mw: 8.64/20803.1 185aa

MRGSHHHHHH
GSVDWGTRLPISQAVHAAHAEINEAGR
LESIINFEKLTDFSGSSCSSCRDQRGWP
LERMFPNAPYLTDFSGSSCSSCRDQRGWP
LERMFPNAPYLTDFSGSSCSSCRDQRGWPP
REYHQLREAYRFLRQFMQLMQRSTRLAA
SRVSSTSRSLPISQAVHAAHAEINEAG
GSGLIN

MT823: ○◇■●▽W▽W▽▲▽□■◇

MT825 (SEQ ID NO:52)
pI/Mw: 8.9/20948.3 186aa

MRGSHHHHHH
GSVDWGTRLPISQAVHAAHAEINEAGR
LERMFPNAPYLTDFSGSSCSSCRDQRGWP
LERMFPNAPYLTDFSGSSCSSCRDQRGWP
LERMFPNAPYLTDFSGSSCSSCRDQRGWPP
REYHQLREAYRFLRQFMQLMQRSTRLAA
SRVSSTSRSLPISQAVHAAHAEINEAG
GSGLIN

MT825: ○◇■W▽W▽W▽▲▽□■◇

MT821 (SEQ ID NO:48)
pI/Mw: 8.3/20657.9 184aa

MRGSHHHHHH
GSVDWGTRLPISQAVHAAHAEINEAGR
LESIINFEKLTDFSGSSCSSCRDQRGWP
LESIINFEKLTDFSGSSCSSCRDQRGWP
LERMFPNAPYLTDFSGSSCSSCRDQRGWPP
REYHQLREAYRFLRQFMQLMQRSTRLAA
SRVSSTSRSLPISQAVHAAHAEINEAG
GSGLIN

MT821: ○◇■●▽●▽W▽▲▽□■◇

MT824 (SEQ ID NO:51)
pI/Mw: 8.64/20803.1 185aa

MRGSHHHHHH
GSVDWGTRLPISQAVHAAHAEINEAGR
LERMFPNAPYLTDFSGSSCSSCRDQRGWP
LESIINFEKLTDFSGSSCSSCRDQRGWP
LERMFPNAPYLTDFSGSSCSSCRDQRGWPP
REYHQLREAYRFLRQFMQLMQRSTRLAA
SRVSSTSRSLPISQAVHAAHAEINEAG
GSGLIN

MT824: ○◇■W▽●▽W▽▲▽□■◇

W : LERMFPNAPYLT, WT1 MHC class I epitope (SEQ ID NO:65)
● : LeSIINFEKLt       MHC clas I (SEQ ID NO:1)
■ : ISQAVHAAHAEINEAGR  MHC class II (SEQ ID NO:2)
▲ : REYHQLREAYR       Alpha-helix (SEQ ID NO:3)
▼ : FLRQFMQLMQRSTRLA  Alpha-helix (SEQ ID NO:4)
◆ : SKVLSISKNSP       Beta-sheet (SEQ ID NO:5)
□ : SRVSSTSRSLP       (SEQ ID NO:6)
△ : RKYYQFRKTHR       (SEQ ID NO:7)
▽ : DFSGSSCSSCRDQRGWP (SEQ ID NO:8)
○ : MRGSHHHHHH        His tag (SEQ ID NO:10)
(▽/▼) : TDLRQFTCRDQRGWP (SEQ ID NO:9)
◇ :                   Random sequence

Fig.6

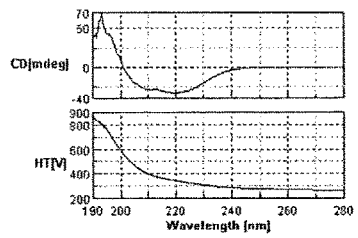
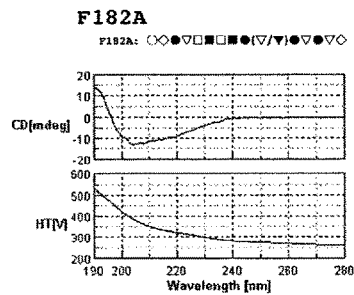 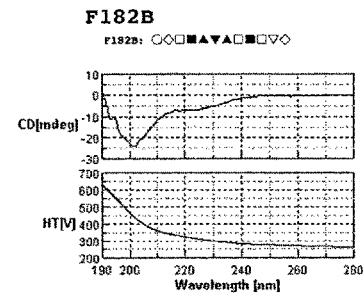 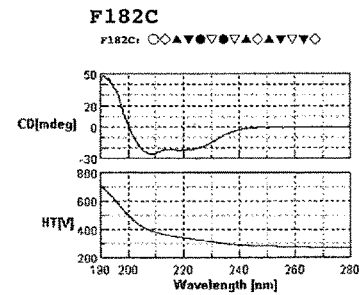
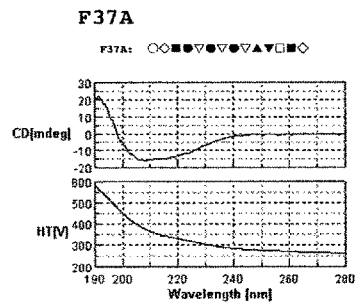 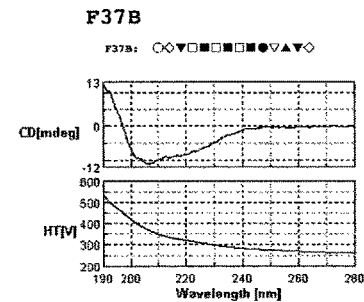 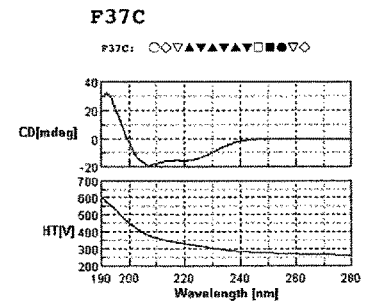
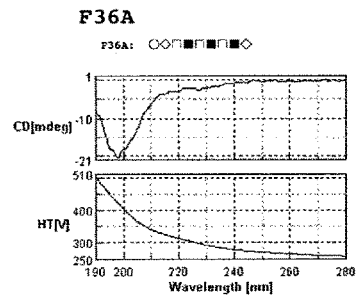 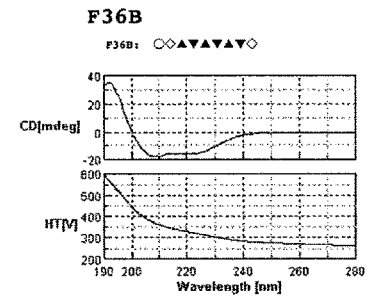 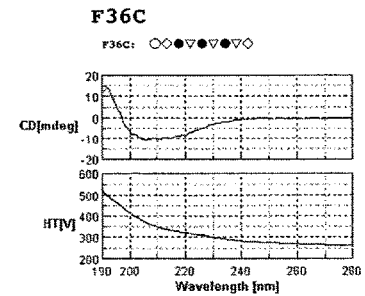
Fig.7

SEQUENCE LISTING

<160> NUMBER OF SEQ ID NOS: 83

<210> SEQ ID NO 1
<211> LENGTH: 11
<212> TYPE: PRT
<213> ORGANISM: Homo sapiens

<400> SEQUENCE: 1

Leu Glu Ser Ile Ile Asn Phe Glu Lys Leu Thr
1               5                   10

<210> SEQ ID NO 2
<211> LENGTH: 17
<212> TYPE: PRT
<213> ORGANISM: Homo sapiens

<400> SEQUENCE: 2

Ile Ser Gln Ala Val His Ala Ala His Ala Glu Ile Asn Glu Ala Gly
1               5                   10                  15

Arg

<210> SEQ ID NO 3
<211> LENGTH: 11
<212> TYPE: PRT
<213> ORGANISM: Artificial
<220> FEATURE:
<223> OTHER INFORMATION: alpha helix

<400> SEQUENCE: 3

Arg Glu Tyr His Gln Leu Arg Glu Ala Tyr Arg
1               5                   10

<210> SEQ ID NO 4
<211> LENGTH: 16
<212> TYPE: PRT
<213> ORGANISM: Artificial
<220> FEATURE:
<223> OTHER INFORMATION: alpha helix

<400> SEQUENCE: 4

Phe Leu Arg Gln Phe Met Gln Leu Met Gln Arg Ser Thr Arg Leu Ala
1               5                   10                  15

<210> SEQ ID NO 5
<211> LENGTH: 11
<212> TYPE: PRT
<213> ORGANISM: Artificial
<220> FEATURE:
<223> OTHER INFORMATION: beta sheet

<400> SEQUENCE: 5

Ser Lys Val Leu Ser Ile Ser Lys Asn Ser Pro
1               5                   10

<210> SEQ ID NO 6
<211> LENGTH: 11
<212> TYPE: PRT
<213> ORGANISM: Artificial
<220> FEATURE:
<223> OTHER INFORMATION: peptide sequence

<400> SEQUENCE: 6

Ser Arg Val Ser Ser Thr Ser Arg Ser Leu Pro
1               5                   10

```
<210> SEQ ID NO 7
<211> LENGTH: 11
<212> TYPE: PRT
<213> ORGANISM: Artificial
<220> FEATURE:
<223> OTHER INFORMATION: peptide sequence

<400> SEQUENCE: 7

Arg Lys Tyr Tyr Gln Phe Arg Lys Thr His Arg
1               5                   10

<210> SEQ ID NO 8
<211> LENGTH: 17
<212> TYPE: PRT
<213> ORGANISM: Artificial
<220> FEATURE:
<223> OTHER INFORMATION: peptide sequence

<400> SEQUENCE: 8

Asp Phe Ser Gly Ser Ser Cys Ser Ser Cys Arg Asp Gln Arg Gly Trp
1               5                   10                  15

Pro

<210> SEQ ID NO 9
<211> LENGTH: 14
<212> TYPE: PRT
<213> ORGANISM: Artificial
<220> FEATURE:
<223> OTHER INFORMATION: peptide sequence

<400> SEQUENCE: 9

Asp Leu Arg Gln Phe Thr Cys Arg Asp Gln Arg Gly Trp Pro
1               5                   10

<210> SEQ ID NO 10
<211> LENGTH: 10
<212> TYPE: PRT
<213> ORGANISM: Artificial
<220> FEATURE:
<223> OTHER INFORMATION: His tag

<400> SEQUENCE: 10

Met Arg Gly Ser His His His His His His
1               5                   10

<210> SEQ ID NO 11
<211> LENGTH: 85
<212> TYPE: DNA
<213> ORGANISM: Artificial
<220> FEATURE:
<223> OTHER INFORMATION: microgene #2101

<400> SEQUENCE: 11
ctcgagagta tcatcaactt cgagaagctt accgatttct caggcagttc atgcagctca      60
tgcagagatc aacgaggctg gccgc                                            85

<210> SEQ ID NO 12
<211> LENGTH: 28
<212> TYPE: PRT
<213> ORGANISM: Artificial
<220> FEATURE:
<223> OTHER INFORMATION: peptide sequence encoded in frame 1 of
      microgene #2101

<400> SEQUENCE: 12

Leu Glu Ser Ile Ile Asn Phe Glu Lys Leu Thr Asp Phe Ser Gly Ser
```

```
1               5                  10                  15
Ser Cys Ser Ser Cys Arg Asp Gln Arg Gly Trp Pro
            20                  25

<210> SEQ ID NO 13
<211> LENGTH: 28
<212> TYPE: PRT
<213> ORGANISM: Artificial
<220> FEATURE:
<223> OTHER INFORMATION: peptide sequence encoded in frame 2 of
      microgene #2101

<400> SEQUENCE: 13

Ser Arg Val Ser Ser Thr Ser Arg Ser Leu Pro Ile Ser Gln Ala Val
1               5                  10                  15

His Ala Ala His Ala Glu Ile Asn Glu Ala Gly Arg
            20                  25

<210> SEQ ID NO 14
<211> LENGTH: 27
<212> TYPE: PRT
<213> ORGANISM: Artificial
<220> FEATURE:
<223> OTHER INFORMATION: peptide sequence encoded in frame 3 of
      microgene #2101

<400> SEQUENCE: 14

Arg Glu Tyr His Gln Leu Arg Glu Ala Tyr Arg Phe Leu Arg Gln Phe
1               5                  10                  15

Met Gln Leu Met Gln Arg Ser Thr Arg Leu Ala
            20                  25

<210> SEQ ID NO 15
<211> LENGTH: 85
<212> TYPE: DNA
<213> ORGANISM: Artificial
<220> FEATURE:
<223> OTHER INFORMATION: microgene #6101

<400> SEQUENCE: 15
ctcgaaagta ttatcaattt cgaaaaactc accgatttct caggcagttc atgcagctca      60
tgcagagatc aacgaggctg ccgc                                             85

<210> SEQ ID NO 16
<211> LENGTH: 28
<212> TYPE: PRT
<213> ORGANISM: Artificial
<220> FEATURE:
<223> OTHER INFORMATION: peptide sequence encoded in frame 1 of
      microgene #6101

<400> SEQUENCE: 16

Leu Glu Ser Ile Ile Asn Phe Glu Lys Leu Thr Asp Phe Ser Gly Ser
1               5                  10                  15

Ser Cys Ser Ser Cys Arg Asp Gln Arg Gly Trp Pro
            20                  25

<210> SEQ ID NO 17
<211> LENGTH: 28
<212> TYPE: PRT
<213> ORGANISM: Artificial
<220> FEATURE:
<223> OTHER INFORMATION: peptide sequence encoded in frame 2 of
      microgene #6101
```

```
<400> SEQUENCE: 17

Ser Lys Val Leu Ser Ile Ser Lys Asn Ser Pro Ile Ser Gln Ala Val
1               5                   10                  15

His Ala Ala His Ala Glu Ile Asn Glu Ala Gly Arg
            20                  25

<210> SEQ ID NO 18
<211> LENGTH: 27
<212> TYPE: PRT
<213> ORGANISM: Artificial
<220> FEATURE:
<223> OTHER INFORMATION: peptide sequence encoded in frame 3 of
      microgene #6101

<400> SEQUENCE: 18

Arg Lys Tyr Tyr Gln Phe Arg Lys Thr His Arg Phe Leu Arg Gln Phe
1               5                   10                  15

Met Gln Leu Met Gln Arg Ser Thr Arg Leu Ala
            20                  25

<210> SEQ ID NO 19
<211> LENGTH: 46
<212> TYPE: DNA
<213> ORGANISM: Artificial
<220> FEATURE:
<223> OTHER INFORMATION: MPR primer 2101-S

<400> SEQUENCE: 19
ctcgagagta tcatcaactt cgagaagctt accgatttct caggct          46

<210> SEQ ID NO 20
<211> LENGTH: 49
<212> TYPE: DNA
<213> ORGANISM: Artificial
<220> FEATURE:
<223> OTHER INFORMATION: MPR primer 2101-AS, 6101-AS

<400> SEQUENCE: 20
gcggccagcc tcgttgatct ctgcatgagc tgcatgaact gcctgagat          49

<210> SEQ ID NO 21
<211> LENGTH: 46
<212> TYPE: DNA
<213> ORGANISM: Artificial
<220> FEATURE:
<223> OTHER INFORMATION: MPR primer 6101-S

<400> SEQUENCE: 21
ctcgaaagta ttatcaattt cgaaaaactc accgatttct caggct          46

<210> SEQ ID NO 22
<211> LENGTH: 28
<212> TYPE: PRT
<213> ORGANISM: Artificial
<220> FEATURE:
<223> OTHER INFORMATION: tandem repeat unit

<400> SEQUENCE: 22

Leu Glu Ser Ile Ile Asn Phe Glu Lys Leu Thr Asp Phe Ser Gly Ser
1               5                   10                  15

Ser Cys Ser Ser Cys Arg Asp Gln Arg Gly Trp Pro
            20                  25

<210> SEQ ID NO 23
```

<211> LENGTH: 517
<212> TYPE: PRT
<213> ORGANISM: Homo sapiens

<400> SEQUENCE: 23

```
Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
                100                 105                 110

Ala Ser Ala Tyr Gly Ser Leu Gly Gly Pro Ala Pro Pro Pro Ala Pro
            115                 120                 125

Pro Pro Pro Pro Pro Pro Pro His Ser Phe Ile Lys Gln Glu Pro
        130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
```

-continued

```
            385                 390                 395                 400
Arg Tyr Phe Lys Leu Ser His Leu Gln Met His Ser Arg Lys His Thr
                405                 410                 415
Gly Glu Lys Pro Tyr Gln Cys Asp Phe Lys Asp Cys Glu Arg Arg Phe
            420                 425                 430
Ser Arg Ser Asp Gln Leu Lys Arg His Gln Arg Arg His Thr Gly Val
            435                 440                 445
Lys Pro Phe Gln Cys Lys Thr Cys Gln Arg Lys Phe Ser Arg Ser Asp
    450                 455                 460
His Leu Lys Thr His Thr Arg Thr His Thr Gly Lys Thr Ser Glu Lys
465                 470                 475                 480
Pro Phe Ser Cys Arg Trp Pro Ser Cys Gln Lys Lys Phe Ala Arg Ser
                485                 490                 495
Asp Glu Leu Val Arg His His Asn Met His Gln Arg Asn Met Thr Lys
            500                 505                 510
Leu Gln Leu Ala Leu
            515

<210> SEQ ID NO 24
<211> LENGTH: 386
<212> TYPE: PRT
<213> ORGANISM: Gallus gallus

<400> SEQUENCE: 24

Met Gly Ser Ile Gly Ala Ala Ser Met Glu Phe Cys Phe Asp Val Phe
1               5                   10                  15
Lys Glu Leu Lys Val His His Ala Asn Glu Asn Ile Phe Tyr Cys Pro
            20                  25                  30
Ile Ala Ile Met Ser Ala Leu Ala Met Val Tyr Leu Gly Ala Lys Asp
        35                  40                  45
Ser Thr Arg Thr Gln Ile Asn Lys Val Val Arg Phe Asp Lys Leu Pro
    50                  55                  60
Gly Phe Gly Asp Ser Ile Glu Ala Gln Cys Gly Thr Ser Val Asn Val
65                  70                  75                  80
His Ser Ser Leu Arg Asp Ile Leu Asn Gln Ile Thr Lys Pro Asn Asp
                85                  90                  95
Val Tyr Ser Phe Ser Leu Ala Ser Arg Leu Tyr Ala Glu Glu Arg Tyr
            100                 105                 110
Pro Ile Leu Pro Glu Tyr Leu Gln Cys Val Lys Glu Leu Tyr Arg Gly
        115                 120                 125
Gly Leu Glu Pro Ile Asn Phe Gln Thr Ala Ala Asp Gln Ala Arg Glu
    130                 135                 140
Leu Ile Asn Ser Trp Val Glu Ser Gln Thr Asn Gly Ile Ile Arg Asn
145                 150                 155                 160
Val Leu Gln Pro Ser Ser Val Asp Ser Gln Thr Ala Met Val Leu Val
                165                 170                 175
Asn Ala Ile Val Phe Lys Gly Leu Trp Glu Lys Thr Phe Lys Asp Glu
            180                 185                 190
Asp Thr Gln Ala Met Pro Phe Arg Val Thr Glu Gln Glu Ser Lys Pro
        195                 200                 205
Val Gln Met Met Tyr Gln Ile Gly Leu Phe Arg Val Ala Ser Met Ala
    210                 215                 220
Ser Glu Lys Met Lys Ile Leu Glu Leu Pro Phe Ala Ser Gly Thr Met
225                 230                 235                 240
```

```
Ser Met Leu Val Leu Leu Pro Asp Glu Val Ser Gly Leu Glu Gln Leu
            245                 250                 255

Glu Ser Ile Ile Asn Phe Glu Lys Leu Thr Glu Trp Thr Ser Ser Asn
        260                 265                 270

Val Met Glu Glu Arg Lys Ile Lys Val Tyr Leu Pro Arg Met Lys Met
    275                 280                 285

Glu Glu Lys Tyr Asn Leu Thr Ser Val Leu Met Ala Met Gly Ile Thr
290                 295                 300

Asp Val Phe Ser Ser Ala Asn Leu Ser Gly Ile Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 25
<211> LENGTH: 29
<212> TYPE: PRT
<213> ORGANISM: Artificial
<220> FEATURE:
<223> OTHER INFORMATION: tandem repeat unit with a substitution of WT1
      MHC class I epitope for OVA MHC class I epitope

<400> SEQUENCE: 25

Leu Glu Arg Met Phe Pro Asn Ala Pro Tyr Leu Thr Asp Phe Ser Gly
1               5                   10                  15

Ser Ser Cys Ser Ser Cys Arg Asp Gln Arg Gly Trp Pro
            20                  25

<210> SEQ ID NO 26
<211> LENGTH: 190
<212> TYPE: PRT
<213> ORGANISM: Artificial
<220> FEATURE:
<223> OTHER INFORMATION: F182A

<400> SEQUENCE: 26

Met Arg Gly Ser His His His His His His Gly Ser Val Asp Trp Gly
1               5                   10                  15

Thr Pro Glu Ile Asn Glu Ala Gly Arg Leu Glu Ser Ile Ile Asn Phe
            20                  25                  30

Glu Lys Leu Thr Asp Phe Ser Gly Ser Ser Cys Ser Ser Cys Arg Asp
        35                  40                  45

Gln Arg Gly Trp Pro Ser Arg Val Ser Ser Thr Ser Arg Ser Leu Pro
    50                  55                  60

Ile Ser Gln Ala Val His Ala Ala His Ala Glu Ile Asn Glu Ala Gly
65                  70                  75                  80

Arg Ser Arg Val Ser Ser Thr Ser Arg Ser Leu Pro Ile Ser His Ala
                85                  90                  95

Glu Ile Asn Glu Ala Gly Leu Glu Ser Ile Ile Asn Phe Glu Lys Leu
            100                 105                 110

Thr Asp Leu Arg Gln Phe Thr Cys Arg Asp Gln Arg Gly Trp Pro Leu
```

```
                    115                 120                 125
Glu Ser Ile Ile Asn Phe Glu Lys Leu Thr Asp Phe Ser Gly Ser Ser
        130                 135                 140

Cys Ser Ser Cys Arg Asp Gln Arg Gly Trp Pro Gln Ser Ile Ile Asn
145                 150                 155                 160

Phe Glu Lys Leu Thr Asp Phe Ser Gly Ser Ser Cys Ser Ser Cys Arg
                165                 170                 175

Asp Gln Arg Trp Leu Ala Leu Glu Gly Gly Ser Gly Val Asn
            180                 185                 190
```

<210> SEQ ID NO 27
<211> LENGTH: 202
<212> TYPE: PRT
<213> ORGANISM: Artificial
<220> FEATURE:
<223> OTHER INFORMATION: F182B

<400> SEQUENCE: 27

```
Met Arg Gly Ser His His His His His His Thr Asp Pro Ser Thr Val
1               5                   10                  15

Pro Gln Arg Ser Thr Arg Leu Ala Ala Ser Arg Val Ser Ser Thr Ser
            20                  25                  30

Arg Ser Leu Pro Ile Ser Gln Ala Val His Ala Ala His Ala Glu Ile
        35                  40                  45

Asn Glu Ala Gly Pro Arg Glu Tyr His Gln Leu Arg Glu Ala Tyr Arg
    50                  55                  60

Phe Leu Arg Gln Phe Met Gln Leu Met Gln Arg Ser Thr Arg Leu Ala
65                  70                  75                  80

Ala Arg Glu Tyr His Gln Leu Arg Glu Ala Tyr Arg Phe Leu Met Gln
                85                  90                  95

Arg Ser Thr Arg Leu Ala Ser Arg Val Ser Ser Thr Ser Arg Ser Leu
                100                 105                 110

Pro Ile Ser Gly Ser Ser His Ala Glu Ile Asn Glu Ala Gly Arg Ser
            115                 120                 125

Arg Val Ser Ser Thr Ser Glu Lys Leu Thr Asp Phe Ser Ser Ser Ser
        130                 135                 140

Cys Ser Ser Cys Arg Asp Gln Arg Gly Trp Pro Gln Ser Ile Ile Asn
145                 150                 155                 160

Phe Glu Lys Leu Thr Asp Ser Ser Gly Ser Ser Cys Ser Ser Cys Arg
                165                 170                 175

Asp Gln Arg Gly Trp Pro Ser Arg Gly Asp Leu Gly Leu Ile Asn Leu
            180                 185                 190

Thr Lys Phe Ser Lys Glu Phe Arg Pro Ala
                195                 200
```

<210> SEQ ID NO 28
<211> LENGTH: 194
<212> TYPE: PRT
<213> ORGANISM: Artificial
<220> FEATURE:
<223> OTHER INFORMATION: F182C

<400> SEQUENCE: 28

```
Met Arg Gly Ser His His His His His His Gly Ile Arg Arg Gln Trp
1               5                   10                  15

Arg Tyr Pro Arg Asp Gln Arg Gly Trp Pro Pro Arg Glu Tyr His Gln
            20                  25                  30
```

```
Leu Arg Glu Ala Tyr Arg Phe Leu Arg Gln Phe Met Gln Leu Met Gln
            35                  40                  45

Arg Ser Thr Arg Leu Ala Leu Glu Ser Ile Ile Asn Phe Glu Lys Leu
 50                  55                  60

Thr Asp Phe Ser Gly Ser Ser Cys Ser Cys Arg Asp Gln Arg Gly
 65                  70                  75                  80

Trp Pro Leu Glu Ser Ile Ile Asn Phe Glu Lys Leu Thr Asp Phe Ser
                    85                  90                  95

Cys Arg Asp Gln Arg Gly Trp Pro Arg Glu Tyr His Gln Leu Arg Glu
                100                 105                 110

Ala Tyr Arg Ser Gln Ala Val His Met Gln Arg Ser Thr Arg Leu Ala
            115                 120                 125

Ala Arg Glu Tyr His Gln Leu Arg Glu Ala Tyr Arg Phe Leu Arg Gln
130                 135                 140

Phe Met Gln Leu Met Gln Arg Ser Thr Arg Leu Ala Ala Glu Tyr His
145                 150                 155                 160

Gln Leu Arg Glu Ala Tyr Arg Phe Leu Arg Gln Phe Met Gln Leu Met
                165                 170                 175

Gln Arg Ser Thr Arg Ala Gly Pro Arg Arg Gly Asp Leu Gly Val Lys
                180                 185                 190

Leu Asn

<210> SEQ ID NO 29
<211> LENGTH: 115
<212> TYPE: PRT
<213> ORGANISM: Artificial
<220> FEATURE:
<223> OTHER INFORMATION: F36A

<400> SEQUENCE: 29

Met Arg Gly Ser His His His His His His Gly Ser Val Asp Gly Thr
 1               5                  10                  15

Pro Thr Arg Leu Ala Ala Ser Arg Val Ser Ser Thr Ser Arg Ser Leu
                20                  25                  30

Pro Ile Ser Gln Ala Val His Ala Ala His Ala Glu Ile Asn Glu Ala
             35                  40                  45

Gly Arg Ser Arg Val Ser Ser Thr Ser Arg Ser Leu Pro Ile Ser Gln
 50                  55                  60

Ala Val His Ala Ala His Ala Glu Ile Asn Glu Ala Gly Arg Arg Val
 65                  70                  75                  80

Ser Ser Thr Ser Arg Ser Leu Pro Ile Ser Gln Ala Val His Ala Ala
                85                  90                  95

His Ala Glu Ile Asn Glu Ala Gly Arg Leu Glu Ser Ile Ile Asn Gly
                100                 105                 110

Asp Leu Gly
        115

<210> SEQ ID NO 30
<211> LENGTH: 117
<212> TYPE: PRT
<213> ORGANISM: Artificial
<220> FEATURE:
<223> OTHER INFORMATION: F36B

<400> SEQUENCE: 30

Met Arg Gly Ser His His His His His His Thr Asp Pro Ser Thr Val
 1               5                  10                  15
```

```
Pro Gln Arg Gly Trp Pro Pro Glu Tyr His Gln Leu Arg Glu Ala
            20                  25                  30

Tyr Arg Phe Leu Arg Gln Phe Met Gln Leu Met Gln Ser Thr Arg
            35                  40                  45

Leu Ala Ala Arg Glu Tyr His Gln Leu Arg Glu Ala Tyr Arg Phe Leu
 50                      55                  60

Arg Gln Phe Met Gln Leu Met Gln Arg Ser Thr Arg Leu Ala Ala Glu
65                  70                  75                  80

Tyr His Gln Leu Arg Glu Ala Tyr Arg Phe Leu Arg Gln Phe Met Gln
                85                  90                  95

Leu Met Gln Arg Ser Thr Arg Leu Ala Ala Ser Arg Val Ser Ser Thr
            100                 105                 110

Gly Ile Trp Val Asn
        115

<210> SEQ ID NO 31
<211> LENGTH: 120
<212> TYPE: PRT
<213> ORGANISM: Artificial
<220> FEATURE:
<223> OTHER INFORMATION: F36C

<400> SEQUENCE: 31

Met Arg Gly Ser His His His His His Gly Ile Arg Arg Gln Trp
1               5                   10                  15

Arg Tyr Pro Asn Glu Ala Gly Arg Leu Glu Ser Ile Ile Asn Phe Glu
            20                  25                  30

Lys Leu Thr Asp Phe Ser Gly Ser Ser Cys Ser Ser Cys Arg Asp Gln
            35                  40                  45

Arg Gly Trp Pro Leu Glu Ser Ile Ile Asn Phe Glu Lys Leu Thr Asp
 50                      55                  60

Phe Ser Gly Ser Ser Cys Ser Cys Arg Asp Gln Arg Gly Trp Pro
65                  70                  75                  80

Gln Ser Ile Ile Asn Phe Glu Lys Leu Thr Asp Phe Ser Gly Ser Ser
                85                  90                  95

Cys Ser Ser Cys Arg Asp Gln Arg Gly Trp Pro Pro Arg Glu Tyr His
            100                 105                 110

Gln Arg Gly Ser Gly Leu Ile Asn
        115                 120

<210> SEQ ID NO 32
<211> LENGTH: 182
<212> TYPE: PRT
<213> ORGANISM: Artificial
<220> FEATURE:
<223> OTHER INFORMATION: F37B

<400> SEQUENCE: 32

Met Arg Gly Ser His His His His His Thr Asp Pro Ser Thr Val
1               5                   10                  15

Pro Ala Tyr Arg Phe Leu Arg Gln Phe Met Gln Leu Met Gln Arg Ser
            20                  25                  30

Thr Arg Leu Ala Ala Ser Arg Val Ser Ser Thr Ser Arg Ser Leu Pro
            35                  40                  45

Ile Ser Gln Ala Val His Ala Ala His Ala Glu Ile Asn Glu Ala Gly
 50                      55                  60

Arg Ser Arg Val Ser Ser Thr Arg Ser Leu Pro Ile Ser Gln Ala
65                  70                  75                  80
```

```
Val His Ala Ala His Ala Glu Ile Asn Glu Ala Gly Arg Ser Arg Val
                85                  90                  95

Ser Ser Thr Ser Arg Ser Leu Pro Ile Ser Gln Ala Val His Ala Ala
            100                 105                 110

His Ala Glu Ile Asn Glu Ala Gly Arg Leu Glu Ser Ile Ile Asn Phe
        115                 120                 125

Glu Lys Leu Thr Asp Phe Ser Gly Ser Ser Cys Ser Ser Cys Arg Asp
130                 135                 140

Gln Arg Gly Trp Pro Pro Arg Glu Tyr His Gln Leu Arg Glu Ala Tyr
145                 150                 155                 160

Arg Phe Leu Arg Gln Phe Met Gln Leu Met Gln Arg Ser Thr Arg Leu
                165                 170                 175

Ala Gly Ile Trp Val Asn
            180
```

<210> SEQ ID NO 33
<211> LENGTH: 185
<212> TYPE: PRT
<213> ORGANISM: Artificial
<220> FEATURE:
<223> OTHER INFORMATION: F37C

<400> SEQUENCE: 33

```
Met Arg Gly Ser His His His His His Gly Ile Arg Arg Gln Trp
1               5                   10                  15

Arg Tyr Pro Leu Thr Asp Phe Ser Gly Ser Ser Cys Ser Ser Cys Arg
                20                  25                  30

Asp Gln Arg Gly Trp Pro Pro Arg Glu Tyr His Gln Leu Arg Glu Ala
            35                  40                  45

Tyr Arg Phe Leu Arg Gln Phe Met Gln Leu Met Gln Arg Ser Thr Arg
50                  55                  60

Leu Ala Ala Arg Glu Tyr His Gln Leu Arg Glu Ala Tyr Arg Phe Leu
65                  70                  75                  80

Arg Gln Phe Met Gln Leu Met Gln Arg Ser Thr Arg Leu Ala Ala Arg
                85                  90                  95

Glu Tyr His Gln Leu Arg Glu Ala Tyr Arg Phe Leu Arg Gln Phe Met
            100                 105                 110

Gln Leu Met Gln Arg Ser Thr Arg Leu Ala Ala Ser Arg Val Ser Ser
        115                 120                 125

Thr Ser Arg Ser Leu Pro Ile Ser Gln Ala Val His Ala Ala His Ala
130                 135                 140

Glu Ile Asn Glu Ala Gly Arg Leu Glu Ser Ile Ile Asn Phe Glu Lys
145                 150                 155                 160

Leu Thr Asp Phe Ser Gly Ser Ser Cys Ser Ser Cys Arg Asp Gln Arg
                165                 170                 175

Gly Trp Arg Gly Ser Gly Leu Ile Asn
            180                 185
```

<210> SEQ ID NO 34
<211> LENGTH: 158
<212> TYPE: PRT
<213> ORGANISM: Artificial
<220> FEATURE:
<223> OTHER INFORMATION: F138A

<400> SEQUENCE: 34

```
Met Arg Gly Ser His His His His His Gly Ser Val Asp Trp Gly
```

```
1               5                   10                  15
Thr Leu Ser Gly Ser Ser Cys Ser Ser Cys Arg Asp Gln Arg Gly Cys
            20                  25                  30

Ser Arg Val Ser Ser Thr Ser Arg Ser Leu Pro Ile Ser Gln Ala Val
            35                  40                  45

His Ala His Ala Glu Ile Asn Glu Ala Gly Arg Arg Glu Tyr His
    50                  55                  60

Gln Leu Arg Glu Ala Tyr Arg Phe Leu Arg Gln Phe Met Gln Leu Met
65                  70                  75                  80

Gln Arg Ser Thr Arg Leu Ala Ala Glu Ser Ile Ile Asn Phe Glu Lys
                85                  90                  95

Leu Thr Asp Phe Ser Gly Ser Ser Cys Ser Ser Cys Arg Asp Gln Arg
                100                 105                 110

Gly Trp Pro Leu Glu Ser Ile Ile Asn Phe Glu Lys Leu Thr Asp Phe
            115                 120                 125

Ser Gly Ser Ser Cys Ser Ser Cys Arg Asp Gln Arg Gly Trp Pro Pro
            130                 135                 140

Arg Glu Tyr His Gln Leu Arg Glu Ala Tyr Gly Asp Leu Gly
145                 150                 155
```

<210> SEQ ID NO 35
<211> LENGTH: 239
<212> TYPE: PRT
<213> ORGANISM: Artificial
<220> FEATURE:
<223> OTHER INFORMATION: G142A

<400> SEQUENCE: 35

```
Met Arg Gly Ser His His His His His His Gly Ser Val Asp Trp Gly
1               5                   10                  15

Thr Gly Thr Pro Ile Ser Gln Ala Val His Ala Ala His Ala Glu Ile
            20                  25                  30

Asn Glu Ala Gly Leu Glu Ser Ile Ile Asn Phe Glu Lys Leu Thr Asp
            35                  40                  45

Phe Ser Gly Ser Ser Cys Ser Ser Cys Arg Asp Gln Arg Gly Trp Pro
            50                  55                  60

Arg Ser Lys Val Leu Ser Ile Ser Lys Asn Ser Pro Ile Ser Gln Ala
65                  70                  75                  80

Val His Ala Ala His Ala Glu Ile Asn Glu Ala Gly Arg Leu Glu Ser
                85                  90                  95

Ile Ile Asn Phe Glu Lys Leu Thr Asp Phe Ser Gly Ser Ser Cys Ser
                100                 105                 110

Ser Cys Arg Asp Gln Arg Gly Trp Pro Pro Arg Lys Tyr Tyr Gln Phe
            115                 120                 125

Arg Lys Thr His Arg Phe Leu Arg Gln Phe Met Gln Leu Met Gln Arg
            130                 135                 140

Ser Thr Arg Leu Ala Ala Ser Lys Val Leu Ser Ile Ser Lys Asn Ser
145                 150                 155                 160

Pro Ile Ser Gln Ala Val His Ala Ala His Ala Glu Ile Asn Glu Ala
                165                 170                 175

Gly Arg Leu Glu Ser Ile Ile Asn Phe Glu Lys Leu Thr Asp Phe Ser
                180                 185                 190

Gly Ser Ser Cys Ser Ser Cys Arg Asp Gln Arg Gly Trp Pro Leu Glu
            195                 200                 205

Ser Ile Ile Asn Phe Glu Lys Leu Thr Asp Phe Ser Gly Ser Ser Cys
```

```
                  210                 215                 220
Ser Ser Cys Arg Asp Gln Arg Gly Trp Pro Gly Ile Trp Val Asn
225                 230                 235

<210> SEQ ID NO 36
<211> LENGTH: 237
<212> TYPE: PRT
<213> ORGANISM: Artificial
<220> FEATURE:
<223> OTHER INFORMATION: G142C

<400> SEQUENCE: 36

Met Arg Gly Ser His His His His His Gly Ile Arg Arg Gln Trp
1               5                   10                  15

Arg Tyr Pro Asp Phe Ser Gly Ser Ser Cys Ser Ser Cys Arg Asp Gln
                20                  25                  30

Arg Gly Trp Pro Arg Lys Tyr Tyr Gln Phe Arg Lys Thr His Arg Phe
            35                  40                  45

Leu Arg Gln Phe Met Gln Leu Met Gln Arg Ser Thr Arg Leu Ala Ala
        50                  55                  60

Leu Glu Ser Ile Ile Asn Phe Glu Lys Leu Thr Asp Phe Ser Gly Ser
65                  70                  75                  80

Ser Cys Ser Ser Cys Arg Asp Gln Arg Gly Trp Pro Pro Arg Lys Tyr
                85                  90                  95

Tyr Gln Phe Arg Lys Thr His Arg Phe Leu Arg Gln Phe Met Gln Leu
                100                 105                 110

Met Gln Arg Ser Thr Arg Leu Ala Ala Ser Lys Val Leu Ser Ile Ser
            115                 120                 125

Lys Asn Ser Pro Ile Ser Gln Ala Val His Ala Ala His Ala Glu Ile
        130                 135                 140

Asn Glu Ala Gly Arg Leu Glu Ser Ile Ile Asn Phe Glu Lys Leu Thr
145                 150                 155                 160

Asp Phe Ser Gly Ser Ser Cys Ser Ser Cys Arg Asp Gln Arg Gly Trp
                165                 170                 175

Pro Pro Arg Lys Tyr Tyr Gln Phe Arg Lys Thr His Arg Phe Leu Arg
            180                 185                 190

Gln Phe Met Gln Leu Met Gln Arg Ser Thr Arg Leu Ala Ala Arg Lys
        195                 200                 205

Tyr Tyr Gln Phe Arg Lys Thr His Arg Phe Leu Arg Gln Phe Met Gln
        210                 215                 220

Leu Met Gln Arg Ser Thr Arg Leu Ala Gly Asp Leu Gly
225                 230                 235

<210> SEQ ID NO 37
<211> LENGTH: 163
<212> TYPE: PRT
<213> ORGANISM: Artificial
<220> FEATURE:
<223> OTHER INFORMATION: F58B

<400> SEQUENCE: 37

Met Arg Gly Ser His His His His His Thr Asp Pro Ser Thr Val
1               5                   10                  15

Pro Arg Gly Trp Pro Gln Ser Ile Ile Asn Phe Glu Lys Leu Thr Asp
                20                  25                  30

Phe Ser Gly Ser Ser Cys Ser Ser Cys Arg Asp Gln Arg Gly Trp Pro
            35                  40                  45
```

```
Pro Arg Glu Tyr His Gln Leu Arg Glu Ala Tyr Arg Phe Leu Arg Gln
 50                  55                  60

Phe Met Gln Leu Met Gln Arg Ser Thr Arg Leu Ala Ala Ser Arg Val
 65                  70                  75                  80

Ser Ser Thr Ser Arg Ser Leu Pro Ile Ser Gln Ala Val His Ala Ala
                 85                  90                  95

His Ala Glu Ile Asn Glu Ala Gly Arg Leu Glu Ser Ile Ile Asn Phe
            100                 105                 110

Glu Lys Leu Thr Asp Phe Ser Gly Ser Ser Cys Ser Ser Cys Arg Asp
        115                 120                 125

Gln Arg Gly Trp Pro Arg Val Ser Ser Thr Ser Arg Ser Leu Pro Ile
    130                 135                 140

Ser Gln Ala Val His Ala Ala His Ala Glu Ile Asn Glu Ala Gly Gly
145                 150                 155                 160

Asp Leu Gly

<210> SEQ ID NO 38
<211> LENGTH: 166
<212> TYPE: PRT
<213> ORGANISM: Artificial
<220> FEATURE:
<223> OTHER INFORMATION: F58C

<400> SEQUENCE: 38

Met Arg Gly Ser His His His His His His Gly Ile Arg Gln Trp
 1               5                  10                  15

Arg Tyr Pro Glu Ala Gly Arg Arg Val Ser Ser Thr Ser Arg Ser Leu
                 20                  25                  30

Pro Ile Ser Gln Ala Val His Ala Ala His Ala Glu Ile Asn Glu Ala
            35                  40                  45

Gly Arg Leu Glu Ser Ile Ile Asn Phe Glu Lys Leu Thr Asp Phe Ser
        50                  55                  60

Gly Ser Ser Cys Ser Ser Cys Arg Asp Gln Arg Gly Trp Pro Pro Arg
 65                  70                  75                  80

Glu Tyr His Gln Leu Arg Glu Ala Tyr Arg Phe Leu Arg Gln Phe Met
                 85                  90                  95

Gln Leu Met Gln Arg Ser Thr Arg Leu Ala Ala Ser Arg Val Ser Ser
            100                 105                 110

Thr Ser Arg Ser Leu Pro Ile Ser Gln Ala Val His Ala Ala His Ala
        115                 120                 125

Glu Ile Asn Glu Ala Gly Arg Glu Tyr His Gln Leu Arg Glu Ala Tyr
    130                 135                 140

Arg Phe Leu Arg Gln Phe Met Gln Leu Met Gln Arg Ser Thr Arg Leu
145                 150                 155                 160

Ala Gly Ile Trp Val Asn
                165

<210> SEQ ID NO 39
<211> LENGTH: 207
<212> TYPE: PRT
<213> ORGANISM: Artificial
<220> FEATURE:
<223> OTHER INFORMATION: F112A

<400> SEQUENCE: 39

Met Arg Gly Ser His His His His His His Gly Ser Val Asp Gly Thr
 1               5                  10                  15
```

```
Arg Glu Ala Tyr Arg Phe Leu Arg Gln Phe Met Gln Leu Met Gln Arg
             20                  25                  30

Ser Thr Arg Leu Ala Ala Arg Glu Tyr His Gln Leu Arg Glu Ala Tyr
         35                  40                  45

Arg Phe Leu Arg Gln Phe Met Gln Leu Met Gln Arg Ser Thr Arg Leu
     50                  55                  60

Ala Ala Ser Arg Val Ser Ser Thr Ser Arg Ser Leu Pro Ile Ser Gln
 65                  70                  75                  80

Ala Val His Ala Ala His Ala Glu Ile Asn Glu Ala Gly Ser Arg Val
                 85                  90                  95

Ser Ser Thr Ser Arg Ser Leu Pro Ile Ser Gln Ala Val His Ala Ala
             100                 105                 110

His Ala Glu Ile Asn Glu Ala Gly Arg Ser Arg Val Ser Ser Thr Ser
         115                 120                 125

Arg Ser Leu Pro Ile Ser Gln Ala Val His Ala Ala His Ala Glu Ile
     130                 135                 140

Asn Glu Ala Gly Arg Arg Glu Tyr His Gln Leu Arg Glu Ala Tyr Leu
145                 150                 155                 160

Phe Leu Arg Gln Phe Met Gln Leu Met Gln Arg Ser Thr Arg Leu Ala
                 165                 170                 175

Leu Glu Ser Ile Ile Asn Phe Glu Lys Leu Thr Asp Phe Ser Gly Ser
             180                 185                 190

Ser Cys Ser Ser Cys Arg Asp Gln Arg Gly Gly Ile Trp Val Asn
         195                 200                 205

<210> SEQ ID NO 40
<211> LENGTH: 211
<212> TYPE: PRT
<213> ORGANISM: Artificial
<220> FEATURE:
<223> OTHER INFORMATION: F112C

<400> SEQUENCE: 40

Met Arg Gly Ser His His His His His Gly Ile Arg Arg Gln Trp
 1               5                  10                  15

Arg Tyr Pro Arg Ser Leu Pro Ile Ser Gln Gly Ser Cys Ser Ser
             20                  25                  30

Cys Arg Asp Gln Arg Gly Trp Pro Leu Glu Ser Ile Ile Asn Phe Glu
         35                  40                  45

Lys Leu Thr Asp Phe Ser Gly Ser Ser Cys Ser Ser Cys Arg Asp Gln
     50                  55                  60

Arg Gly Trp Pro Pro Arg Glu Tyr His Pro Leu Arg Glu Ala Tyr Arg
 65                  70                  75                  80

Phe Leu Arg Gln Phe Met Gln Leu Met Gln Arg Ser Thr Arg Leu Ala
                 85                  90                  95

Arg Glu Tyr His Gln Leu Arg Glu Ala Tyr Arg Phe Leu Arg Gln Phe
             100                 105                 110

Met Gln Leu Met Gln Arg Ser Thr Arg Leu Ala Ala Arg Glu Tyr His
         115                 120                 125

Gln Leu Arg Glu Ala Tyr Arg Phe Leu Arg Gln Phe Met Gln Leu Met
     130                 135                 140

Gln Arg Ser Thr Arg Leu Ala Ala Glu Ser Ile Ile Asn Phe Glu Lys
145                 150                 155                 160

Leu Thr Tyr Phe Ser Gly Ser Ser Cys Ser Ser Cys Arg Asp Gln Arg
                 165                 170                 175
```

```
Gly Trp Pro Ser Arg Val Ser Ser Thr Ser Arg Ser Leu Pro Ile Ser
            180                 185                 190

Gln Ala Val His Ala Ala His Ala Glu Ile Asn Glu Ala Gly Ser Gly
        195                 200                 205

Leu Ile Asn
    210

<210> SEQ ID NO 41
<211> LENGTH: 113
<212> TYPE: PRT
<213> ORGANISM: Artificial
<220> FEATURE:
<223> OTHER INFORMATION: MT290

<400> SEQUENCE: 41

Met Arg Gly Ser His His His His His Gly Ile Arg Arg Arg Tyr
1               5                   10                  15

Pro Glu Ser Leu Ala Arg Ala Tyr Gly Glu Leu Ala Ser Arg Ala Glu
            20                  25                  30

Ser Leu Ala Arg Ala Tyr Gly Glu Leu Ala Ser Arg Ala Glu Ser Leu
        35                  40                  45

Ala Arg Ala Tyr Gly Glu Leu Ala Ser Arg Ala Glu Ser Leu Ala Arg
    50                  55                  60

Ala Tyr Gly Glu Leu Ala Ser Arg Ala Glu Ser Leu Ala Arg Ala Tyr
65                  70                  75                  80

Gly Glu Leu Ala Ser Arg Gly Lys Ser Cys Lys Gly Val Trp Arg Thr
                85                  90                  95

Cys Lys Pro Ser Gly Lys Ser Cys Lys Gly Gly Ser Gly Leu Ile
            100                 105                 110

Asn

<210> SEQ ID NO 42
<211> LENGTH: 104
<212> TYPE: PRT
<213> ORGANISM: Artificial
<220> FEATURE:
<223> OTHER INFORMATION: MT297

<400> SEQUENCE: 42

Met Arg Gly Ser His His His His His Gly Ser Val Asp Gly Thr
1               5                   10                  15

Arg Thr Ser Lys Pro Asn Gly Lys Ser Tyr Arg Val Val Trp Arg Thr
            20                  25                  30

Ser Lys Pro Asn Gly Lys Ser Tyr Arg Val Val Trp Arg Thr Ser Lys
        35                  40                  45

Pro Asn Gly Lys Ser Tyr Arg Val Val Trp Arg Thr Ser Lys Pro Asn
    50                  55                  60

Gly Lys Ser Tyr Arg Val Val Trp Arg Thr Ser Lys Pro Asn Glu Lys
65                  70                  75                  80

Ser Tyr Arg Val Val Trp Arg Thr Ser Lys Pro Asn Arg Lys Val Leu
                85                  90                  95

Gln Gly Arg Gly Ile Trp Val Asn
            100

<210> SEQ ID NO 43
<211> LENGTH: 141
<212> TYPE: PRT
<213> ORGANISM: Artificial
<220> FEATURE:
```

<223> OTHER INFORMATION: MT332

<400> SEQUENCE: 43

Met Arg Gly Ser His Phe His His His His Gly Ile Arg Arg Arg
1               5                   10                  15

Tyr Pro Leu Gln Gly Arg Met Glu Asn Leu Gln Ala Glu Arg Lys Val
            20                  25                  30

Leu Gln Gly Arg Met Glu Asn Leu Gln Ala Glu Lys Gly Ser Ser Gly
        35                  40                  45

Pro Tyr Gly Glu Ser Ser Gly Arg Glu Arg Phe Phe Arg Ala Val Trp
    50                  55                  60

Arg Ile Phe Arg Gln Arg Lys Val Leu Gln Gly Arg Met Glu Asn Leu
65                  70                  75                  80

Gln Ala Glu Lys Gly Ser Ser Gly Pro Tyr Gly Glu Ser Ser Gly Arg
                85                  90                  95

Glu Arg Phe Phe Arg Ala Val Trp Arg Ile Phe Arg Gln Arg Lys Gly
            100                 105                 110

Ser Ser Gly Pro Tyr Gly Glu Ser Ser Gly Arg Glu Arg Phe Phe Arg
        115                 120                 125

Ala Val Trp Arg Ile Phe Arg Gly Ser Gly Leu Ile Asn
    130                 135                 140

<210> SEQ ID NO 44
<211> LENGTH: 181
<212> TYPE: PRT
<213> ORGANISM: Artificial
<220> FEATURE:
<223> OTHER INFORMATION: F37A

<400> SEQUENCE: 44

Met Arg Gly Ser His His His His His His Gly Ser Val Asp Trp Gly
1               5                   10                  15

Thr Arg Leu Pro Ile Ser Gln Ala Val His Ala Ala His Ala Glu Ile
            20                  25                  30

Asn Glu Ala Gly Arg Leu Glu Ser Ile Ile Asn Phe Glu Lys Leu Thr
        35                  40                  45

Asp Phe Ser Gly Ser Ser Cys Ser Cys Arg Asp Gln Arg Gly Trp
    50                  55                  60

Pro Leu Glu Ser Ile Ile Asn Phe Glu Lys Leu Thr Asp Phe Ser Gly
65                  70                  75                  80

Ser Ser Cys Ser Ser Cys Arg Asp Gln Arg Gly Trp Pro Leu Glu Ser
                85                  90                  95

Ile Ile Asn Phe Glu Lys Leu Thr Asp Phe Ser Gly Ser Ser Cys Ser
            100                 105                 110

Ser Cys Arg Asp Gln Arg Gly Trp Pro Pro Arg Glu Tyr His Gln Leu
        115                 120                 125

Arg Glu Ala Tyr Arg Phe Leu Arg Gln Phe Met Gln Leu Met Gln Arg
    130                 135                 140

Ser Thr Arg Leu Ala Ala Ser Arg Val Ser Ser Thr Ser Arg Ser Leu
145                 150                 155                 160

Pro Ile Ser Gln Ala Val His Ala Ala His Ala Glu Ile Asn Glu Ala
                165                 170                 175

Gly Gly Asp Leu Gly
            180

<210> SEQ ID NO 45

```
<211> LENGTH: 183
<212> TYPE: PRT
<213> ORGANISM: Artificial
<220> FEATURE:
<223> OTHER INFORMATION: F37AE2

<400> SEQUENCE: 45

Met Arg Gly Ser His His His His His Gly Ser Val Asp Trp Gly
1               5                   10                  15

Thr Arg Leu Pro Ile Ser Gln Ala Val His Ala Ala His Ala Glu Ile
            20                  25                  30

Asn Glu Ala Gly Arg Leu Glu Ser Ile Ile Asn Phe Glu Lys Leu Thr
        35                  40                  45

Asp Phe Ser Gly Ser Ser Cys Ser Ser Cys Arg Asp Gln Arg Gly Trp
    50                  55                  60

Pro Leu Glu Ser Ile Ile Asn Phe Glu Lys Leu Thr Asp Phe Ser Gly
65                  70                  75                  80

Ser Ser Cys Ser Ser Cys Arg Asp Gln Arg Gly Trp Pro Leu Glu Ser
                85                  90                  95

Ile Ile Asn Phe Glu Lys Leu Thr Asp Phe Ser Gly Ser Ser Cys Ser
            100                 105                 110

Ser Cys Arg Asp Gln Arg Gly Trp Pro Pro Arg Glu Tyr His Gln Leu
        115                 120                 125

Arg Glu Ala Tyr Arg Phe Leu Arg Gln Phe Met Gln Leu Met Gln Arg
    130                 135                 140

Ser Thr Arg Leu Ala Ala Ser Arg Val Ser Ser Thr Ser Arg Ser Leu
145                 150                 155                 160

Pro Ile Ser Gln Ala Val His Ala Ala His Ala Glu Ile Asn Glu Ala
                165                 170                 175

Gly Gly Ser Gly Leu Ile Asn
            180

<210> SEQ ID NO 46
<211> LENGTH: 184
<212> TYPE: PRT
<213> ORGANISM: Artificial
<220> FEATURE:
<223> OTHER INFORMATION: MT819

<400> SEQUENCE: 46

Met Arg Gly Ser His His His His His Gly Ser Val Asp Trp Gly
1               5                   10                  15

Thr Arg Leu Pro Ile Ser Gln Ala Val His Ala Ala His Ala Glu Ile
            20                  25                  30

Asn Glu Ala Gly Arg Leu Glu Arg Met Phe Pro Asn Ala Pro Tyr Leu
        35                  40                  45

Thr Asp Phe Ser Gly Ser Ser Cys Ser Ser Cys Arg Asp Gln Arg Gly
    50                  55                  60

Trp Pro Leu Glu Ser Ile Ile Asn Phe Glu Lys Leu Thr Asp Phe Ser
65                  70                  75                  80

Gly Ser Ser Cys Ser Ser Cys Arg Asp Gln Arg Gly Trp Pro Leu Glu
                85                  90                  95

Ser Ile Ile Asn Phe Glu Lys Leu Thr Asp Phe Ser Gly Ser Ser Cys
            100                 105                 110

Ser Ser Cys Arg Asp Gln Arg Gly Trp Pro Pro Arg Glu Tyr His Gln
        115                 120                 125

Leu Arg Glu Ala Tyr Arg Phe Leu Arg Gln Phe Met Gln Leu Met Gln
```

```
                130                 135                 140
Arg Ser Thr Arg Leu Ala Ala Ser Arg Val Ser Ser Thr Ser Arg Ser
145                 150                 155                 160

Leu Pro Ile Ser Gln Ala Val His Ala Ala His Ala Glu Ile Asn Glu
                165                 170                 175

Ala Gly Gly Ser Gly Leu Ile Asn
            180

<210> SEQ ID NO 47
<211> LENGTH: 184
<212> TYPE: PRT
<213> ORGANISM: Artificial
<220> FEATURE:
<223> OTHER INFORMATION: MT820

<400> SEQUENCE: 47

Met Arg Gly Ser His His His His His Gly Ser Val Asp Trp Gly
1               5                   10                  15

Thr Arg Leu Pro Ile Ser Gln Ala Val His Ala Ala His Ala Glu Ile
                20                  25                  30

Asn Glu Ala Gly Arg Leu Glu Ser Ile Ile Asn Phe Glu Lys Leu Thr
                35                  40                  45

Asp Phe Ser Gly Ser Ser Cys Ser Ser Cys Arg Asp Gln Arg Gly Trp
50                  55                  60

Pro Leu Glu Arg Met Phe Pro Asn Ala Pro Tyr Leu Thr Asp Phe Ser
65                  70                  75                  80

Gly Ser Ser Cys Ser Ser Cys Arg Asp Gln Arg Gly Trp Pro Leu Glu
                85                  90                  95

Ser Ile Ile Asn Phe Glu Lys Leu Thr Asp Phe Ser Gly Ser Ser Cys
                100                 105                 110

Ser Ser Cys Arg Asp Gln Arg Gly Trp Pro Pro Arg Glu Tyr His Gln
                115                 120                 125

Leu Arg Glu Ala Tyr Arg Phe Leu Arg Gln Phe Met Gln Leu Met Gln
            130                 135                 140

Arg Ser Thr Arg Leu Ala Ala Ser Arg Val Ser Ser Thr Ser Arg Ser
145                 150                 155                 160

Leu Pro Ile Ser Gln Ala Val His Ala Ala His Ala Glu Ile Asn Glu
                165                 170                 175

Ala Gly Gly Ser Gly Leu Ile Asn
            180

<210> SEQ ID NO 48
<211> LENGTH: 184
<212> TYPE: PRT
<213> ORGANISM: Artificial
<220> FEATURE:
<223> OTHER INFORMATION: MT821

<400> SEQUENCE: 48

Met Arg Gly Ser His His His His His Gly Ser Val Asp Trp Gly
1               5                   10                  15

Thr Arg Leu Pro Ile Ser Gln Ala Val His Ala Ala His Ala Glu Ile
                20                  25                  30

Asn Glu Ala Gly Arg Leu Glu Ser Ile Ile Asn Phe Glu Lys Leu Thr
                35                  40                  45

Asp Phe Ser Gly Ser Ser Cys Ser Ser Cys Arg Asp Gln Arg Gly Trp
50                  55                  60
```

```
Pro Leu Glu Ser Ile Ile Asn Phe Glu Lys Leu Thr Asp Phe Ser Gly
 65                  70                  75                  80

Ser Ser Cys Ser Ser Cys Arg Asp Gln Arg Gly Trp Pro Leu Glu Arg
                 85                  90                  95

Met Phe Pro Asn Ala Pro Tyr Leu Thr Asp Phe Ser Gly Ser Ser Cys
            100                 105                 110

Ser Ser Cys Arg Asp Gln Arg Gly Trp Pro Pro Arg Glu Tyr His Gln
            115                 120                 125

Leu Arg Glu Ala Tyr Arg Phe Leu Arg Gln Phe Met Gln Leu Met Gln
        130                 135                 140

Arg Ser Thr Arg Leu Ala Ala Ser Arg Val Ser Ser Thr Ser Arg Ser
145                 150                 155                 160

Leu Pro Ile Ser Gln Ala Val His Ala Ala His Ala Glu Ile Asn Glu
                165                 170                 175

Ala Gly Gly Ser Gly Leu Ile Asn
            180
```

<210> SEQ ID NO 49
<211> LENGTH: 185
<212> TYPE: PRT
<213> ORGANISM: Artificial
<220> FEATURE:
<223> OTHER INFORMATION: MT822

<400> SEQUENCE: 49

```
Met Arg Gly Ser His His His His His His Gly Ser Val Asp Trp Gly
 1               5                  10                  15

Thr Arg Leu Pro Ile Ser Gln Ala Val His Ala Ala His Ala Glu Ile
             20                  25                  30

Asn Glu Ala Gly Arg Leu Glu Arg Met Phe Pro Asn Ala Pro Tyr Leu
         35                  40                  45

Thr Asp Phe Ser Gly Ser Ser Cys Ser Cys Arg Asp Gln Arg Gly
     50                  55                  60

Trp Pro Leu Glu Arg Met Phe Pro Asn Ala Pro Tyr Leu Thr Asp Phe
 65                  70                  75                  80

Ser Gly Ser Ser Cys Ser Ser Cys Arg Asp Gln Arg Gly Trp Pro Leu
                 85                  90                  95

Glu Ser Ile Ile Asn Phe Glu Lys Leu Thr Asp Phe Ser Gly Ser Ser
            100                 105                 110

Cys Ser Ser Cys Arg Asp Gln Arg Gly Trp Pro Pro Arg Glu Tyr His
            115                 120                 125

Gln Leu Arg Glu Ala Tyr Arg Phe Leu Arg Gln Phe Met Gln Leu Met
        130                 135                 140

Gln Arg Ser Thr Arg Leu Ala Ala Ser Arg Val Ser Ser Thr Ser Arg
145                 150                 155                 160

Ser Leu Pro Ile Ser Gln Ala Val His Ala Ala His Ala Glu Ile Asn
                165                 170                 175

Glu Ala Gly Gly Ser Gly Leu Ile Asn
            180                 185
```

<210> SEQ ID NO 50
<211> LENGTH: 185
<212> TYPE: PRT
<213> ORGANISM: Artificial
<220> FEATURE:
<223> OTHER INFORMATION: MT823

<400> SEQUENCE: 50

```
Met Arg Gly Ser His His His His His Gly Ser Val Asp Trp Gly
1               5                   10                  15

Thr Arg Leu Pro Ile Ser Gln Ala Val His Ala Ala His Ala Glu Ile
            20                  25                  30

Asn Glu Ala Gly Arg Leu Glu Ser Ile Ile Asn Phe Glu Lys Leu Thr
        35                  40                  45

Asp Phe Ser Gly Ser Ser Cys Ser Ser Cys Arg Asp Gln Arg Gly Trp
50                  55                  60

Pro Leu Glu Arg Met Phe Pro Asn Ala Pro Tyr Leu Thr Asp Phe Ser
65                  70                  75                  80

Gly Ser Ser Cys Ser Ser Cys Arg Asp Gln Arg Gly Trp Pro Leu Glu
                85                  90                  95

Arg Met Phe Pro Asn Ala Pro Tyr Leu Thr Asp Phe Ser Gly Ser Ser
                100                 105                 110

Cys Ser Ser Cys Arg Asp Gln Arg Gly Trp Pro Pro Arg Glu Tyr His
            115                 120                 125

Gln Leu Arg Glu Ala Tyr Arg Phe Leu Arg Gln Phe Met Gln Leu Met
        130                 135                 140

Gln Arg Ser Thr Arg Leu Ala Ala Ser Arg Val Ser Ser Thr Ser Arg
145                 150                 155                 160

Ser Leu Pro Ile Ser Gln Ala Val His Ala Ala His Ala Glu Ile Asn
                165                 170                 175

Glu Ala Gly Gly Ser Gly Leu Ile Asn
            180                 185

<210> SEQ ID NO 51
<211> LENGTH: 185
<212> TYPE: PRT
<213> ORGANISM: Artificial
<220> FEATURE:
<223> OTHER INFORMATION: MT824

<400> SEQUENCE: 51

Met Arg Gly Ser His His His His His Gly Ser Val Asp Trp Gly
1               5                   10                  15

Thr Arg Leu Pro Ile Ser Gln Ala Val His Ala Ala His Ala Glu Ile
            20                  25                  30

Asn Glu Ala Gly Arg Leu Glu Arg Met Phe Pro Asn Ala Pro Tyr Leu
        35                  40                  45

Thr Asp Phe Ser Gly Ser Ser Cys Ser Ser Cys Arg Asp Gln Arg Gly
50                  55                  60

Trp Pro Leu Glu Ser Ile Ile Asn Phe Glu Lys Leu Thr Asp Phe Ser
65                  70                  75                  80

Gly Ser Ser Cys Ser Ser Cys Arg Asp Gln Arg Gly Trp Pro Leu Glu
                85                  90                  95

Arg Met Phe Pro Asn Ala Pro Tyr Leu Thr Asp Phe Ser Gly Ser Ser
                100                 105                 110

Cys Ser Ser Cys Arg Asp Gln Arg Gly Trp Pro Pro Arg Glu Tyr His
            115                 120                 125

Gln Leu Arg Glu Ala Tyr Arg Phe Leu Arg Gln Phe Met Gln Leu Met
        130                 135                 140

Gln Arg Ser Thr Arg Leu Ala Ala Ser Arg Val Ser Ser Thr Ser Arg
145                 150                 155                 160

Ser Leu Pro Ile Ser Gln Ala Val His Ala Ala His Ala Glu Ile Asn
                165                 170                 175
```

Glu Ala Gly Gly Ser Gly Leu Ile Asn
            180                 185

<210> SEQ ID NO 52
<211> LENGTH: 186
<212> TYPE: PRT
<213> ORGANISM: Artificial
<220> FEATURE:
<223> OTHER INFORMATION: MT825

<400> SEQUENCE: 52

Met Arg Gly Ser His His His His His Gly Ser Val Asp Trp Gly
1               5                   10                  15

Thr Arg Leu Pro Ile Ser Gln Ala Val His Ala Ala His Ala Glu Ile
                20                  25                  30

Asn Glu Ala Gly Arg Leu Glu Arg Met Phe Pro Asn Ala Pro Tyr Leu
            35                  40                  45

Thr Asp Phe Ser Gly Ser Ser Cys Ser Ser Cys Arg Asp Gln Arg Gly
    50                  55                  60

Trp Pro Leu Glu Arg Met Phe Pro Asn Ala Pro Tyr Leu Thr Asp Phe
65                  70                  75                  80

Ser Gly Ser Ser Cys Ser Ser Cys Arg Asp Gln Arg Gly Trp Pro Leu
                85                  90                  95

Glu Arg Met Phe Pro Asn Ala Pro Tyr Leu Thr Asp Phe Ser Gly Ser
            100                 105                 110

Ser Cys Ser Ser Cys Arg Asp Gln Arg Gly Trp Pro Pro Arg Glu Tyr
        115                 120                 125

His Gln Leu Arg Glu Ala Tyr Arg Phe Leu Arg Gln Phe Met Gln Leu
    130                 135                 140

Met Gln Arg Ser Thr Arg Leu Ala Ala Ser Arg Val Ser Ser Thr Ser
145                 150                 155                 160

Arg Ser Leu Pro Ile Ser Gln Ala Val His Ala Ala His Ala Glu Ile
                165                 170                 175

Asn Glu Ala Gly Gly Ser Gly Leu Ile Asn
            180                 185

<210> SEQ ID NO 53
<211> LENGTH: 25
<212> TYPE: PRT
<213> ORGANISM: Artificial
<220> FEATURE:
<223> OTHER INFORMATION: tandem repeat unit

<400> SEQUENCE: 53

Leu Glu Ser Ile Ile Asn Phe Glu Lys Leu Thr Asp Leu Arg Gln Phe
1               5                   10                  15

Thr Cys Arg Asp Gln Arg Gly Trp Pro
                20                  25

<210> SEQ ID NO 54
<211> LENGTH: 193
<212> TYPE: PRT
<213> ORGANISM: Artificial Sequence
<220> FEATURE:
<223> OTHER INFORMATION: AkiKaze A24

<400> SEQUENCE: 54

Met Arg Gly Ser His His His His His Gly Ser Val Asp Trp Gly
1               5                   10                  15

Thr Arg Leu Pro Lys Arg Tyr Phe Lys Leu Ser His Leu Gln Met His
            20                  25                  30

Ser Arg Lys His Gly Ser Leu Glu Cys Tyr Thr Trp Asn Gln Met Asn
        35                  40                  45

Leu Gly Ala Thr Asp Phe Ser Gly Ser Ser Cys Ser Cys Arg Asp
    50                  55                  60

Gln Arg Gly Trp Pro Leu Glu Cys Tyr Thr Trp Asn Gln Met Asn Leu
65                  70                  75                  80

Gly Ala Thr Asp Phe Ser Gly Ser Ser Cys Ser Cys Arg Asp Gln
                85                  90                  95

Arg Gly Trp Pro Leu Glu Cys Tyr Thr Trp Asn Gln Met Asn Leu Gly
                100                 105                 110

Ala Thr Asp Phe Ser Gly Ser Ser Cys Ser Cys Arg Asp Gln Arg
            115                 120                 125

Gly Trp Pro Val Asp Leu Glu Pro Arg Glu Tyr His Gln Leu Arg Glu
            130                 135                 140

Ala Tyr Arg Phe Leu Arg Gln Phe Met Gln Leu Met Gln Arg Ser Thr
145                 150                 155                 160

Arg Leu Ala Ala Ser Arg Val Ser Ser Thr Ser Arg Ser Leu Pro Lys
                165                 170                 175

Arg Tyr Phe Lys Leu Ser His Leu Gln Met His Ser Arg Lys His Gly
                180                 185                 190

Asp

<210> SEQ ID NO 55
<211> LENGTH: 193
<212> TYPE: PRT
<213> ORGANISM: Artificial Sequence
<220> FEATURE:
<223> OTHER INFORMATION: AkiKaze A2

<400> SEQUENCE: 55

Met Arg Gly Ser His His His His His His Gly Ser Val Asp Trp Gly
1               5                   10                  15

Thr Arg Leu Pro Lys Arg Tyr Phe Lys Leu Ser His Leu Gln Met His
            20                  25                  30

Ser Arg Lys His Gly Ser Val Asp Gln Ala Arg Met Phe Pro Asn Ala
        35                  40                  45

Pro Tyr Leu Pro Ser Thr Asp Phe Ser Gly Ser Ser Cys Ser Ser Cys
    50                  55                  60

Arg Asp Gln Arg Gly Trp Pro Gln Ala Arg Met Phe Pro Asn Ala Pro
65                  70                  75                  80

Tyr Leu Pro Ser Thr Asp Phe Ser Gly Ser Ser Cys Ser Ser Cys Arg
                85                  90                  95

Asp Gln Arg Gly Trp Pro Gln Ala Arg Met Phe Pro Asn Ala Pro Tyr
                100                 105                 110

Leu Pro Ser Thr Asp Phe Ser Gly Ser Ser Cys Ser Ser Cys Arg Asp
            115                 120                 125

Gln Arg Gly Trp Pro Leu Glu Pro Arg Glu Tyr His Gln Leu Arg Glu
            130                 135                 140

Ala Tyr Arg Phe Leu Arg Gln Phe Met Gln Leu Met Gln Arg Ser Thr
145                 150                 155                 160

Arg Leu Ala Ala Ser Arg Val Ser Ser Thr Ser Arg Ser Leu Pro Lys
                165                 170                 175

Arg Tyr Phe Lys Leu Ser His Leu Gln Met His Ser Arg Lys His Gly

<210> SEQ ID NO 56
<211> LENGTH: 286
<212> TYPE: PRT
<213> ORGANISM: Artificial Sequence
<220> FEATURE:
<223> OTHER INFORMATION: AkiKaze A242

<400> SEQUENCE: 56

```
Met Arg Gly Ser His His His His His His Gly Ser Val Asp Trp Gly
1               5                   10                  15

Thr Arg Leu Pro Lys Arg Tyr Phe Lys Leu Ser His Leu Gln Met His
            20                  25                  30

Ser Arg Lys His Gly Ser Leu Glu Cys Tyr Thr Trp Asn Gln Met Asn
        35                  40                  45

Leu Gly Ala Thr Asp Phe Ser Gly Ser Ser Cys Ser Cys Arg Asp
    50                  55                  60

Gln Arg Gly Trp Pro Leu Glu Cys Tyr Thr Trp Asn Gln Met Asn Leu
65                  70                  75                  80

Gly Ala Thr Asp Phe Ser Gly Ser Ser Cys Ser Cys Arg Asp Gln
            85                  90                  95

Arg Gly Trp Pro Leu Glu Cys Tyr Thr Trp Asn Gln Met Asn Leu Gly
            100                 105                 110

Ala Thr Asp Phe Ser Gly Ser Ser Cys Ser Cys Arg Asp Gln Arg
        115                 120                 125

Gly Trp Pro Val Asp Gln Ala Arg Met Phe Pro Asn Ala Pro Tyr Leu
        130                 135                 140

Pro Ser Thr Asp Phe Ser Gly Ser Ser Cys Ser Cys Arg Asp Gln
145                 150                 155                 160

Arg Gly Trp Pro Gln Ala Arg Met Phe Pro Asn Ala Pro Tyr Leu Pro
            165                 170                 175

Ser Thr Asp Phe Ser Gly Ser Ser Cys Ser Cys Arg Asp Gln Arg
            180                 185                 190

Gly Trp Pro Gln Ala Arg Met Phe Pro Asn Ala Pro Tyr Leu Pro Ser
        195                 200                 205

Thr Asp Phe Ser Gly Ser Ser Cys Ser Cys Arg Asp Gln Arg Gly
    210                 215                 220

Trp Pro Leu Glu Pro Arg Glu Tyr His Gln Leu Arg Glu Ala Tyr Arg
225                 230                 235                 240

Phe Leu Arg Gln Phe Met Gln Leu Met Gln Arg Ser Thr Arg Leu Ala
                245                 250                 255

Ala Ser Arg Val Ser Ser Thr Ser Arg Ser Leu Pro Lys Arg Tyr Phe
            260                 265                 270

Lys Leu Ser His Leu Gln Met His Ser Arg Lys His Gly Asp
        275                 280                 285
```

<210> SEQ ID NO 57
<211> LENGTH: 252
<212> TYPE: PRT
<213> ORGANISM: Artificial Sequence
<220> FEATURE:
<223> OTHER INFORMATION: WT1 A2 8110

<400> SEQUENCE: 57

Met Arg Gly Ser His His His His His His Gly Ser Val Asp Trp Gly

```
              1               5                  10                 15
            Thr Gly Ser Tyr Val Gln Cys Ser Leu Ser Ser Phe Leu Arg Asn Lys
                          20                 25                 30

Arg Tyr Phe Lys Leu Ser His Leu Gln Met His Ser Arg Lys His Gly
                          35                 40                 45

Ser Val Asp Gln Ala Arg Met Phe Pro Asn Ala Pro Tyr Leu Pro Ser
                          50                 55                 60

Thr Asp Phe Ser Gly Ser Ser Cys Ser Ser Cys Arg Asp Gln Arg Gly
             65                 70                 75                 80

Trp Pro Gln Ala Arg Met Phe Pro Asn Ala Pro Tyr Leu Pro Ser Thr
                               85                 90                 95

Asp Phe Ser Gly Ser Ser Cys Ser Ser Cys Arg Asp Gln Arg Gly Trp
                          100                105                110

Pro Gln Ala Arg Met Phe Pro Asn Ala Pro Tyr Leu Pro Ser Thr Asp
                          115                120                125

Phe Ser Gly Ser Ser Cys Ser Ser Cys Arg Asp Gln Arg Gly Trp Pro
                          130                135                140

Leu Glu Arg Leu Ala Val Cys Ser Met Leu Leu Ile Phe Leu Leu Ala
            145                150                155                160

Glu Gln Ala Leu Leu Gln Ala Leu Ala Leu Ala Asp Ala Leu Ala Glu
                          165                170                175

Ala Gly Ser Tyr Val Gln Cys Ser Leu Ser Ser Phe Leu Arg Asn Lys
                          180                185                190

Arg Tyr Phe Lys Leu Ser His Leu Gln Met His Ser Arg Lys His Val
                          195                200                205

Asp Asp Tyr Lys Asp His Asp Gly Asp Tyr Lys Asp His Asp Ile Asp
                          210                215                220

Tyr Lys Asp Asp Asp Asp Lys Leu Val Asp Lys Leu Leu Glu Ser Ile
            225                230                235                240

Ile Asn Phe Glu Lys Leu Thr Asp Lys Leu Gly Asp
                          245                250

<210> SEQ ID NO 58
<211> LENGTH: 252
<212> TYPE: PRT
<213> ORGANISM: Artificial Sequence
<220> FEATURE:
<223> OTHER INFORMATION: WT1 A24 8112

<400> SEQUENCE: 58

Met Arg Gly Ser His His His His His His Gly Ser Val Asp Trp Gly
             1               5                  10                 15

Thr Gly Ser Tyr Val Gln Cys Ser Leu Ser Ser Phe Leu Arg Asn Lys
                          20                 25                 30

Arg Tyr Phe Lys Leu Ser His Leu Gln Met His Ser Arg Lys His Gly
                          35                 40                 45

Ser Leu Glu Cys Tyr Thr Trp Asn Gln Met Asn Leu Gly Ala Gly Thr
                          50                 55                 60

Ser Val Thr Ser Ser Arg Thr Cys Arg Cys Thr Arg Gly Ser Thr
             65                 70                 75                 80

Leu Glu Cys Tyr Thr Trp Asn Gln Met Asn Leu Gly Ala Gly Thr Ser
                               85                 90                 95

Val Thr Ser Ser Arg Thr Cys Arg Cys Thr Arg Gly Ser Thr Leu
                          100                105                110

Glu Cys Tyr Thr Trp Asn Gln Met Asn Leu Gly Ala Gly Thr Ser Val
```

-continued

```
            115                 120                 125
Thr Ser Ser Arg Thr Cys Arg Cys Thr Arg Gly Ser Thr Val Asp
        130                 135                 140
Leu Glu Arg Leu Ala Val Cys Ser Met Leu Leu Ile Phe Leu Leu Ala
145                 150                 155                 160
Glu Gln Ala Leu Leu Gln Ala Leu Ala Leu Ala Asp Ala Leu Ala Glu
                165                 170                 175
Ala Gly Ser Tyr Val Gln Cys Ser Leu Ser Ser Phe Leu Arg Asn Lys
                180                 185                 190
Arg Tyr Phe Lys Leu Ser His Leu Gln Met His Ser Arg Lys His Val
                195                 200                 205
Asp Asp Tyr Lys Asp His Asp Gly Asp Tyr Lys Asp His Asp Ile Asp
        210                 215                 220
Tyr Lys Asp Asp Asp Asp Lys Leu Val Asp Lys Leu Leu Glu Ser Ile
225                 230                 235                 240
Ile Asn Phe Glu Lys Leu Thr Asp Lys Leu Gly Asp
                245                 250
```

<210> SEQ ID NO 59
<211> LENGTH: 236
<212> TYPE: PRT
<213> ORGANISM: Artificial Sequence
<220> FEATURE:
<223> OTHER INFORMATION: WT1 A24 839

<400> SEQUENCE: 59

```
Met Arg Gly Ser His His His His His His Gly Ser Val Asp Trp Gly
1               5                   10                  15
Thr Gly Ser Tyr Val Gln Cys Ser Leu Ser Ser Phe Leu Arg Asn Lys
                20                  25                  30
Arg Tyr Phe Lys Leu Ser His Leu Gln Met His Ser Arg Lys His Gly
                35                  40                  45
Ser Leu Glu Cys Tyr Thr Trp Asn Gln Met Asn Leu Gly Ala Thr Asp
        50                  55                  60
Phe Ser Gly Ser Ser Cys Ser Ser Cys Arg Asp Gln Arg Gly Trp Pro
65                  70                  75                  80
Leu Glu Cys Tyr Thr Trp Asn Gln Met Asn Leu Gly Ala Thr Asp Phe
                85                  90                  95
Ser Gly Ser Ser Cys Ser Ser Cys Arg Asp Gln Arg Gly Trp Pro Leu
                100                 105                 110
Glu Cys Tyr Thr Trp Asn Gln Met Asn Leu Gly Ala Thr Asp Phe Ser
                115                 120                 125
Gly Ser Ser Cys Ser Ser Cys Arg Asp Gln Arg Gly Trp Pro Val Asp
        130                 135                 140
Leu Glu Arg Leu Ala Val Cys Ser Met Leu Leu Ile Phe Leu Leu Ala
145                 150                 155                 160
Glu Gln Ala Leu Leu Gln Ala Leu Ala Leu Ala Asp Ala Leu Ala Glu
                165                 170                 175
Ala Gly Ser Tyr Val Gln Cys Ser Leu Ser Ser Phe Leu Arg Asn Lys
                180                 185                 190
Arg Tyr Phe Lys Leu Ser His Leu Gln Met His Ser Arg Lys His Val
                195                 200                 205
Asp Asp Glu Asp Glu Asp Val Asp Lys Leu Leu Glu Ser Ile
        210                 215                 220
Ile Asn Phe Glu Lys Leu Thr Asp Lys Leu Gly Asp
```

<210> SEQ ID NO 60
<211> LENGTH: 236
<212> TYPE: PRT
<213> ORGANISM: Artificial Sequence
<220> FEATURE:
<223> OTHER INFORMATION: WT1 A2 8310

<400> SEQUENCE: 60

```
Met Arg Gly Ser His His His His His His Gly Ser Val Asp Trp Gly
1               5                   10                  15

Thr Gly Ser Tyr Val Gln Cys Ser Leu Ser Ser Phe Leu Arg Asn Lys
            20                  25                  30

Arg Tyr Phe Lys Leu Ser His Leu Gln Met His Ser Arg Lys His Gly
        35                  40                  45

Ser Val Asp Gln Ala Arg Met Phe Pro Asn Ala Pro Tyr Leu Pro Ser
    50                  55                  60

Thr Asp Phe Ser Gly Ser Ser Cys Ser Ser Cys Arg Asp Gln Arg Gly
65                  70                  75                  80

Trp Pro Gln Ala Arg Met Phe Pro Asn Ala Pro Tyr Leu Pro Ser Thr
                85                  90                  95

Asp Phe Ser Gly Ser Ser Cys Ser Ser Cys Arg Asp Gln Arg Gly Trp
            100                 105                 110

Pro Gln Ala Arg Met Phe Pro Asn Ala Pro Tyr Leu Pro Ser Thr Asp
        115                 120                 125

Phe Ser Gly Ser Ser Cys Ser Ser Cys Arg Asp Gln Arg Gly Trp Pro
    130                 135                 140

Leu Glu Arg Leu Ala Val Cys Ser Met Leu Leu Ile Phe Leu Leu Ala
145                 150                 155                 160

Glu Gln Ala Leu Leu Gln Ala Leu Ala Leu Ala Asp Ala Leu Ala Glu
                165                 170                 175

Ala Gly Ser Tyr Val Gln Cys Ser Leu Ser Ser Phe Leu Arg Asn Lys
            180                 185                 190

Arg Tyr Phe Lys Leu Ser His Leu Gln Met His Ser Arg Lys His Val
        195                 200                 205

Asp Asp Glu Asp Glu Asp Asp Val Asp Lys Leu Leu Glu Ser Ile
    210                 215                 220

Ile Asn Phe Glu Lys Leu Thr Asp Lys Leu Gly Asp
225                 230                 235
```

<210> SEQ ID NO 61
<211> LENGTH: 186
<212> TYPE: PRT
<213> ORGANISM: Artificial Sequence
<220> FEATURE:
<223> OTHER INFORMATION: His PADRE WT1 A2

<400> SEQUENCE: 61

```
Met Arg Gly Ser His His His His His His Gly Ser Val Asp Gly Thr
1               5                   10                  15

Arg Leu Pro Ala Lys Phe Val Ala Ala Trp Thr Leu Lys Ala Ala Ala
            20                  25                  30

Gly Ser Val Asp Gln Ala Arg Met Phe Pro Asn Ala Pro Tyr Leu Pro
        35                  40                  45

Ser Thr Asp Phe Ser Gly Ser Ser Cys Ser Ser Cys Arg Asp Gln Arg
    50                  55                  60
```

Gly Trp Pro Gln Ala Arg Met Phe Pro Asn Ala Pro Tyr Leu Pro Ser
65                  70                  75                  80

Thr Asp Phe Ser Gly Ser Ser Cys Ser Ser Cys Arg Asp Gln Arg Gly
                85                  90                  95

Trp Pro Gln Ala Arg Met Phe Pro Asn Ala Pro Tyr Leu Pro Ser Thr
            100                 105                 110

Asp Phe Ser Gly Ser Ser Cys Ser Ser Cys Arg Asp Gln Arg Gly Trp
        115                 120                 125

Pro Leu Glu Pro Arg Glu Tyr His Gln Leu Arg Glu Ala Tyr Arg Phe
    130                 135                 140

Leu Arg Gln Phe Met Gln Leu Met Gln Arg Ser Thr Arg Leu Ala Ala
145                 150                 155                 160

Ser Arg Val Ser Ser Thr Ser Arg Ser Leu Pro Ala Lys Phe Val Ala
                165                 170                 175

Ala Trp Thr Leu Lys Ala Ala Ala Gly Asp
                180                 185

<210> SEQ ID NO 62
<211> LENGTH: 186
<212> TYPE: PRT
<213> ORGANISM: Artificial Sequence
<220> FEATURE:
<223> OTHER INFORMATION: His PADRE WT1 A24

<400> SEQUENCE: 62

Met Arg Gly Ser His His His His His His Gly Ser Val Asp Gly Thr
1               5                   10                  15

Arg Leu Pro Ala Lys Phe Val Ala Ala Trp Thr Leu Lys Ala Ala Ala
            20                  25                  30

Gly Ser Leu Glu Cys Tyr Thr Trp Asn Gln Met Asn Leu Gly Ala Thr
        35                  40                  45

Asp Phe Ser Gly Ser Ser Cys Ser Ser Cys Arg Asp Gln Arg Gly Trp
    50                  55                  60

Pro Leu Glu Cys Tyr Thr Trp Asn Gln Met Asn Leu Gly Ala Thr Asp
65                  70                  75                  80

Phe Ser Gly Ser Ser Cys Ser Ser Cys Arg Asp Gln Arg Gly Trp Pro
                85                  90                  95

Leu Glu Cys Tyr Thr Trp Asn Gln Met Asn Leu Gly Ala Thr Asp Phe
            100                 105                 110

Ser Gly Ser Ser Cys Ser Ser Cys Arg Asp Gln Arg Gly Trp Pro Val
        115                 120                 125

Asp Leu Glu Pro Arg Glu Tyr His Gln Leu Arg Glu Ala Tyr Arg Phe
    130                 135                 140

Leu Arg Gln Phe Met Gln Leu Met Gln Arg Ser Thr Arg Leu Ala Ala
145                 150                 155                 160

Ser Arg Val Ser Ser Thr Ser Arg Ser Leu Pro Ala Lys Phe Val Ala
                165                 170                 175

Ala Trp Thr Leu Lys Ala Ala Ala Gly Asp
                180                 185

<210> SEQ ID NO 63
<211> LENGTH: 203
<212> TYPE: PRT
<213> ORGANISM: Artificial Sequence
<220> FEATURE:
<223> OTHER INFORMATION: gp100 7172

<400> SEQUENCE: 63

-continued

```
Met Arg Gly Ser His His His His His Gly Ser Val Asp Trp Gly
1               5                   10                  15

Thr Arg Leu Pro Lys Ala Trp Asn Arg Gln Leu Tyr Pro Glu Trp Thr
            20                  25                  30

Glu Ala Gln Arg Leu Asp Cys Trp Gly Ser Ala Thr Lys Val Pro Arg
        35                  40                  45

Asn Gln Asp Trp Leu Gly Val Thr Asp Phe Ser Gly Ser Cys Ser
    50                  55                  60

Ser Cys Arg Asp Gln Arg Gly Trp Pro Ala Thr Lys Val Pro Arg Asn
65                  70                  75                  80

Gln Asp Trp Leu Gly Val Thr Asp Phe Ser Gly Ser Ser Cys Ser Ser
                85                  90                  95

Cys Arg Asp Gln Arg Gly Trp Pro Ala Thr Lys Val Pro Arg Asn Gln
                100                 105                 110

Asp Trp Leu Gly Val Thr Asp Phe Ser Gly Ser Ser Cys Ser Ser Cys
                115                 120                 125

Arg Asp Gln Arg Gly Trp Pro Ala Arg Glu Tyr His Gln Leu Arg Glu
                130                 135                 140

Ala Tyr Arg Phe Leu Arg Gln Phe Met Gln Leu Met Gln Arg Ser Thr
145                 150                 155                 160

Arg Leu Ala Ala Ser Arg Val Ser Ser Thr Ser Arg Ser Leu Pro Lys
                165                 170                 175

Ala Trp Asn Arg Gln Leu Tyr Pro Glu Trp Thr Glu Ala Gln Arg Leu
                180                 185                 190

Asp Cys Trp Val Asp Lys Leu Gly Asp Leu Gly
                195                 200

<210> SEQ ID NO 64
<211> LENGTH: 216
<212> TYPE: PRT
<213> ORGANISM: Artificial Sequence
<220> FEATURE:
<223> OTHER INFORMATION: C131B

<400> SEQUENCE: 64

Met Arg Gly Ser His His His His His His Thr Asp Pro Ser Thr Val
1               5                   10                  15

Pro Leu Arg Glu Ala Tyr Arg Ile Ser Gln Ala Val His Ala Ala His
            20                  25                  30

Ala Glu Ile Asn Glu Ala Gly Arg Leu Glu Ser Ile Ile Asn Phe Glu
        35                  40                  45

Lys Leu Thr Glu Phe Leu Arg Gln Phe Met Gln Leu Met Arg Arg Ser
    50                  55                  60

Thr Arg Leu Ala Glu Ser Ile Ile Asn Phe Glu Lys Leu Thr Glu Phe
65                  70                  75                  80

Leu Arg Gln Phe Met Gln Leu Met Gln Arg Ser Thr Arg Pro Arg Glu
                85                  90                  95

Tyr His Gln Leu Arg Glu Ala Tyr Arg Ile Ser Gln Ala Val His Ala
                100                 105                 110

Ala His Ala Glu Ile Asn Glu Ala Gly Arg Ser Arg Val Ser Ser Thr
                115                 120                 125

Ser Arg Ser Leu Pro Asn Phe Ser Gly Ser Ser Cys Ser Ser Cys Arg
                130                 135                 140

Asp Gln Arg Gly Trp Pro Pro Arg Glu Tyr His Gln Leu Arg Glu Ala
145                 150                 155                 160
```

```
Tyr Arg Ile Ser Gln Ala Val His Ala His Ala Glu Ile Asn Glu
            165                 170                 175

Ala Gly Arg Leu Glu Ser Ile Ile Asn Phe Glu Lys Leu Thr Glu Phe
        180                 185                 190

Leu Arg Gln Phe Met Gln Leu Met Gln Arg Ser Thr Arg Leu Ala Ala
        195                 200                 205

Arg Gly Gly Ser Gly Leu Ile Asn
    210                 215

<210> SEQ ID NO 65
<211> LENGTH: 12
<212> TYPE: PRT
<213> ORGANISM: Artificial Sequence
<220> FEATURE:
<223> OTHER INFORMATION: WT1 MHC class I epitope

<400> SEQUENCE: 65

Leu Glu Arg Met Phe Pro Asn Ala Pro Tyr Leu Thr
1               5                   10

<210> SEQ ID NO 66
<211> LENGTH: 84
<212> TYPE: PRT
<213> ORGANISM: Artificial Sequence
<220> FEATURE:
<223> OTHER INFORMATION: Tandem repeat structure

<400> SEQUENCE: 66

Leu Glu Ser Ile Ile Asn Phe Glu Lys Leu Thr Asp Phe Ser Gly Ser
1               5                   10                  15

Ser Cys Ser Ser Cys Arg Asp Gln Arg Gly Trp Pro Leu Glu Ser Ile
            20                  25                  30

Ile Asn Phe Glu Lys Leu Thr Asp Phe Ser Gly Ser Ser Cys Ser Ser
        35                  40                  45

Cys Arg Asp Gln Arg Gly Trp Pro Leu Glu Ser Ile Ile Asn Phe Glu
    50                  55                  60

Lys Leu Thr Asp Phe Ser Gly Ser Ser Cys Ser Ser Cys Arg Asp Gln
65                  70                  75                  80

Arg Gly Trp Pro

<210> SEQ ID NO 67
<211> LENGTH: 8
<212> TYPE: PRT
<213> ORGANISM: Artificial Sequence
<220> FEATURE:
<223> OTHER INFORMATION: MHC class I epitope of OVA

<400> SEQUENCE: 67

Ser Ile Ile Asn Phe Glu Lys Leu
1               5

<210> SEQ ID NO 68
<211> LENGTH: 87
<212> TYPE: PRT
<213> ORGANISM: Artificial Sequence
<220> FEATURE:
<223> OTHER INFORMATION: Tandem repeat structure

<400> SEQUENCE: 68

Leu Glu Arg Met Phe Pro Asn Ala Pro Tyr Leu Thr Asp Phe Ser Gly
1               5                   10                  15
```

```
Ser Ser Cys Ser Ser Cys Arg Asp Gln Arg Gly Trp Pro Leu Glu Arg
            20                  25                  30

Met Phe Pro Asn Ala Pro Tyr Leu Thr Asp Phe Ser Gly Ser Ser Cys
            35                  40                  45

Ser Ser Cys Arg Asp Gln Arg Gly Trp Pro Leu Glu Arg Met Phe Pro
    50                  55                  60

Asn Ala Pro Tyr Leu Thr Asp Phe Ser Gly Ser Ser Cys Ser Cys
65                  70                  75                  80

Arg Asp Gln Arg Gly Trp Pro
                85

<210> SEQ ID NO 69
<211> LENGTH: 23
<212> TYPE: PRT
<213> ORGANISM: Artificial Sequence
<220> FEATURE:
<223> OTHER INFORMATION: triple FLAG tag sequence

<400> SEQUENCE: 69

Asp Tyr Lys Asp His Asp Gly Asp Tyr Lys Asp His Asp Ile Asp Tyr
1               5                   10                  15

Lys Asp Asp Asp Asp Lys Leu
            20

<210> SEQ ID NO 70
<211> LENGTH: 7
<212> TYPE: PRT
<213> ORGANISM: Artificial Sequence
<220> FEATURE:
<223> OTHER INFORMATION: peptide sequence

<400> SEQUENCE: 70

Asp Glu Asp Glu Asp Glu Asp
1               5

<210> SEQ ID NO 71
<211> LENGTH: 9
<212> TYPE: PRT
<213> ORGANISM: Homo sapiens

<400> SEQUENCE: 71

Cys Met Thr Trp Asn Gln Met Asn Leu
1               5

<210> SEQ ID NO 72
<211> LENGTH: 9
<212> TYPE: PRT
<213> ORGANISM: Homo sapiens

<400> SEQUENCE: 72

Arg Met Phe Pro Asn Ala Pro Tyr Leu
1               5

<210> SEQ ID NO 73
<211> LENGTH: 22
<212> TYPE: PRT
<213> ORGANISM: Homo sapiens

<400> SEQUENCE: 73

Pro Gly Cys Asn Lys Arg Tyr Phe Lys Leu Ser His Leu Gln Met His
1               5                   10                  15

Ser Arg Lys His Thr Gly
            20
```

<210> SEQ ID NO 74
<211> LENGTH: 12
<212> TYPE: PRT
<213> ORGANISM: Homo sapiens

<400> SEQUENCE: 74

Gln Ala Arg Met Phe Pro Asn Ala Pro Tyr Leu Pro
1               5                   10

<210> SEQ ID NO 75
<211> LENGTH: 9
<212> TYPE: PRT
<213> ORGANISM: Artificial Sequence
<220> FEATURE:
<223> OTHER INFORMATION: WT1-derived MHC class I epitope

<400> SEQUENCE: 75

Cys Tyr Thr Trp Asn Gln Met Asn Leu
1               5

<210> SEQ ID NO 76
<211> LENGTH: 16
<212> TYPE: PRT
<213> ORGANISM: Artificial Sequence
<220> FEATURE:
<223> OTHER INFORMATION: WT1-derived MHC class II epitope

<400> SEQUENCE: 76

Lys Arg Tyr Phe Lys Leu Ser His Leu Gln Met His Ser Arg Lys His
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: Pan HLA-DR-binding epitope (PADRE)

<400> SEQUENCE: 77

Ala Lys Phe Val Ala Ala Trp Thr Leu Lys Ala Ala Ala
1               5                   10

<210> SEQ ID NO 78
<211> LENGTH: 9
<212> TYPE: PRT
<213> ORGANISM: Artificial Sequence
<220> FEATURE:
<223> OTHER INFORMATION: gp100-derived MHC class I epitope

<400> SEQUENCE: 78

Lys Val Pro Arg Asn Gln Asp Trp Leu
1               5

<210> SEQ ID NO 79
<211> LENGTH: 16
<212> TYPE: PRT
<213> ORGANISM: Artificial Sequence
<220> FEATURE:
<223> OTHER INFORMATION: gp100-derived MHC class II epitope

<400> SEQUENCE: 79

Trp Asn Arg Gln Leu Tyr Pro Glu Trp Thr Glu Ala Gln Arg Leu Asp
1               5                   10                  15

<210> SEQ ID NO 80

```
<211> LENGTH: 12
<212> TYPE: PRT
<213> ORGANISM: Artificial Sequence
<220> FEATURE:
<223> OTHER INFORMATION: peptide sequence (SEQ ID NO:1 + E) shown in
      Fig. 2

<400> SEQUENCE: 80

Leu Glu Ser Ile Ile Asn Phe Glu Lys Leu Thr Glu
1               5                   10

<210> SEQ ID NO 81
<211> LENGTH: 16
<212> TYPE: PRT
<213> ORGANISM: Artificial Sequence
<220> FEATURE:
<223> OTHER INFORMATION: peptide sequence shown in Fig. 2

<400> SEQUENCE: 81

Phe Ser Gly Ser Ser Cys Ser Ser Cys Arg Asp Gln Arg Gly Trp Pro
1               5                   10                  15

<210> SEQ ID NO 82
<211> LENGTH: 36
<212> TYPE: DNA
<213> ORGANISM: Artificial Sequence
<220> FEATURE:
<223> OTHER INFORMATION: nucleotide sequence shown in Fig. 2

<400> SEQUENCE: 82
ctcgagagta tcatcaactt cgagaagctt accgag                              36

<210> SEQ ID NO 83
<211> LENGTH: 51
<212> TYPE: DNA
<213> ORGANISM: Artificial Sequence
<220> FEATURE:
<223> OTHER INFORMATION: nucleotide sequence shown in Fig. 2

<400> SEQUENCE: 83
atttctcagg cagttcatgc agctcatgca gagatcaacg aggctggccg c             51
```

CELLULAR IMMUNITY INDUCING VACCINE

TECHNICAL FIELD

The present invention relates to a vaccine that can effectively induce cell-mediated immunity.

BACKGROUND ART

In recent years, tumor immunotherapy using an epitope peptide (minimal peptide sequence presented by an MHC class I or class II molecule) is attracting attention. Epitope peptide vaccines are administered in the form of a suspension of an epitope peptide in an oil emulsion such as Montanide. It is thought that, in such immunization, large amounts of the epitope peptide bind to empty MHC molecules of antigen-presenting cells, or peptide replacement occurs due to competition with peptides that are already bound to MHC molecules, leading to exertion of the function (Non-patent Documents 1 to 4). However, since this method does not include the inherent process of antigen processing by dendritic cells or the like, the efficiency of antigen presentation may be low. Moreover, it has recently been reported that oil adjuvants, which are indispensable for epitope peptide vaccines, cannot efficiently produce an antitumor effect since inflammation at the vaccination site causes localization of cytotoxic T cells (CTLs), which are responsible for attacking the tumor, in the vaccination site rather than the tumor site (Non-patent Document 5). Thus, development of peptide vaccines that can stably produce immunogenicity without using oil adjuvants has been hoped.

On the other hand, it is thought that, in cases where a full-length protein is used as an immunogen, the protein is processed by antigen-presenting cells such as dendritic cells, but the number of epitopes per protein molecule decreases, so that the amount of peptide presented by MHC molecules may be smaller than that in cases of epitope peptide immunization.

Antigens administered as vaccines are recognized in the body as foreign antigens, and incorporated into antigen-presenting cells. The antigens are then presented by MHC class II molecules, and tend to induce humoral immunity. For diseases such as AIDS, malaria, and malignant tumors, induction of cell-mediated immunity is important. In these diseases, humoral immunity is not capable of responding to the diseases since specific antigens of the diseases are not expressed on the cell surface, where recognition by antibodies occur. Since the antigens specific to these diseases undergo processing in cells as endogenous antigens, and are presented by MHC class I molecules, only cell-mediated immunity can produce an effect. Thus, for immunotherapies against such diseases using a protein as an antigen, development of a system that allows induction of cell-mediated immunity rather than humoral immunity has been hoped.

It is known that professional antigen-presenting cells such as dendritic cells have a mechanism that allows induction of cell-mediated immunity against foreign antigens. This system is called cross-presentation. In this phenomenon, antigens incorporated as foreign antigens into antigen-presenting cells undergo degradation by proteasome, and are presented by MHC class I molecules. However, the types of antigens that are likely to undergo cross-presentation and details of the mechanism of this phenomenon are still unclear.

PRIOR ART DOCUMENTS

Non-Patent Documents

Non-patent Document 1: Yamada A, et al. Cancer Sci. 2013 January; 104(1): 15-21. doi: 10.1111/cas.12050. Epub 2012 Dec. 4. Next-generation peptide vaccines for advanced cancer.

Non-patent Document 2: Khazaie K, et al. Curr Opin Oncol. 2009 November; 21(6): 524-30. doi: 10.1097/CCO.0b013e328331a78e. Current developments with peptide-based human tumor vaccines.

Non-patent Document 3: Perez S A, et al. Cancer. 2010 May 1; 116(9): 2071-80. doi: 10.1002/cncr.24988. A new era in anticancer peptide vaccines.

Non-patent Document 4: Slingluff C L Jr. Cancer J. 2011 September-October; 17(5): 343-50. doi: 10.1097/PPO.0b013e318233e5b2. The present and future of peptide vaccines for cancer: single or multiple, long or short, alone or in combination?

Non-patent Document 5: Hailemichael Y, et al. Nat Med. 2013 April; 19(4): 465-72. doi: 10.1038/nm.3105. Epub 2013 Mar. 3. Persistent antigen at vaccination sites induces tumor-specific $CD8^+$ T cell sequestration, dysfunction and deletion.

SUMMARY OF THE INVENTION

Problems to be Solved by the Invention

Accordingly, an object of the present invention is to provide a novel vaccine that allows induction of sufficiently high cell-mediated immunity.

Means for Solving the Problems

From the viewpoint of obtaining a high therapeutic effect by a vaccine, a peptide vaccine is thought to be more preferred since it can induce cross-presentation. The present inventors thought that the defects of conventional immunization using a short polypeptide such as an epitope peptide or a polypeptide having a large size such as a full-length protein can be overcome by use of an artificial protein obtained by improving the higher-order structure of peptide vaccines. In view of this, the present inventors intensively studied using an artificial protein creation technology based on the MolCraft method, which was developed by Kiyotaka Shiba et al., and, as a result, succeeded in identifying a structure important for artificial protein antigens which allow induction of strong cell-mediated immunity, thereby completing the present invention.

That is, the present invention provides a vaccine containing as an effective component a polypeptide comprising a tandem repeat structure in which an MHC class I epitope region and a spacer sequence are linked to each other alternately and repeatedly at least three times, wherein each of MHC class I epitope regions is derived from an antigen protein and each of spacer sequences is either (1) or (2) described below, or a recombinant vector which comprises a polynucleotide encoding said polypeptide and is capable of expressing said polypeptide in vivo:

(1) a sequence generated as an amino acid sequence inevitably encoded by a single base sequence which is designed such that said MHC class I epitope region, an MHC class II epitope region derived from the same or a different antigen protein mentioned above, and at least one higher-order-structure-stabilizing region are encoded by different reading frames in said single base sequence;

(2) a sequence which is the same amino acid sequence as (1) except that several amino acids are substituted.

The present invention also provides a vaccine containing as an effective component a polypeptide comprising a tandem repeat structure in which an MHC class I epitope region and a spacer sequence are linked to each other alternately and repeatedly at least three times, wherein each of MHC class I epitope regions is derived from an antigen protein and each of spacer sequences is either (1) or (2) described below, or a recombinant vector which comprises a polynucleotide encoding said polypeptide and is capable of expressing said polypeptide in vivo:

(1) a sequence generated as an amino acid sequence inevitably encoded by one reading frame in a single base sequence which is designed such that an MHC class II epitope derived from the same or a different antigen protein mentioned above and a higher-order-structure-stabilizing region(s) are encoded by different reading frames in said single base sequence, and such that no stop codon is generated in the remaining reading frame, said remaining reading frame being the above-mentioned one reading frame;

(2) a sequence which is the same amino acid sequence as (1) except that several amino acids are substituted.

Effect of the Invention

By the present invention, a peptide vaccine having an excellent capacity to induce cell-mediated immunity is provided. The peptide vaccine of the present invention has a cross-presentation capacity for MHC class I and MHC class II, and has a sufficiently high immune-inducing capacity. Even in cases where a smaller amount of oil adjuvant is used, or where no oil adjuvant is used, the peptide vaccine of the present invention can induce a much higher level of, for example, not less than 100 times higher level of, cell-mediated immunity than the original antigen protein. By the technique of the present invention, a vaccine having a high immune-inducing capacity can be provided even when a peptide epitope having only weak immunogenicity is used. For treatment and prevention of diseases such as malaria, AIDS, and tumors, induction of cell-mediated immunity is required. By the present invention, a vaccine effective for treatment and prevention of such diseases can be provided.

BRIEF DESCRIPTION OF THE DRAWINGS

FIG. 1 is a diagram illustrating construction of microgenes and artificial proteins. Panel (a) is the amino acid sequence of native antigen ovalbumin (OVA). Panel (b) shows microgenes designed in Examples. Panel (c) is a schematic diagram illustrating a scheme of construction of an artificial protein and showing various motifs and artificial proteins. Panel (d) shows the results of comparison of the in vitro antigen-presenting capacity among various artificial proteins and OVA. This panel also shows an SDS-PAGE image of artificial proteins.

FIG. 2 is a diagram illustrating the flow from designing of microgene #2101 to construction of an artificial protein gene.

FIG. 3 shows the amino acid sequences of artificial proteins.

FIG. 4 shows the amino acid sequences of artificial proteins.

FIG. 5 shows the results of analysis of the antigen-presenting capacity of the artificial protein F37A. Panel (a) is a diagram schematically showing the amino acid sequence of F37A and the sequences of other artificial proteins. Panel (b) shows the results of evaluation of the antigen-presenting capacity based on the level of in vitro IL-2 production. Panel (c) shows a diagram illustrating the structures of mutants prepared by replacing an MHC class I epitope motif of OVA contained in F37A with an MHC class I epitope motif of WT1 (left), and a graph showing the results of evaluation of the antigen-presenting capacity of each mutant based on the level of IL-2 production (right). Panel (d) shows the results of a cross-presentation assay.

FIG. 6 shows the amino acid sequences of artificial proteins and mutants prepared by replacement with an MHC class I epitope motif of WT1.

FIG. 7 shows the results of investigation of the secondary structures of artificial proteins by circular dichroism (CD) analysis.

MODE FOR CARRYING OUT THE INVENTION

Figure 8:
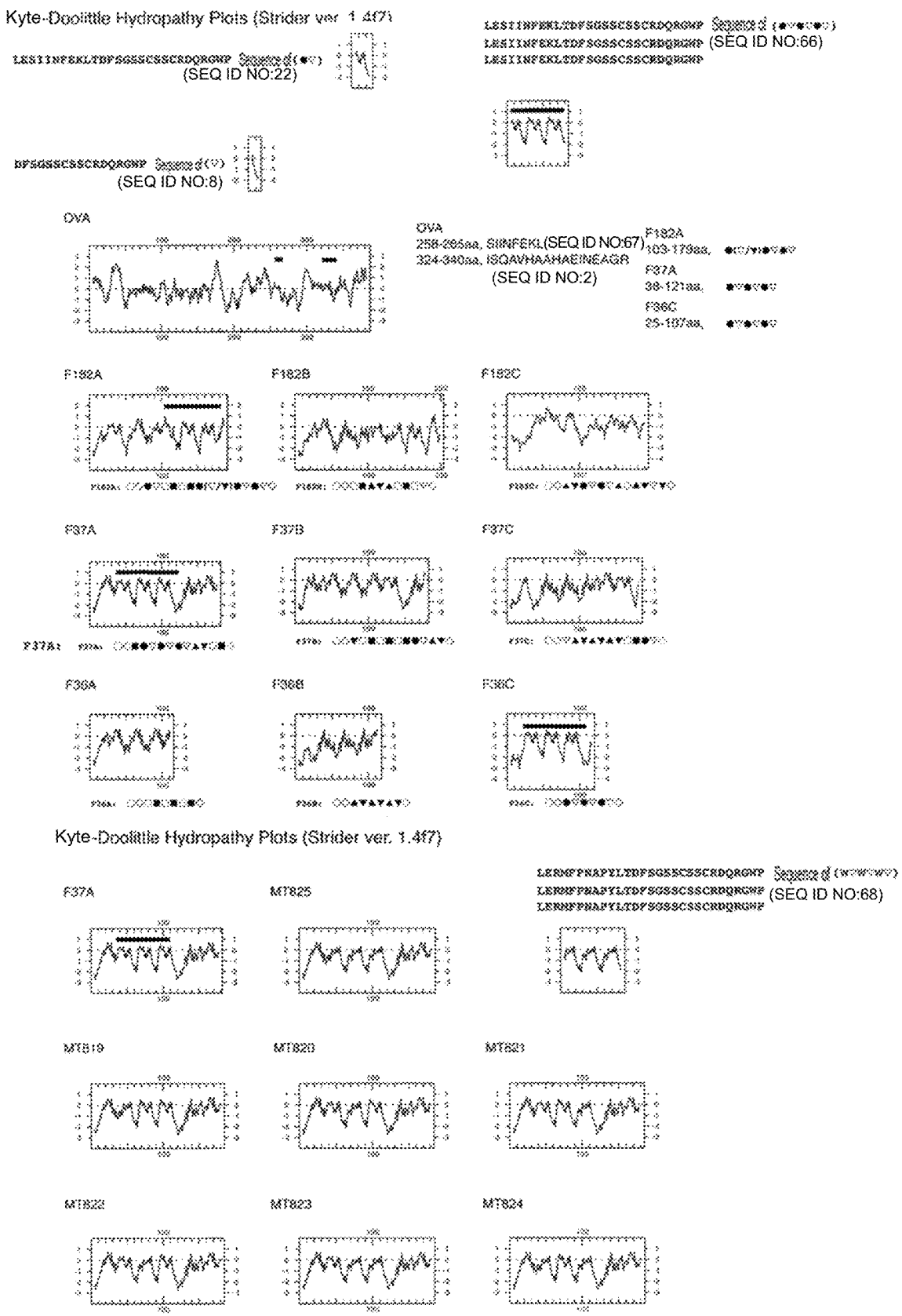
FIG. 8 shows the results of Hydropathy (Kyte-Doolittle) hydrophobicity analysis of artificial proteins using Strider 1.4f7 software.

The polypeptide used as an effective component in the present invention is an artificial protein which is not naturally present. The effective component polypeptide is characterized in that it comprises a tandem repeat structure in which one MHC class I epitope region and one spacer sequence are linked to each other alternately and repeatedly at least three times, wherein each of the MHC class I epitope region is derived from an antigen protein and each of the spacer sequence is as defined in the present description. Thanks to the structure comprising at least three repeats each of which comprises a class I epitope region and a spacer sequence, the polypeptide can strongly induce cell-mediated immunity against the subject antigen protein. Usually, in the case of peptide vaccines containing a polypeptide as an effective component, use of a certain amount of aluminum adjuvant or oil adjuvant is indispensable for induction of sufficient immunity in vivo. However, the peptide vaccine of the present invention can exhibit a sufficiently high immune-inducing capacity while reducing the amount of the aluminum adjuvant or the oil adjuvant and hence reducing side effects, or while using none of such adjuvants.

The "MHC class I epitope derived from an antigen protein" and the "MHC class II epitope derived from an antigen protein" include not only epitopes whose amino acid sequences are the same as those of the corresponding epitopes found in native antigen proteins, but also epitopes whose amino acid sequences are the same as the native epitope sequences except that small numbers of residues are modified. It is known that modification of the sequence of a native MHC class I epitope or class II epitope increases its epitope functions such as the binding capacity to MHC class I or class II molecules. For example, it is known that, in the MHC class I epitope CMTWNQMNL in the tumor antigen WT1, substitution of the second M to Y increases the binding capacity of the epitope to MHC class I molecules (Cancer Immunol Immunother (2002) 51: 614-620). Such a modified MHC class I or class II epitope is also included in the "MHC class I epitope derived from an antigen protein" or the "MHC class II epitope derived from an antigen protein".

The tandem repeat structure is a structure comprising at least three units linked to each other, wherein each unit is composed of an MHC class I epitope region and a spacer sequence. Although the upper limit of the number of the repeats is not limited, the size of the effective component polypeptide is preferably not more than about 500 residues from the viewpoint of the vaccine production cost and the like. In cases where the polynucleotide encoding the effective component polypeptide is obtained by polymerization of microgenes by the later-mentioned MPR method, the size of the polypeptide encoded usually becomes not more than about 300 residues due to the general upper limit of the size of the microgene polymer in the MPR method. Thus, the number of the repeats in the tandem repeat structure is usually not more than about 10.

In the tandem repeat structure, not more than several, preferably not more than 5, more preferably not more than 3 residues may be inserted in a part of the motif-linking portions, and/or not more than several, preferably not more than 5, more preferably not more than 3 residues may be deleted in a part of the motif-linking portions. Such modification of residues in the motif-linking portions inevitably occurs due to the nature of the MPR method. The MHC class I epitope region may contain, as described below, a small number of the adjacent residues derived from the original antigen protein at the end(s) of the minimal epitope sequence, and such residues that may be contained in the class I epitope region besides the minimal epitope sequence may be deleted in a part of the repeat units, as long as the minimal epitope sequences are maintained in the tandem repeat structure.

It is not necessary that all the spacer sequence motifs in the tandem repeat structure should be completely identical, and the tandem repeat structure may also comprise a spacer sequence motif(s) having not more than several, preferably not more than 6 nonidentical residues. In cases where the effective component polypeptide is obtained from an artificial protein library prepared by polymerization of microgenes by the MPR method, a motif sequence not identical to the motif sequence originally defined by the microgene is often generated due to a random reading frame shift during the polymerization reaction process. The spacer sequence in the present invention may be composed of a sequence generated in such a manner, in which sequence a part of the residues (preferably not more than 6 residues) are different from those in the spacer sequence(s) found in other repeat unit(s).

The spacer sequence used in the present invention is a sequence generated as an amino acid sequence inevitably encoded by a single base sequence which is designed such that an MHC class I epitope region derived from an antigen protein, an MHC class II epitope region derived from the same or a different antigen protein mentioned above, and at least one higher-order-structure-stabilizing region are encoded by different reading frames of the single base sequence. Preferably, the amino acid sequence of the spacer sequence is a sequence generated by the same reading frame as the reading frame for the class I epitope region, which sequence occurs adjacent to the class I epitope region. Such a base sequence designed such that a plurality of motifs are encoded by different reading frames and such that no stop codon occurs in any of the reading frames is sometimes called a multifunctional base sequence or a microgene. When the amino acid sequences encoded by two out of the three reading frames are determined, the amino acid sequence in the remaining frame is automatically determined.

Or, the spacer sequence used in the present invention has the same sequence as the amino acid sequence automatically determined as described above except that a region composed of several amino acid residues is replaced. More specifically, the spacer sequence may be a sequence in which a region of several amino acid residues is replaced with an amino acid sequence derived from a part of the MHC class II epitope region or the higher-order-structure-stabilizing region encoded by another reading frame. In cases where a polypeptide is prepared from a microgene polymer prepared by the MPR method, insertion and/or deletion of a base(s) often randomly occur(s) in a linking portion(s) of the microgenes due to the exonuclease activity of the polymerase, resulting in generation of a motif sequence which is partially replaced with an amino acid sequence derived from a motif sequence in another reading frame. In the following Examples, the tandem repeat structure of the artificial protein F182A contains such a partially replaced spacer sequence. It should be noted, however, that in some cases a tandem repeat structure in which none of the spacer sequences has such a replaced sequence may give the polypeptide a higher capacity to induce cell-mediated immunity.

The MHC class I epitope and the MHC class II epitope may be derived from the same antigen protein, or may be derived from different antigen proteins. Typically, the MHC class I epitope and the MHC class II epitope may be derived from the same antigen. Epitope sequences capable of binding to a plurality of MHC class II molecules are known (e.g., the pan HLA-DR-binding epitope, which is called the PADRE epitope; see, for example, Hum Immunol. 2012 January 73(1): 1-10. and Molecular Therapy vol. 15 no. 6, 1211-1219 June 2007). In cases where a class I epitope and a class II epitope derived from different antigen proteins are used, such an epitope which can bind to a plurality of MHC class II molecules may be used. Specific examples of the effective component polypeptide using a PADRE epitope include the sequences of SEQ ID NOs: 61 and 62 in SEQUENCE LISTING (see Tables 1 and 2 below).

In the present invention, the multifunctional base sequence may be designed such that a total of six motifs are encoded in the three reading frames and such that no stop codon is contained in any of the three reading frames (see FIG. 2). Among the six motifs, one motif corresponds to an MHC class I epitope region; one motif corresponds to an MHC class II epitope region; and two motifs correspond to higher-order-structure-stabilizing regions. Usually, in such cases, a multifunctional base sequence (I) encoding an MHC class I epitope region and a multifunctional base sequence (II) encoding an MHC class II epitope region are separately designed, and these two multifunctional base sequences are linked to each other while adjusting the reading frames. By this, a single multifunctional base sequence (microgene) in which the class I epitope, the class II epitope, and at least one higher-order-structure-stabilizing region are encoded by different reading frames is designed. When the amino acid sequences of two reading frames in a multifunctional base sequence are determined and the remaining reading frame is designed such that no stop codon is generated therein, the amino acid sequence of this remaining reading frame is automatically determined. Accordingly, one automatically determined sequence motif for the class I epitope in the multifunctional gene (I) and one automatically determined sequence motif for the class II epitope in the multifunctional gene (II) are obtained. In the microgene sequence after the linking, the two higher-order-structure-stabilizing region motifs may be placed in the same reading frame, or in different reading frames. However, since the microgene sequence is designed such that the class I epitope and the class II epitope are not placed in the same reading frame, the automatically determined sequence motifs are not encoded in the same reading frame. Among the thus obtained automatically determined or inevitably generated sequence motifs, the sequence motif generated for the class II epitope, which occurs adjacent to the class I epitope region in the same reading frame as the reading frame for the class I epitope in the microgene, is used as the spacer sequence in the tandem repeat structure.

The "higher-order-structure-stabilizing region" is a region having a sequence that allows a polypeptide to have a stable higher-order structure when the polypeptide is expressed from a nucleic acid polymer obtained by polymerization of multifunctional base sequences. The higher-order structure of a polypeptide is stabilized by formation of an α-helix structure(s), β-sheet structure(s), intramolecular hydrophobic bond(s), and/or the like. Specific examples of the higher-order-structure-stabilizing region include an α-helix-forming region (amino acid sequence region which tends to form an α-helix structure(s)), β-sheet-forming region (amino acid sequence region which tends to form a β-sheet structure(s)), and hydrophobic-bond-forming region (region which is rich in amino acid residues having a hydrophobic side chain and tends to form an intramolecular hydrophobic bond(s)). It is known that a protein can have a stable higher-order structure by having such structures. The higher-order-structure-stabilizing region is preferably at least one selected from an α-helix-forming region and a β-sheet-forming region, more preferably an α-helix-forming region. It is known that, among amino acid residues, there are residues that tend to form an α-helix and residues that tend to form a β-sheet. The α-helix-forming region and the β-sheet-forming region may be constituted using such residues The multifunctional base sequence (microgene) is preferably designed such that, among the three reading frames, the MHC class I epitope region is encoded in one reading frame; the MHC class II epitope region is encoded in another reading frame; and the at least one α-helix-forming region is encoded in the other reading frame. As described above, the spacer sequence is an amino acid sequence motif which occurs adjacent to the MHC class I epitope region in the reading frame encoding the MHC class I epitope region. For example, if the MHC class I epitope region is encoded in the first frame, the MHC class II epitope region is encoded in the second frame (the reading frame which occurs by one-base shift from the first frame in the 3'-direction), and one or two α-helix-forming regions are encoded in the third frame (the reading frame which occurs by two-base shift from the first frame in the 3'-direction), then the amino acid sequence generated in the first frame may be used as the spacer sequence.

In general, MHC class I epitopes retained by antigen proteins have a size of about 5 to 12 residues, typically about 8 to 10 residues. Although it is known that the lengths of MHC class II epitopes are not strictly limited, MHC class II epitopes mostly have a size of 13 to 30 residues, and a class II epitope having a size of about 13 to 23 residues may be preferably used as the class II epitope region motif in the present invention. Therefore, for example, if a multifunctional base sequence is designed such that the class I epitope is encoded in the first reading frame, the class II epitope is encoded in the second reading frame, and the at least one higher-order-structure-stabilizing region is encoded in the third reading frame, then the multifunctional base sequence usually has a size of about 30 bp to 90 bp, and the spacer sequence obtained has a size of about 10 to 30 residues.

The "MHC class I epitope region" may contain not only the minimal unit of the MHC class I epitope derived from an antigen protein, but also several (for example, one to three) residues adjacent to each side of the epitope in the amino acid sequence of the original antigen protein. Usually, it is preferred to add at least two amino acid residues derived from the amino acid sequence of the original antigen protein to the N-terminus of the minimal sequence of the MHC class I epitope, and at least one such amino acid residue to the C-terminus, and to use the resulting amino acid sequence as the MHC class I epitope region motif. More specifically, for example, when the antigen protein sequence is . . . abcdXXXXXXXXefgh . . . wherein XXXXXXXX represents a class I epitope, cdXXXXXXXe obtained by adding the N-terminal side "cd" and the C-terminal side "e" to the epitope may be used as the MHC class I epitope region motif. It is known that the C-terminal side of the epitope is cleaved by proteasome with relatively low sequence specificity, while the N-terminal side is cleaved by sequence-specific aminopeptidase. By also maintaining, in the effective component polypeptide molecule, the structures in both sides of the epitope in the original antigen protein as described above, antigen presentation can be allowed to occur more efficiently, and the capacity to induce cell-mediated immunity can be further increased. The same applies to the MHC class II epitope region.

The sequences of MHC class I epitopes and MHC class II epitopes in various antigen proteins have been identified, and are known. Further, since algorithms for prediction of epitopes from amino acid sequence information are known (for example, SYFPEITHI algorithm software), such algorithms may be applied to an arbitrary antigen protein for predicting epitopes that bind to MHC molecules, and the predicted epitopes may be used as the MHC class I and class II epitopes. Further, as described above, it is known that partial modification of native MHC class I and class II epitopes allows enhancement of their epitope functions (for example, the binding capacity to MHC class I molecules or class II molecules). In the present invention, such a modified epitope sequence may also be used.

The spacer sequence obtained for an MHC class I epitope or class II epitope as described above may contain a large number of hydrophilic amino acids (e.g. R, N, D, E, Q, G, H, K, P, S, T, Y) and have a hydrophilic property. Whether the spacer sequence is hydrophilic or not can be investigated by Hydropathy (Kyte-Doolittle) analysis using Strider 1.4f7 software.

The amphipathicity of the tandem repeat structure portion may be 0.0 to 0.4. An amphipathicity analysis can be carried out using Strider 1.47 software.

The polypeptide containing the tandem repeat structure described above, which is used as an effective component, may contain an MHC class II epitope region derived from the same antigen protein in at least one of the N-terminal region and the C-terminal region. By this, the capacity of the vaccine to induce cell-mediated immunity can be further increased.

The effective component polypeptide may contain the higher-order-structure-stabilizing region as defined above. By the inclusion of the region which stabilizes a higher-order structure such as an α-helix structure or a β-sheet structure, the stability of the polypeptide increases, and the production efficiency in host cells such as *E. coli* can be increased.

The effective component polypeptide may also contain a tag sequence such as a histidine tag for, e.g., convenience in production of the polypeptide.

The effective component polypeptide may have an isoelectric point (pI) of 6.0 to 8.6. For adjusting the isoelectric point of the polypeptide to such a nearly neutral value, a sequence such as DYKDHDGDYKDHDIDYKDDDDKL (SEQ ID NO: 69, triple FLAG tag sequence) or DEDEDED (SEQ ID NO:70) may be introduced to the effective component polypeptide, if necessary. Specific examples of effective component polypeptides in which such sequences are introduced are shown in SEQ ID NOs:57 to 60 in SEQUENCE LISTING (see Table 1-1 below).

Methods for designing a multifunctional base sequence is known. For example, CyberGene software described in K. Shiba, Journal of Molecular Catalysis B: Enzymatic 28 (2004) 145-153 may be employed therefor. More specifically, multifunctional base sequences can be designed by the designing methods described in, for example, JP 4007477 B, JP 4911857 B, and JP 4989600 B. Any of these methods may be used in the present invention.

JP 4007477 B is a designing method that is carried out by a process in which a peptide sequence given a first function (the MHC class I epitope peptide sequence and class II epitope peptide sequence, in the case of the present application) is set as an initial value, and reverse translation is performed based on the genetic codon table in a base-by-base manner to generate all possible base sequences encoding the peptide sequence in a computer, followed by writing the peptide sequence population encoded by all generated base sequences in the reading frames other than the reading frame of the first peptide sequence in the computer, and then selecting peptides having second and third functions from the peptide sequence population. In this method, the protein to be encoded by the multifunctional base sequence is analyzed as a linked product of 20 kinds of amino acids.

The designing methods described in JP 4911857 B and JP 4989600 B are improved methods of the designing method described in JP 4007477 B. In these methods, the protein to be encoded by the multifunctional base sequence is analyzed as an overlapping/linked product of very short peptide sequences of about two to eight residues rather than a linked product of 20 kinds of amino acids. The base sequence encoding a dipeptide is composed of six bases, and the six bases already have the information on the translation products in the second and the third reading frames. Therefore, by performing analysis and calculation for the protein as an overlapping/linked product of very short peptide sequences of about two to eight residues, base sequences containing a stop codon(s) in the middle of the second frame and/or the third frame can be eliminated before the computation. By this, the computation time and the memory size required can be largely reduced relative to the method in which the protein is analyzed as a linked product of 20 kinds of amino acids.

Figure 1:
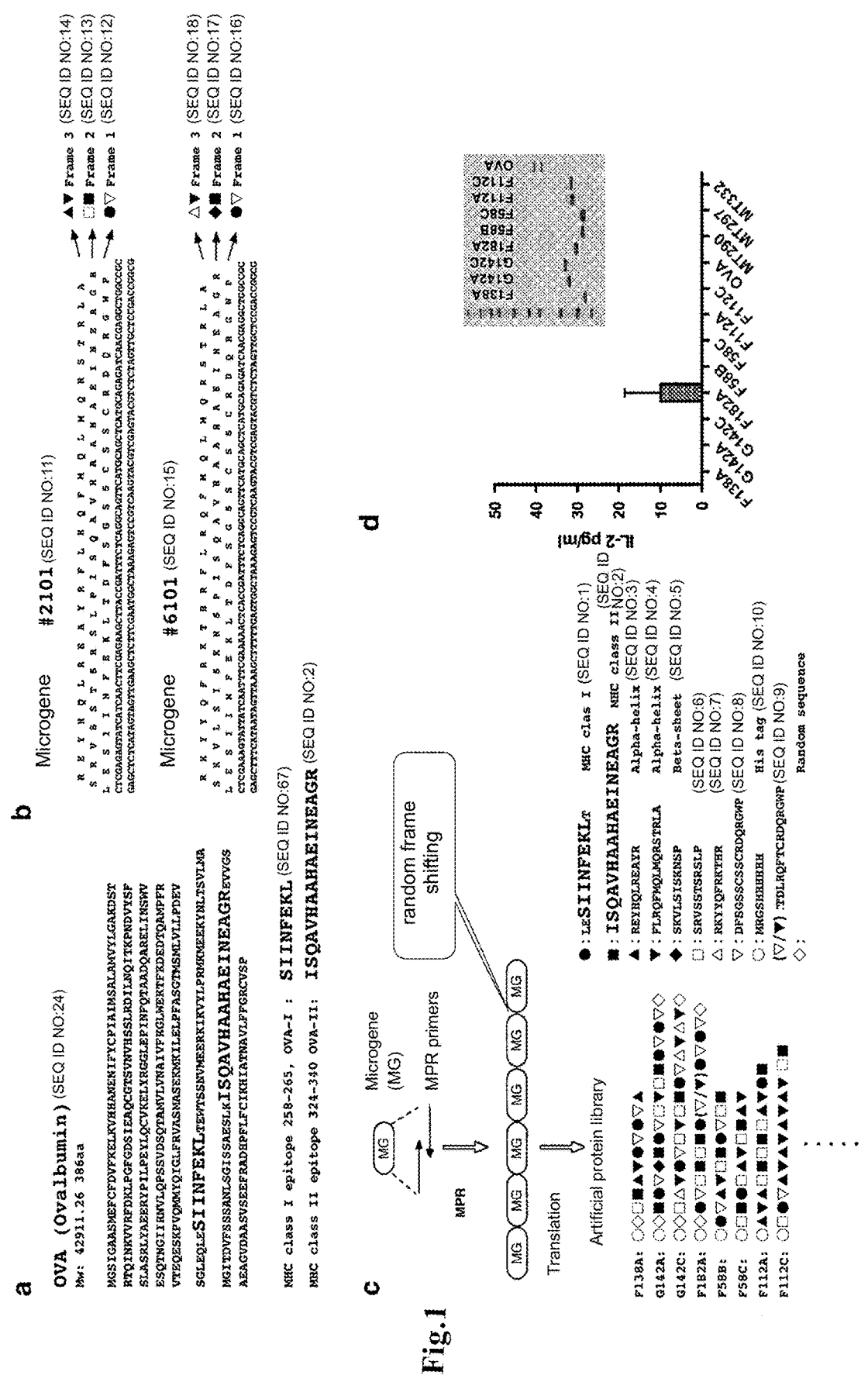

In the Examples below, multifunctional base sequences (microgenes) were designed using CyberGene software, and a population of microgene polymers (artificial protein genes) was constructed by a known microgene polymerization method (microgene polymerization reaction, MPR; Kiyotaka Shiba et al., PNAS vol. 94, pp. 3805-3810, 1997). Proteins were then expressed from these polymers to obtain proteins having a high antigen-presenting capacity (FIGS. 1 and 2). Such a method is known as the MOLCRAFT® method (K. Shiba, Journal of Molecular Catalysis B: Enzymatic 28 (2004) 145-153), and various artificial proteins have been synthesized by this method (for example, Saito et al., Chemistry & Biology, Vol. 11, 765-773, 2004; Saito et al., Nucleic Acids Research, 2007, Vol. 35, No. 6, e38; and Kokubun et al., Biomacromolecules 2008, 9, 3098-3105). By using the MOLCRAFT® method, the polypeptide sequence to be used for the vaccine of the present invention can be obtained for various antigen proteins.

A method for producing an anti-cancer vaccine according to the present invention using MHC class I and class II epitope sequences derived from the WT1 protein is described below.

In the WT1 protein (SEQ ID NO:23), as MHC class I epitopes, CMTWNQMNL (SEQ ID NO: 71, residues at positions 303 to 311 in SEQ ID NO:23) and RMFPNAPYL (SEQ ID NO: 72, residues at positions 194 to 202 in SEQ ID NO:23), and their modified sequences (for example, the sequence obtained by replacing the second M of CMTWNQMNL (SEQ ID NO: 71) with Y; Cancer Immunol Immunother (2002) 51: 614-620) may be used. In the present case, RMFPNAPYL (SEQ ID NO: 72) is employed. RMFPNAPYL (SEQ ID NO: 72) is used for designing multifunctional base sequences with addition of several amino acid residues which are adjacent thereto in both sides in the original WT1 protein (for example, addition of QA, which is adjacent in the N-terminal side, and P, which is adjacent in the C-terminal side, to the corresponding termini). As the MHC class II epitope, PGCNKRYFKLSHLQMHSRKHTG (SEQ ID NO: 73, residues at positions 396 to 417 in SEQ ID NO:23) may be used. Briefly, the procedure is as follows: a multifunctional base sequence encoding the class I epitope and a multifunctional base sequence encoding the class II epitope are separately designed, and the resulting two multifunctional base sequences are fused with each other for designing a microgene, followed by designing MPR primers based on the sequence of this microgene and performing microgene polymerization reaction by the MPR method.

First, in a computer, each of QARMFPNAPYLP (SEQ ID NO: 74) and PGCNKRYFKLSHLQMHSRKHTG (SEQ ID NO: 73) is set as an initial value (first sequence). Reverse translation into base sequences is then performed based on the genetic codon table in a base-by-base manner to generate all possible base sequences encoding the peptide sequence in the computer. Subsequently, from the base sequences encoding QARMFPNAPYLP (SEQ ID NO: 74) and the base sequences encoding PGCNKRYFKLSHLQMHSRKHTG (SEQ ID NO: 73), sequences encoding a higher-order-structure-stabilizing region in another reading frame are selected (second sequences) for each first sequence. In cases where CyberGene software is used, when QARMFPNAPYLP (SEQ ID NO: 74) and PGCNKRYFKLSHLQMHSRKHTG (SEQ ID NO: 73) are fed as first sequences, a number of sequence candidates that tend to form an α-helix structure and/or β-sheet structure are described. Hence, sequences which tend to have a stable structure may be selected therefrom as the second sequences. Simple reverse translation of the first-sequence motifs produces a vast number of combinations of DNA sequences. However, since the CyberGene program is designed such that cases where identical motif sequences are generated in a plurality of reading frames and cases where a stop codon(s) is/are generated in any of the reading frames are eliminated, the number of candidates for the multifunctional base sequences obtained from the motif sequences fed is much smaller than the theoretical number of the combinations. By assigning a first sequence and a second sequence, the third sequence can be automatically determined. Hundreds or more of multifunctional base sequences each of which encodes an epitope motif in one reading frame and a higher-order-structure-stabilizing motif in one of the other reading frames are output. These sequences are ranked based on the tendency to forma structure. About 10 top-ranked sequences are selected from those sequences.

By linking a multifunctional sequence (I) encoding QARMFPNAPYLP (SEQ ID NO: 74) in the first frame and a multifunctional sequence (II) encoding PGCNKRYFKLSHLQMHSRKHTG (SEQ ID NO: 73) in the first frame obtained as described above to each other, a microgene sequence encoding the MHC class I epitope and class II epitope of WT1, and at least one higher-order-structure-stabilizing region, in different reading frames is obtained. Among the candidate sequences, sequences in which no stop codon is generated even in cases where the frame is shifted are selected, and adjustment of the sequences is carried out. In this process, the linking site is appropriately adjusted such that the MHC class I motif QARMFPNAPYLP (SEQ ID NO: 74) and the MHC class II motif PGCNKRYFKLSHLQMHSRKHTG (SEQ ID NO: 73) are not placed in the same reading frame. A third sequences, which are automatically determined and have no given function, occur for the class I motif QARMFPNAPYLP (SEQ ID NO: 74) and the class II motif PGCNKRYFKLSHLQMHSRKHTG (SEQ ID NO: 73), respectively. As a result of the linking of the multifunctional base sequences (I) and (II) to each other such that the MHC class I motif and the MHC class II motif are not placed in the same reading frame, the third sequence generated for the class II motif is placed in the same reading frame as that of the MHC class I motif. Accordingly, the spacer sequence in the present invention can be understood as follows. That is, when a multifunctional base sequence is designed such that an MHC class II epitope region (epitope derived from the same antigen as the antigen from which the class I epitope employed for the polypeptide is derived) and a higher-order-structure-stabilizing region(s) are encoded by different reading frames, a certain amino acid sequence is encoded by the remaining reading frame, which sequence is the spacer sequence in the present invention.

By the process described above, a spacer sequence for the polypeptide to be used as an effective component in the present invention can be obtained. This spacer sequence may be linked to the MHC class I motif QARMFPNAPYLP (SEQ ID NO: 74), and a tandem repeat structure of the resulting sequence may be constructed for designing the effective-component polypeptide. Or, microgenes may be polymerized while allowing random frame shifts to occur by the MPR method, and proteins may be expressed from the resulting polymers (artificial protein genes). Thereafter, proteins containing a structure in which the class I epitope and the spacer sequence are linked tandemly and repeatedly three times or more may be selected, and their capacities to induce cell-mediated immunity may be investigated.

The MPR primers used in the MPR method are designed such that the sense primer and the antisense primer form complementary base pairs of several bases (usually about eight bases) in the 3'-end region of each of the primers. However, a mismatch is provided for the 3'-end base. In the polymerization reaction using the MPR primers, the primers anneal to each other in a part of the 3'-side region of each primer, and, as a result, complementary strands are synthesized for the single-stranded portions by the polymerization reaction. In the MPR method, the primers themselves also act as templates. Each MPR primer may be used at a concentration of about 40 nM to 2000 nM. By performing two-step reaction cycles using a thermal cycler, the microgenes are tandemly linked to each other and thus a microgene polymer is synthesized. As the polymerase, a DNA polymerase having 3'→5' exonuclease activity is used. During the polymerization reaction process, fluctuation occurs in the linking portions of the microgenes, randomly causing deletion and/or insertion of a base(s). This causes shifts of the reading frame, leading to creation of a library of artificial genes which produces the encoded polypeptide sequences in various numbers and various combinations.

The thus obtained genes are incorporated into an appropriate protein expression vector by a well-known conventional method. By allowing expression of the proteins, an artificial protein library can be obtained. A His-tag fusion protein expression vector may be used for introduction of the genes into appropriate host cells such as E. coli or insect cells, and the expressed proteins may be purified by a conventional method using the His-tag. Since the expression efficiency in the host cells varies among the artificial genes, the amount of protein purified also needs to be evaluated for preparation of the artificial protein library.

The artificial proteins expressed from the artificial genes may be evaluated by conventional methods for their antigen-presenting capacities and capacities to induce cell-mediated immunity. Artificial genes encoding artificial proteins having a structure in which the class I epitope motif and the spacer sequence obtained by the design of the multifunctional base sequence are linked to each other tandemly and repeatedly three times or more may be selected, and the selected artificial genes may be evaluated for the antigen-presenting capacities and capacities to induce cell-mediated immunity.

For example, in the evaluation of the antigen-presenting capacity, each obtained artificial protein may be added to antigen-presenting cells, and presentation of the epitope of interest on MHC class I or class II molecules may be measured in vitro using epitope-specific CD8+ T cells or the like. In a method in which the presentation capacity of the class I epitope is evaluated using epitope-specific CD8+ T cells, CD8+ T cells having T cell receptors (TCRs) specific to the class I epitope are co-cultured with antigen-presenting cells to which the artificial protein is added. After incorporation and processing of the artificial protein followed by presentation of the epitope on MHC class I molecules, CD8+ T cells recognize the epitope via TCRs, and produce IL-2 specifically to the antigen. By selecting artificial proteins which cause high production of the IL-2, artificial proteins which cause antigen presentation via cross-presentation can be screened.

Taking into account the in vitro antigen-presenting capacity, the amount of protein purified, and the like, artificial proteins having a high capacity to induce CD8+ cytotoxic T cells (capacity to induce cell-mediated immunity) in vivo can be selected by a conventional method. For example, animals such as mice (excluding human) are immunized by intracutaneous, subcutaneous, intraperitoneal, or another mode of administration of about 100 µg of each candidate artificial protein together with 20 µg of adjuvant MPL (monophosphoryl lipid A) at least once, preferably about three times at two-week intervals. Thereafter, spleen cells may be removed and subjected to a tetramer assay by flow cytometry using a tetramer reagent for detection of CD8+ T cells having epitope-specific TCRs, to evaluate the capacity of each protein to induce CD8+ cytotoxic T cells. Or, selection of artificial proteins having high cytotoxicity may also be carried out by performing a functional cytotoxicity assay using recombinant E.G7 tumor cells which express each antigen protein, and their parent cells, EL-4. Furthermore, E.G7 cells expressing each antigen protein may be inoculated to immunized animals, and then artificial proteins that suppress tumor growth may be selected.

By carrying out the MolCraft method according to the procedure described above, preferred examples of the polypeptide to be used as an effective component of the vaccine, comprising a tandem repeat structure in which an MHC class I epitope derived from an arbitrary antigen protein and a spacer sequence according to the definition in the present invention are linked to each other repeatedly three times or more can be obtained. Once the amino acid sequence of the polypeptide and the base sequence of the polynucleotide (artificial gene) encoding the amino acid sequence are specified, the polypeptide can be produced by a method well known in the art. For example, the polynucleotide may be incorporated into an appropriate expression vector, and the polypeptide may then be expressed in host cells such as E. coli or insect cells, followed by recovering and purifying the polypeptide. The polynucleotide itself can be obtained by PCR amplification using, as a template, the artificial gene obtained in the MPR process in the MolCraft method, or can be prepared by chemical synthesis in cases where the sequence of the polynucleotide has been determined. The polypeptide expressed in E. coli cells can be used as an effective component for pharmaceuticals after removing endotoxin by a method such as the Triton X-114 method. The polypeptide whose sequence has been determined can also be chemically synthesized by a conventional method such as the Fmoc method or the tBoc method. The polypeptide obtained by chemical synthesis, as it is or as a long-chain polypeptide prepared by enzymatic linking, may be refolded to form a higher-order structure required for use in the present invention.

The vaccine of the present invention can be produced for various antigen proteins. Vaccines for tumor antigens and cancer stem cell antigens may be provided as anti-cancer vaccines (therapeutic or prophylactic agents for cancer), and vaccines for antigens of pathogens and parasites may be provided as vaccines for prevention and treatment of infections. The present invention can be favorably applied to diseases whose prevention and treatment are significantly dependent on cell-mediated immunity. Specific examples of the tumor antigens include WT1, survivin, survivin-B2, MAGE-A3, MEGE-A4, tyrosinase, gp100, Melan-A, TRP-2, SNRPD1, CDK4, NY-ESO-1, HER2, MUC-1, CD20, and p53. Examples of the cancer stem cell antigens include CD44, CD133, LGR5, and Dclk1. Examples of the viral antigens include constituent proteins of viruses such as hepatitis viruses (HBV, HCV, and the like), human papillomavirus, and human immunodeficiency virus. Examples of the parasite antigens include *Plasmodium* proteins. Using MHC class I epitopes and class II epitopes of these antigens as motifs, vaccines of the present invention can be designed and produced.

As specific examples of the vaccine peptide of the present invention, examples of the amino acid sequences of polypeptides designed for tumor antigen proteins are shown in Tables 1-1 to 1-3 below.

TABLE 1-1

Tumor antigen WT1 (Wilms tumor 1)

WT1-derived MHC class I epitope   CYTWNQMNL (SEQ ID NO: 75)
WT1-derived MHC class I epitope   RMFNAPYL (SEQ ID NO: 72)
WT1-derived MHC class II epitope  KRYFKLSHLQMHSRKH (SEQ ID NO: 76)

α-Helix structure sequence        REYHQLREAYRFLRQFMQLMQRSTRLA
                                  (SEQ ID NO: 14)

Examples of vaccine peptides:

AkiKaze A24 (SEQ ID NO: 54)
MRGSHHHHHHGSVDWGTRLPKRYFKLSHLQMHSRKHGSLECYTWNQMNLGATDFSGSS

CSSCRDQRGWPLECYTWNQMNLGATDFSGSSCSSCRDQRGWPLECYTWNQMNLGATDF

SGSSCSSCRDQRGWPVDLEPREYHQLREAYRFLRQFMQLMQRSTRLAASRVSSTSRSLPKR

YFKLSHLQMHSRKHGD

AkiKaze A2 (SEQ ID NO: 55)
MRGSHHHHHHGSVDWGTRLPKRYFKLSHLQMHSRKHGSVDQARMFPNAPYLPSTDFSGS

SCSSCRDQRGWPQARMFPNAPYLPSTDFSGSSCSSCRDQRGWPQARMFPNAPYLPSTDFS

GSSCSSCRDQRGWPLEPREYHQLREAYRGFLRQFMQLMQRSTRLAASRVSSTSRSLPKRYFK

LSHLQMHSRKHGD

AkiKaze A242 (SEQ ID NO: 56)
MRGSHHHHHHGSVDWGTRLPKRYFKLSHLQMHSRKHGSLECYTWNQMNLGATDFSGSS

CSSCRDQRGWPLECYTWNQMNLGATDFSGSSCSSCRDQRGWPLECYTWNQMNLGATDF

SGSSCSSCRDQRGWPVDQARMFPNAPYLPSTDFSGSSCSSCRDQRGWPQARMFPNAPYLP

STDFSGSSCSSCRDQRGWPQARMFPNAPYLPSTDFSGSSCSSCRDQRGWPLEPREYHQLRE

AYRFLRQFMQLMQRSTRLAASRVSSTSRSLPKRYFKLSHLQMHSRKHGD

WT1 A2 8110 (SEQ ID NO: 57)
MRGSHHHHHHGSVDWGTGSYVQCSLSSFLRNKRYFKLSHLQMHSRKHGSVDQARMFPN

APYLPSTDFSGSSCSSCRDQRGWPQARMFPNAPYLPSTDFSGSSCSSCRDQRGWPQARMFP

NAPYLPSTDFSGSSCSSCRDQRGWPLERLAVCSMLLIFLLAEQALLQALALADALAEAGSY

VQCSLSSFLRNKRYFKLSHLQMHSRKHVDDYKDHDGDYKDHDIDYKDDDDKLVDKLLES

IINFEKLTDKLGD

WT1 A24 8112 (SEQ ID NO: 58)
MRGSHHHHHHGSVDWGTGSYVQCSLSSFLRNKRYFKLSHLQMHSRKHGSLECYTWNQM

NLGAGTSVTSSSRTCRCTRGSTLECYTWNQMNLGAGTSVTSSSRTCRCTRGSTLECYTWN

QMNLGAGTSVTSSSRTCRCTRGSTVDLERLAVCSMLLIFLLAEQALLQALALADALAEAGS

YVQCSLSSFLRNKRYFKLSHLQMHSRKHVDDYKDHDGDYKDHDIDYKDDDDKLVDKLL

ESIINFEKLTDKLGD

WT1 A24 739 (SEQ ID NO: 59)
MRGSHHHHHHGSVDWGTGSYVQCSLSSFLRNKRYFKLSHLQMHSRKHGSLECYTWNQM

NLGATDFSGSSCSSCRDQRGWPLECYTWNQMNLGATDFSGSSCSSCRDQRGWPLECYTW

NQMNLGATDFSGSSCSSCRDQRGWPVDLERLAVCSMLLIFLLAEQALLQALALADALAEA

GSYVQCSLSSFLRNKRYFKLSHLQMHSRKHVDDEDEDEDVDKLLESIINFEKLTDKLGD

WT1 A2 8310 (SEQ ID NO: 60)
MRGSHHHHHHGSVDWGTGSYVQCSLSSFLRNKRYFKLSHLQMHSRKHGSVDQARMFPN

APYLPSTDFSGSSCSSCRDQRGWPQARMFPNAPYLPSTDFSGSSCSSCRDQRGWPQARMFP

TABLE 1-1-continued

NAPYLPSTDFSGSSCSSCRDQRGWPLERLAVCSMLLIFLLAEQALLQALALADALAEAGSY

VQCSLSSFLRNKRYFKLSHLQMHSRKHVDDEDEDEDVDKLLESIINFEKLTDKLGD

TABLE 1-2

| Tumor antigen WT1 (Wilms tumor 1) | |
|---|---|
| WT1-derived MHC class I epitope | CYTWNQMNL (SEQ ID NO: 75) |
| WT1-derived MHC class I epitope | RMFPNAPYL (SEQ ID NO: 72) |
| Pan HLA-DR-binding epitope (PADRE) | AKFVAAWTLKAAA (SEQ ID NO: 77) |
| α-Helix structure sequence | REYHQLREAYRFLRQFMQLMQRSTRLA (SEQ ID NO: 14) |

Examples of vaccine peptides:

His PADRE WT1 A2 (SEQ ID NO: 61)
MRGSHHHHHHGSVDGTRLPAKFVAAWTLKAAAGSVDQARMFPNAPYLPSTDFSGSSCS

SCRDQRGWPQARMFPNAPYLPSTDFSGSSCSSCRDQRGWPQARMFPNAPYLPSTDFSGS

SCSSCRDQRGWPLEPREYHQLREAYRFLRQFMQLMQRSTRLAASRVSSTSRSLPAKFVA

AWTLKAAAGD

His PADRE WT1 A24 (SEQ ID NO: 62)
MRGSHHHHHHGSVDGTRLPAKFVAAWTLKAAAGSLECYTWNQMNLGATDFSGSSCSS

CRDQRGWPLECYTWNQMNLGATDFSGSSCSSCRDQRGWPLECYTWNQMNLGATDFSG

SSCSSCRDQRGWPVDLEPREYHQLREAYRFLRQFMQLMQRSTRLAASRVSSTSRSLPAKF

VAAWTLKAAAGD

TABLE 1-3

| Tumor antigen gp100 | |
|---|---|
| gp100-derived MHC class I epitope | KVPRNQDWL (SEQ ID NO: 78) |
| gp100-derived MHC class II epitope | WNRQLYPEWTEAQRLD (SEQ ID NO: 79) |
| α-Helix structure sequence | REYHQLREAYRFLRQFMQLMQRSTRLA (SEQ ID NO: 14) |

Examples of vaccine peptides:

GP100 7172 (SEQ ID NO: 63)
MRGSHHHHHHGSVDWGTRLPKAWNRQLYPEWTEAQRLDCWGSATKVPRNQDWLGV

TDFSGSSCSSCRDQRGWPATKVPRNQDWLGVTDFSGSSCSSCRDQRGWPATKVPRNQD

WLGVTDFSGSSCSSCRDQRGWPAREYHQLREAYRFLRQFMQLMQRSTRLAASRVSSTSR

SLPKAWNRQLYPEWTEAQRLDCWVDKLGDLG

The administration route of the vaccine of the present invention to the body may be oral administration or parenteral administration. Parenteral administration such as intramuscular administration, subcutaneous administration, intravenous administration, or intraarterial administration is preferred. The dose is appropriately selected depending on the conditions and symptoms of the disease to be prevented/treated, the age and the body weight of the animal to which the vaccine is to be administered, and the like. The effective dose per subject animal per day may be usually 0.1 μg to 500 mg, for example, 1 μg to 100 mg. The vaccine may be administered at one time, or dividedly in several times. For example, the vaccine may be administered dividedly in several times at intervals of several days to several months.

The formulation of the vaccine is not limited. The vaccine may be composed of only the polypeptide, or may be formulated by mixing the polypeptide with a pharmaceutically acceptable additive(s) suitable for each administration route, such as carriers, diluents, and vehicles. Methods of formulation and additives which may be used are well known in the field of formulation of pharmaceuticals. Specific examples of the formulation include oral preparations such as tablets, capsules, granules, powders, and syrups; and parenteral preparations such as inhalants, injection solutions, suppositories, and solutions.

Conventional peptide vaccines need to be administered in combination with a certain amount of oil adjuvant or aluminum adjuvant in order to induce sufficient immunity in vivo. Examples of such adjuvants that are clinically used at present include Alum (aluminum salt), MF59 (oil emulsion), and Montanide (e.g., Montanide ISA 51VG; oil emulsion). It is thought that oil adjuvants and aluminum adjuvants support immunity through, for example, suppression of antigen degradation, induction of inflammatory cells by tissue destruction, and/or maturation of antigen-presenting cells. However, occurrence of inflammatory reaction (stiffness) in the skin due to such adjuvants has been a problem, and it has also been pointed out that induced CTLs accumulate in the site of inoculation of the adjuvant, preventing effective suppression of tumor growth, which is problematic. The vaccine of the present invention can strongly induce cell-mediated immunity while reducing side effects by reducing the usage of such a problematic oil adjuvant or aluminum adjuvant, or without using such adjuvants. The artificial proteins prepared in the Examples below using OVA do not enhance expression of costimulatory molecules (CD80, CD86, and the like) by TLR (Toll-like Receptor) pathway stimulation. In such cases, an adjuvant that stimulates the TLR pathway such as a TLR ligand may be used in combination. The term "used in combination" means that the vaccine and the adjuvant are administered to the subject either at the same time or sequentially. In cases where the vaccine and the adjuvant are administered at the same time, the vaccine may be formulated such that the vaccine further contains the adjuvant. Some peptide sequences that mimic the TLR ligand function have been identified, and known examples of peptide sequences that mimic the TLR-4 ligand function include APPHALS and QEINSSY (PLoS ONE, February 2012, Volume 7, Issue 2, e30839). By introduction of such a peptide sequence into the sequence of the effective component polypeptide, an adjuvant function may also be given to the polypeptide. Thus, modes in which a peptide sequence having an adjuvant function is introduced into the effective component polypeptide are also included in the modes in which the adjuvant is "used in combination". Examples of adjuvants which stimulate the TLR pathway and are clinically used include MPL.

The vaccine of the present invention may be a vaccine containing as an effective component a recombinant vector which comprises a polynucleotide encoding the artificial polypeptide described above and is capable of expressing the polypeptide in vivo. Vaccines in such a form are also called gene vaccines. The polynucleotide may be either DNA or RNA, and is preferably DNA. The vector to be used for production of the gene vaccine is not limited as long as the vector allows expression in cells of the subject animal (preferably in mammalian cells), and may be either a plasmid vector or a viral vector. Any known vector in the field of gene vaccines may be used. The polynucleotide such as DNA or RNA encoding the artificial polypeptide described above can be easily prepared by a conventional method as mentioned above. The incorporation of the polynucleotide into the vector can be carried out using a method well known in the art.

The administration route of the gene vaccine is preferably a parenteral administration route such as intramuscular administration, subcutaneous administration, intravenous administration, or intraarterial administration. The dose may be appropriately selected depending on the type of the antigen and the like, and is usually about 0.1 µg to 100 mg, for example, about 1 µg to 10 mg, in terms of the weight of the gene vaccine per 1-kg body weight.

As methods of using a gene vaccine, in vivo methods, in which the gene vaccine is directly introduced into the body; and ex vivo methods, in which a certain kind of cells are collected from the subject animal, and the gene is then introduced into the cells ex vivo, followed by returning the resulting cells into the body; are known (for example, Nikkei Science, April 1994, p. 20-45; The Pharmaceutical Monthly, 1994, Vol. 36, No. 1, p. 23-48; Experimental Medicine, Extra Edition, 1994, Vol. 12, No. 15). In vivo methods are more preferred.

In cases where the vaccine is administered by an in vivo method, the vaccine may be administered through an appropriate administration route depending on the disease to be treated, symptoms, and the like. The vaccine may be administered by, for example, intravenous, intraarterial, subcutaneous, or intramuscular administration. In cases where the vaccine is administered by an in vivo method, the vaccine may be formulated into a preparation such as a solution. In general, the vaccine is in the form of, for example, an injection solution containing as an effective component DNA encoding the polypeptide of the present invention. If necessary, a conventionally used carrier may be added thereto. In case of a liposome or membrane fusion liposome (Sendai virus (HVJ)-liposome or the like) containing the DNA, the liposome may be formulated into a liposome preparation such as a suspension, frozen preparation, or centrifugally concentrated frozen preparation.

The vaccine of the present invention may be used in combination with other pharmaceutical(s). For example, a vaccine of the present invention designed for a tumor antigen may be used in combination with other anticancer drug(s).

At present, in tumor immunotherapy, immune checkpoint inhibitors are attracting attention (Nature Reviews Cancer 12, 252-264 (April 2012)). In the living body, a system for inhibitory control of excessive immune reaction is present. Molecules expressed in antigen-presenting cells (APCs) and molecules expressed in T cells, for example, PD-L1 and PD-1; CD80 and CTLA4; MHC class I or MHC class II and KIR or LAG3; and GLA9 and TIM3 have been identified so far. By their interaction, a negative signal is transmitted to T cells to cause inhibition of the T-cell reaction. This mechanism is called immune checkpoint.

Administration of a humanized anti-CTAL-4 antibody, anti-PD-L1 antibody, or anti-PD-1 antibody (immune checkpoint inhibitor), which have functions to inhibit the immune checkpoint, shows a drastic therapeutic effect in melanoma and lung cancer (Clin Cancer Res. 2013 Oct. 1; 19(19): 5300-9). It is also reported that a severe autoimmune disease occurs at the same time since breakdown of immune tolerance to self occurs. This fact indicates that tumor immunity that attacks cancer cells is originally established in cancer patients, and suggests that a system in which expression of PD-L1 and production of various cytokines by cancer cells cause negative control of immune checkpoint, resulting in suppression of the tumor immunity, is functioning, and that, as a result, suppression of the growth of tumor cells becomes impossible, leading to progression of the cancer. That is, tumor-bearing patients are in a braked state where tumor immunity is suppressed. It is thought that administration of the immune checkpoint inhibitor leads to releasing of such a brake against tumor immunity, and allows functioning of the tumor immunity that attacks cancer cells, which is originally retained by the patient, leading to production of the antitumor effect. Although no practical evidence has been obtained for the fact that the tumor immunity originally retained by tumor-bearing patients functions to protect against development of cancer, tumor immunotherapy may largely change in the future due to the progress in scientific understanding of, and drastic therapeutic effects of specific inhibitors of, immune checkpoint.

Immune checkpoint inhibitors are assumed to produce immunity against a mutant protein having a mutation called passenger mutation, which mutant protein does not necessarily accumulate in cancer cells since the mutation does not affect the protein function although it causes amino acid substitution, rather than immunity against an antigen which is overexpressed in cancer, or the so-called cancer antigen, which has a driver mutation (mutation which contributes to the growth of cancer cells, such as an amino acid substitution, gene fusion, deletion, or insertion that causes accumulation in cancer cells). That is, antigens targeted by tumor immunity induced by immune checkpoint inhibitors may largely vary among individuals. Although immune checkpoint inhibitors induce strong antitumor immunity, they are not necessarily effective for all patients, and reported to show different effectiveness on different types of cancer.

Taking these facts into account, it is suggested that induction of strong tumor immunity may be achieved, and a stronger antitumor effect may therefore be obtained, by inducing immunity against a tumor antigen using an artificial protein vaccine according to the present invention while controlling the immunosuppressed state of the tumor-bearing patient using an immune checkpoint inhibitor, that is, by using an artificial protein vaccine according to the present invention and an immune checkpoint inhibitor in combination.

EXAMPLES

The present invention is described below more concretely based on Examples. However, the present invention is not limited to the Examples.

1. Design of Microgenes for Creating Artificial Proteins

From native antigen OVA (SEQ ID NO:24), OVA-I: ● (OVA MHC class I epitope, OVA258-265, SIINFEKL; SEQ ID NO: 67) and OVA-II: ■ (OVA MHC class II epitope, OVA324-340, ISQAVHAAHAEINEAGR; SEQ ID NO: 2) were selected (FIG. 1a).

Microgenes #2101 and #6101, in which the MHC class I epitope OVA-I is encoded in the first sequence, and the MHC class II epitope OVA-II is encoded in the second sequence, were designed using CyberGene software, developed by Kiyotaka Shiba et al. (K. Shiba, Journal of Molecular Catalysis B: Enzymatic 28 (2004) 145-153) (FIG. 1b). The designing process is shown in 1) to 5) in FIG. 2. Since the two amino acids adjacent to the N-terminus of the MHC class I epitope (SIINFEKL) in native antigen OVA are known to influence degradation by aminopeptidase in the cell, two amino acids LE derived from the OVA full-length antigen were added to the N-terminus of OVA-I. The one amino acid in the C-terminus was also selected such that T derived from the OVA full-length antigen is conserved (LESIINFEKLT), and used in a motif for designing microgenes.

First, the multifunctional base sequence (I) encoding the OVA-I motif LESIINFEKLT (SEQ ID NO: 1) and the multifunctional base sequence (II) encoding the OVA-II motif ISQAVHAAHAEINEAGR (SEQ ID NO: 2) were separately designed using CyberGene. If possible codons were written out by reverse translation from the OVA-I motif and the OVA-II motif, the combinations of DNA sequences amounted to 248,832 and 169,869,312, respectively, but DNA sequences such as those having a stop codon in any of the reading frames were eliminated by CyberGene. By assigning the OVA-I motif and the OVA-II motif to the first sequences, respectively, and assigning of an amino acid sequence which tends to form an α-helix structure or a β-sheet structure to the second sequence, hundreds or more of gene sequences were assigned to each of the motifs. For each case, sequences having structures with higher stabilities were selected. Examples of multifunctional base sequences (I) and (II) obtained as a result are shown in 4) in FIG. 2.

The resulting multifunctional base sequences (I) and (II) were linked to each other to design microgenes #2101 (SEQ ID NO:11) and #6101 (SEQ ID NO:15). The amino acid sequences encoded by the three reading frames of #2101 are shown in SEQ ID NOs:12 to 14. The first frame (SEQ ID NO:12) encodes the MHC class I epitope; the second frame (SEQ ID NO:13) encodes the MHC class II epitope; and the third frame (SEQ ID NO:14) encodes two α-helix motifs. The amino acid sequences encoded by the three reading frames of #6101 are shown in SEQ ID NOs:16 to 18. The first frame (SEQ ID NO:16) encodes the MHC class I epitope; the second frame (SEQ ID NO:17) encodes the MHC class II epitope and a β-sheet motif; and the third frame (SEQ ID NO:18) encodes an α-helix motif.

2. Creation of Artificial Protein Library Using MolCraft Method

Using the MolCraft method developed by Kiyotaka Shiba et al. (K. Shiba, Journal of Molecular Catalysis B: Enzymatic 28 (2004) 145-153), peptide motif sequences (Table 2) such as the OVA MHC class I and class II epitopes, protein-stabilizing sequences including α-helix, and sequences automatically defined by CyberGene were combinatorially linked to each other to synthesize artificial protein genes. A summary of the process of synthesis of the artificial protein gene using #2101 by the MPR method (Kiyotaka Shiba et al., PNAS vol. 94, pp. 3805-3810, 1997) is shown in 6) to 9) in FIG. 2.

In the polymerization reaction of #2101, 2101-S primer (CTCGAGAGTATCATCAACTTCGAGAAGCTTACC-GATTTCTCAGGCT; SEQ ID NO:19) and 2101-AS primer (GCGGCCAGCCTCGTTGATCTCTGCATGAGCTGCAT-GAACTGCCTGAGAT; SEQ ID NO:20) were used. In the polymerization reaction of #6101, 6101-S primer (CTCGAAAGTATTATCAATTTCGAAAAACTCACC-GATTTCTCAGGCT; SEQ ID NO:21) and 6101-AS primer (having the same sequence as 2101-AS) were used. A total of 50 μL of polymerization reaction solution was prepared such that the reaction solution had the following composition: 2.6 μL of Vent DNA polymerases having 3'→5' exonuclease activity (2 units/μL, NEW ENGLAND BioLabs), 5 μL of 10×ThermoPol Reaction Buffer (NEW ENGLAND BioLabs, 1×ThermoPol Reaction Buffer: Tris-HCl pH 8.8, 10 mM potassium chloride, 10 mM ammonium sulfate, 2 mM magnesium sulfate, and 0.1% Triton X-100), 350 μM dNTP, 400 nM each of MPR primers S and AS (20 pmol each of the primers was used). The polymerization reaction was carried out using a thermal cycler under the following conditions: 94° C. for 10 minutes→60° C. for 10 minutes→30 cycles of (94° C. for 10 seconds→60° C. for 1 minute)→60° C. for 7 minutes→4° C. ∞.

As described above, 134 kinds of artificial protein genes were synthesized, and each gene was cloned into an expression vector. As a result of checking expression of a protein from each of 62 kinds of genes in *E. coli*, 40 kinds of genes were found to show expression of the protein.

TABLE 2

| | | | |
|---|---|---|---|
| ● | LESIINFEKLT | MHC class I | SEQ ID NO: 1 |
| ■ | ISQAVHAAHAEINEAGR | MHC class II | SEQ ID NO: 2 |
| ▲ | REYHQLREAYR | α-helix | SEQ ID NO: 3 |
| ▼ | FLRQFMQLMQRSTRLA | α-helix | SEQ ID NO: 4 |
| ◆ | SKVLSISKNSP | β-sheet | SEQ ID NO: 5 |
| □ | SRVSSTSRSLP | | SEQ ID NO: 6 |
| Δ | RKYYQFRKTHR | | SEQ ID NO: 7 |
| ∇ | DFSGSSCSSCRDQRGWP | | SEQ ID NO: 8 |
| (∇/▼) | DLRQFTCRDQRGWP | | SEQ ID NO: 9 |
| ○ | MRGSHHHHHH | His-tag | SEQ ID NO: 10 |
| ◇ | Other sequences | | |

(∇/▼): Sequence generated by a frame shift which occurred in a middle part of ∇.

3. In Vitro Antigen-Presenting Function Assay

From the library of these artificial proteins, 8 kinds of artificial proteins (F138A, G142A, G142C, F182A, F58B, F58C, F112A, and F112C shown in FIG. 1c) were first selected, and subjected to an in vitro antigen-presenting capacity assay. The amino acid sequences of the artificial proteins are shown in FIGS. 3 and 4, and SEQ ID NOs:26 to 43.

Each artificial protein was added to antigen-presenting cells (DC2.4 dendritic cell line), and co-cultured with T cells (RF33.70) that recognized an OVA-specific epitope, followed by measuring the IL-2 productivity to evaluate the antigen-presenting capacity.

As a result, only clone F182A (SEQ ID NO:26) caused production of IL-2 to show the antigen-presenting capacity at a concentration of 10 μg/ml (FIG. 1d). The size and the purity of the protein were checked by SDS-PAGE (FIG. 1d). Native OVA did not show the antigen-presenting capacity at a concentration of 10 μg/ml. Similar results were obtained in an experiment using bone-marrow-derived dendritic cells, wherein only F182A, among the 8 kinds of artificial proteins, caused production of IL-2 to show the antigen-presenting capacity (data not shown). From these results, F182A artificial protein was found to have a capacity to induce cell-mediated immunity.

4. Artificial Antigen which Shows Antigen-Presenting Capacity, and its Characteristic Amino Acid Sequence 4-1. F37A Artificial Protein Shows 100-Fold Stronger Antigen Presentation than Native OVA Subsequently, from the library, additional 8 kinds of artificial proteins including artificial proteins having a structure similar to that of F182A were selected, and subjected to evaluation of their antigen-presenting capacities in vitro. At an antigen concentration of 10 μg/ml, not only F182A, but also F37A (SEQ ID NO:44) and F36C (SEQ ID NO:31) showed the antigen-presenting capacity. All of F182A, F37A, and F36C, which showed the antigen-presenting capacity, were found to have a common sequence pattern. That is, they had the sequence of ●∇●∇●∇ (a part or all of ∇ may be (∇/▼)). This is a structure in which LESIIN-FEKLTDFSGSSCSSCRDQRGWP (●∇, SEQ ID NO:22) or LESIINFEKLTDLRQFTCRDQRGWP (●(∇/▼), SEQ ID NO:53) is tandemly repeated three times. Such sequences are hereinafter represented as ●∇●∇●∇ including those in which a part or all of ∇ is (∇/▼).

Native OVA did not show the antigen-presenting capacity until the concentration increased to 1000 μg/ml. Thus, F182A, F37A, and F36C were shown to have a 100-fold higher antigen-presenting capacity than OVA.

4-2. Characteristic Sequence Pattern of F37A Acts on Antigen-Presenting Capacity In order to clarify the fact that the sequence ●∇●∇●∇, which is common to the artificial proteins that showed antigen presentation, is important for the antigen presentation, the OVA-I sequences (●) in the F37A sequence were replaced one by one with an MHC class I epitope sequence (RMFPNAPYL, residues at positions 194 to 202 in SEQ ID NO:23) of WT (Wilms tumor 1) to prepare mutants (FIG. 5c). The sequence of WV is shown in SEQ ID NO:25. The amino acid sequences of the artificial proteins are shown in FIG. 6 and SEQ ID NOs:44 to 52.

The antigen-presenting capacities of these proteins were investigated to find that, when even as few as one OVA-I sequence was replaced with the WT sequence, artificial proteins lost their antigen-presenting capacity in antigen-presenting cells which was co-cultured with T-cells (RF33.70) recognizing an OVA-specific epitope. F37AE2 is an artificial protein having the same amino acid sequence as the amino acid sequence of F37A except that the three amino acids in the C-terminus of F37A are replaced with 5 amino acids different therefrom, and contains ●∇●∇●∇ as it is. F37AE2 showed an increase in the IL-2 productivity dependently on the antigen concentration. From these results, it was revealed that the artificial proteins having stronger antigen-presenting capacities than native OVA protein function through the characteristic ●∇●∇●∇ sequence, and that these artificial proteins allow highly efficient presentation of the epitope peptide on MHC class I molecules irrespective of the fact that they are foreign antigens.

Since F37A stably showed high protein productivity in *E. coli*, and had the highest antigen-presenting capacity of the three artificial proteins, F37A was used to carry out the following experiments.

4-3. Circular Dichroism Analysis (CD) (FIG. 7)

Native OVA and artificial proteins containing many α-helix structures (F182C, F37C, and F36B) showed graph patterns indicating typical α-helix structures. On the other hand, F36A and F182B showed graph patterns characterized by random coils.

F182A, F37C, and F36C, which exhibited antigenicity, showed a common, characteristic graph pattern. They were found to have a secondary structure which was thought to contain at least an α-helix structure, although the graph pattern was evidently different from that shown by native OVA protein. Influence of such a secondary structure on the production of antigenicity was suggested.

Table 3 summarizes biochemical characteristics of the artificial proteins used in the experiment, the numbers of the OVA-I: ● and OVA-II: ■ epitope sequences contained in each protein, and the presence/absence of in vitro antigenicity of each protein.

TABLE 3

| Code | Total Residues | M.W.[a] | Isoelectric Point[b] | No. of OVA-I epitope | No. of OVA-II epitope | Uniqe Motif pattern | Antigenecity (in vitro)[c] |
|---|---|---|---|---|---|---|---|
| native OVA | 386 | 42,911 | 5.19 | 1 | 1 | | + |
| OVA-I peptide | 8 | 963 | 5.72 | 1 | 0 | | |
| OVA-II peptide | 17 | 1773 | 6.00 | 0 | 1 | | |
| F182A | 190 | 21,051 | 6.31 | 4 | 2 | ●▽　●(V/▼)●▽●V | + |
| F37A | 181 | 20,313 | 7.17 | 3 | 2 | ●V●V●V | + |
| F36C | 120 | 13,844 | 8.60 | 3 | 0 | ●V●V●V | + |
| F37AE2 | 183 | 20,517 | 7.80 | 3 | 2 | ●V●V●V | + |
| MT819 | 184 | 20,657 | 8.30 | 2 | 2 | ●V●V | − |
| MT820 | 184 | 20,657 | 8.30 | 2 | 2 | ●V　●V | − |
| MT821 | 184 | 20,657 | 8.30 | 2 | 2 | ●V●V | − |
| MT822 | 185 | 20,803 | 8.64 | 1 | 2 | ●V | − |
| MT823 | 185 | 20,803 | 8.64 | 1 | 2 | ●V | − |
| MT824 | 185 | 20,803 | 8.64 | 1 | 2 | ●V | − |
| MT825 | 186 | 20,948 | 8.90 | 0 | 2 | | − |
| F138A | 158 | 17,963 | 8.55 | 2 | 1 | ●V●V | − |
| G142A | 241 | 27,003 | 9.36 | 4 | 3 | ●V　●V　●V●V | − |
| G142C | 243 | 29,034 | 11.32 | 2 | 1 | ●V　●V | − |
| F58B | 163 | 1,250 | 9.20 | 2 | 2 | ●V　●V | − |
| F58C | 166 | 19,390 | 11.21 | 1 | 2 | ●V | − |
| F112A | 207 | 23,613 | 11.16 | 1 | 2 | ●V | − |
| F112C | 211 | 24,985 | 10.74 | 2 | 2 | ●V　●V | − |
| F182B | 202 | 22,832 | 10.73 | 1 | 2 | ●V | − |
| F182C | 194 | 23,900 | 11.11 | 2 | 0 | ●V　●V | − |
| F37B | 182 | 20,505 | 11.24 | 1 | 3 | ●V | − |
| F37C | 182 | 22,060 | 11.24 | 1 | 1 | ●V | − |
| F36A | 115 | 12,066 | 11.00 | 0 | 3 | | − |
| F36B | 117 | 14,469 | 11.65 | 0 | 0 | | − |
| MT290 | 113 | 12,156 | 10.09 | 0 | 0 | | − |
| MT332 | 140 | 16,449 | 11.69 | 0 | 0 | | − |
| MT297 | 104 | 12,251 | 11.90 | 0 | 0 | | − |

[a,b]Calculated from amino acid sequences using http://tw.expasy.org/tools/protparma.html.
[c] Positive was judged by the II-2 production from RF33. 70 cell in vitro antigen presentation assay.

G142A (SEQ ID NO:35) had four MHC class I epitopes and two MHC class II epitopes, but did not show antigenicity. This fact suggests that the presence of many MHC class I epitopes in the protein does not necessarily contribute to the many MHC class I epitopes in the protein does not necessarily contribute to the induction of antigenicity.

Proteins in which the ●▽ sequence is repeated twice such as F138A and G142A did not show antigenicity. All of the proteins that showed antigenicity contained characteristic ●▽●▽●▽. Thus, the characteristic structure formed by repeating of the ●▽ sequence three or more times, found in ●▽●▽●▽, was suggested to be important for the induction of antigenicity.

The ▽ sequence (DFSGSSCSSCRDQRGWP, SEQ ID NO:8) is a sequence proposed as the third sequence by the algorithm of CyberGene software developed by Kiyotaka Shiba et al., when the MHC class II sequence is set as the first sequence, and a sequence that forms an α-helix is set as the second sequence.

All of the proteins that showed antigenicity were found to have isoelectric points of nearly neutral pHs ranging from 6.0 to 8.6. This fact suggests that a neutral isoelectric point is important for antigenicity of the artificial protein.

Using Strider 1.4f7 software, Hydropathy (Kyte-Doolittle) hydrophobicity analysis was carried out with a window setting of 9. As a result, it was shown that the ▽ sequence (DFSGSSCSSCRDQRGWP, SEQ ID NO:8) located downstream of each MHC class I sequence contained a lot of hydrophilic amino acids (e.g., R, N, D, E, Q, G, H, K, P, S, T, and Y) and exhibited hydrophilic characteristics (FIG. 8), suggesting that it is important that the sequence located downstream of each MHC class I sequence in the three repeats of MHC class I has a hydrophilic property.

Figure 9:
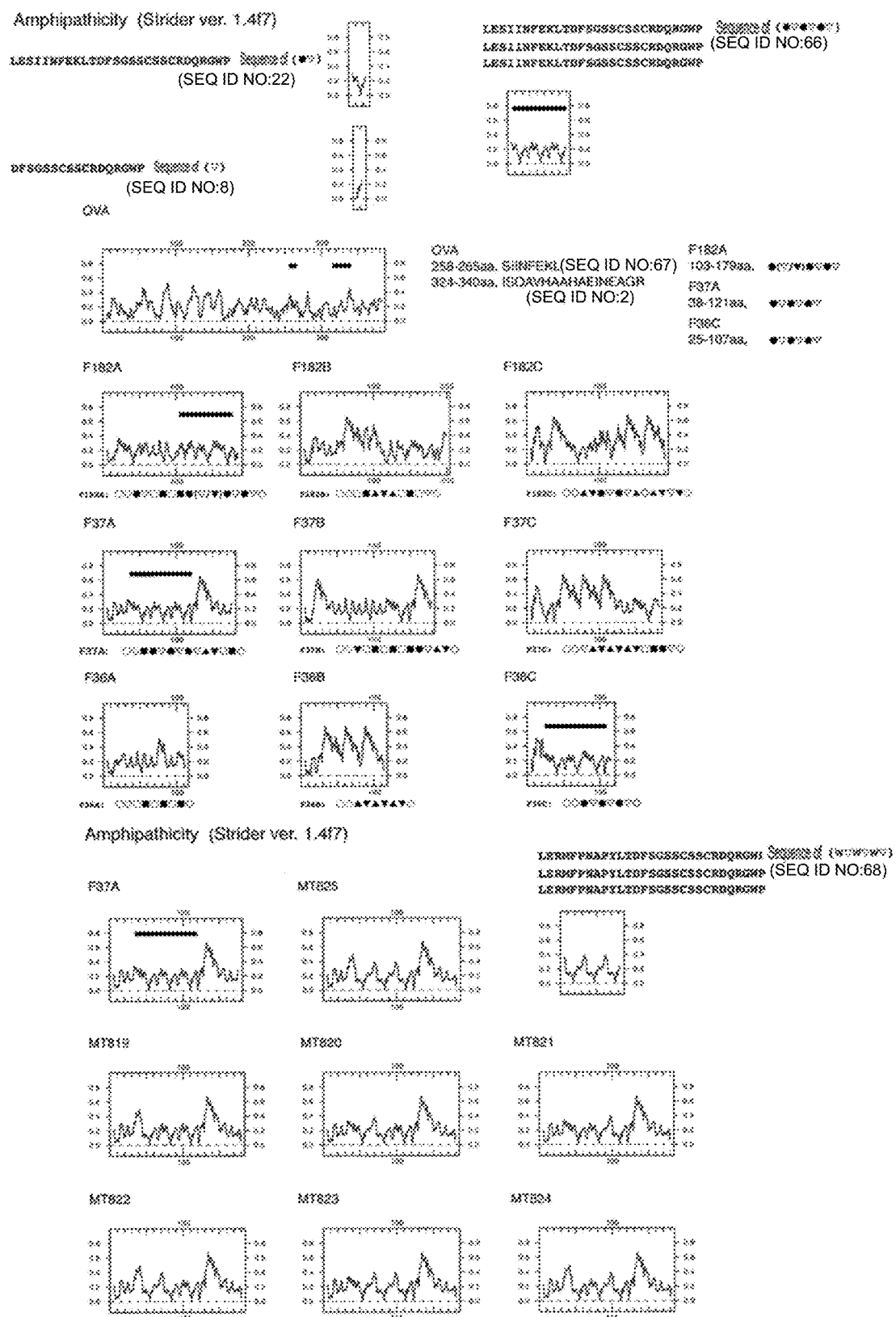
FIG. 9 shows the results of Amphipathicity analysis using Strider 1.4f7 software.

Further, using Strider 1.4f7 software, Amphipathicity analysis of the proteins was carried out with a window setting of 9. As a result, the region of characteristic ●▽●▽●▽ sequence had an amphipathicity between 0.0 and 0.4 (FIG. 9). Thus, it was suggested that such a structure without extreme deviation of amphipathicity is important for the exhibition of antigenicity.

5. F37A Artificial Protein Allows Antigen Presentation Through Cross-Presentation In order to confirm that the artificial proteins are incorporated into antigen-presenting cells and allow antigen-presentation of the epitope through cross-presentation, the proteins were treated with an inhibitor of proteasome involved in cross-presentation, Epoxomicin or MG132, and evaluated for their capacities to induce cell-mediated immunity. As a result, the capacities of F182A and F37A to induce cell-mediated immunity were suppressed (FIG. 5d). Treatment with a lysosome inhibitor (Chloroquine), which has an effect to promote cross-presentation, enhanced the capacities of F182A and F37A to induce cell-mediated immunity.

From these findings, it could be confirmed that F182A and F37A are incorporated into antigen-presenting cells as foreign antigens and undergo proteasomal degradation, followed by presentation of the peptide epitope on MHC class I molecules, that is, the antigen presentation of F182A and F37A occurs through the so-called cross-presentation.

6. F37A does not Exhibit its Antigen-Presenting Capacity Through Maturation of Dendritic Cells It is known that induction of immunity by antigen-presenting cells requires not only antigen presentation on MHC molecules, but also expression of costimulatory molecules (CD80 and CD86), that is, maturation of the antigen-presenting cells. In view of this, F37A was added to BMDCs, bone marrow-derived dendritic cells, induced from mouse bone marrow monocytes using GM-CSF, and expression of the maturation markers CD80 and CD86 was investigated.

Figure 10:
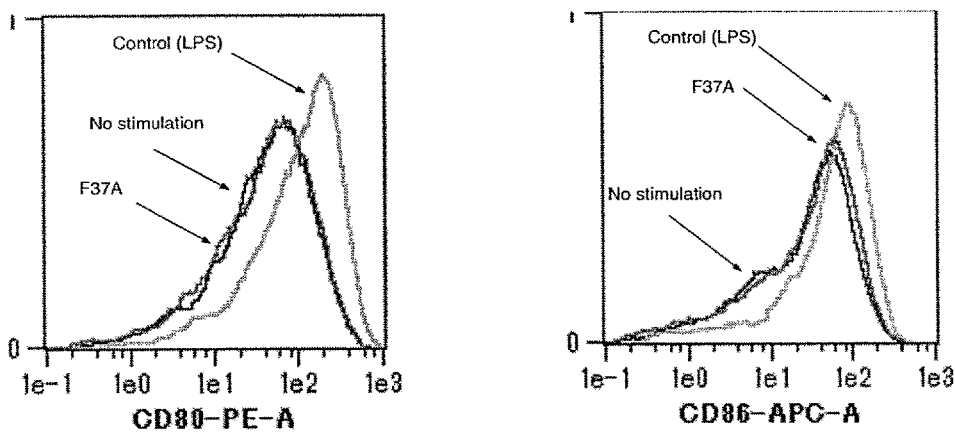
FIG. 10 shows the results of flow cytometric measurement of the expression levels of CD80 and CD86 on the surface of living CD11c$^+$ cells stimulated with F37A for 20 hours.

The results are shown in FIG. 10. F37A did not affect the expression of CD80 and CD86. Thus, it was suggested that F37A does not cause antigen presentation by affecting the maturation of antigen-presenting cells. It should be noted that LPS derived from *E. coli* or from the environment was removed from the artificial protein and OVA using Triton X-114, and that the LPS concentration in the sample was confirmed to be not more than 0.5 EU/mg.

7. F37A Artificial Protein Strongly Induces Cell-Mediated Immunity In Vivo

Subsequently, an antigen was intradermally administered to C57B/6 mice at 100 µg/mouse three times at two-week intervals to perform immunization. As the groups to be studied, an OVA-I peptide group (OVA MHC class I epitope, OVA257-264, SIINFEKL was administered), native OVA protein group, and F37A artificial protein group were set. The immunization was carried out using, as an adjuvant, MPL (monophosphoryl lipid A) or Freund's adjuvant CFA (a complete adjuvant (supplemented with killed tubercle *Bacillus*) was used once, and an incomplete adjuvant was used twice).

Spleen cells were removed from the immunized mice, and subjected to mixed culture in the presence of IL-2 (10 ng/ml) with EG7-OVA cells (OVA-expressing tumor cells) inactivated by 100 Gy X-ray radiation, thereby performing in vitro stimulation. Thereafter, for detection of functional OVA-specific T cells, a Cromium-51 releasing assay (cytotoxicity assay) targeting EL-4 (cells not expressing OVA, corresponding to parent cells of E.G7-OVA) and EG7-OVA cells (cells expressing OVA) was carried out.

Figure 11:
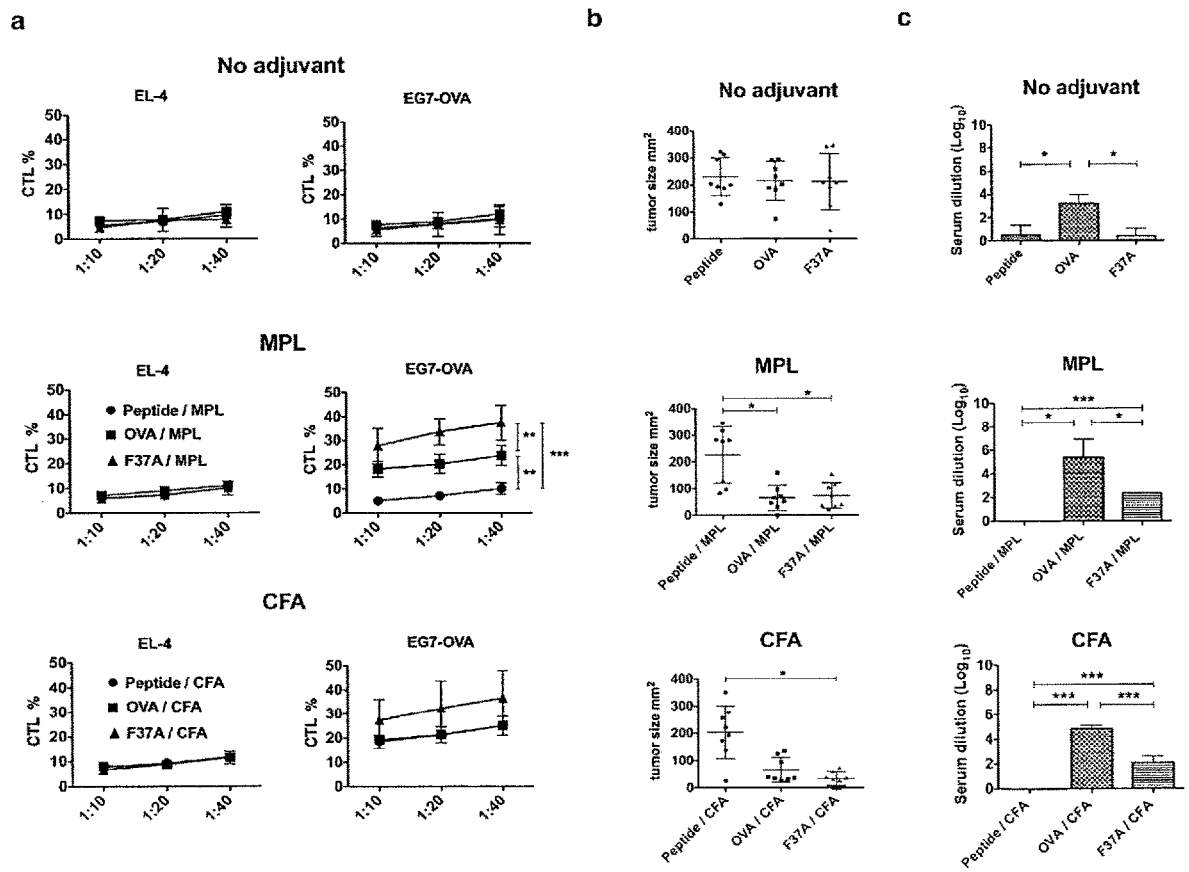
FIG. 11 shows the results of investigation of induction of antigen-specific CTLs in vivo in mice immunized with F37A. (a) Results of a cytotoxicity assay using spleen cells collected from the immunized mice. (b) Results of observation of tumor growth in mice which received the immunization and subsequent tumor cell transplantation. (c) Results of investigation of whether anti-OVA antibodies were produced in vivo in the immunized mice or not.

The results of the cytotoxicity assay are shown in FIG. 11a. Without use of an adjuvant, OVA-specific cytotoxic T cells, CTLs, were not detected in any of the groups immunized with the OVA-I peptide, native OVA protein, or F37A (FIG. 11a, top row).

In the cases where an antigen was administered together with an adjuvant MPL, the F37A group showed significantly stronger CTL induction compared to the OVA-I peptide group and the OVA group (FIG. 11a, middle row). Thus, it could be confirmed that F37A is capable of inducing cell-mediated immunity even without use of Freund's oil adjuvant.

In the cases where CFA was used as the adjuvant, the OVA-I peptide group and the OVA group also showed CTL induction. The CTL induction capacity of the F37A group tended to be higher than those of the OVA-I peptide group and the OVA group (FIG. 11a, bottom row).

These results indicate that F37A can more strongly induce CTLs than native OVA protein also in vivo.

8. Tumor Growth Suppression Effect of F37A

Subsequently, the tumor suppression effect on an OVA-expressing tumor was studied. Mice were immunized in the same manner as described above, and EG7-OVA tumor cells ($2 \times 10^6$ cells) were subcutaneously administered to the back of each mouse. Thereafter, the tumor diameter was measured every week. As a result, no difference in the tumor diameter were found among the groups without use of an adjuvant, at Week 3 after the inoculation of the tumor cells. However, in the cases where MPL was used as an adjuvant, the OVA immunization group and the F37A immunization group showed a significant tumor growth suppression effect (FIG. 11b). Thus, it could be confirmed that F37A is capable of inducing cell-mediated immunity even without use of Freund's oil adjuvant, and that the induced cell-mediated immunity is functional.

Among the groups in which the CFA adjuvant was used, the F37A immunization group showed significant suppression of the tumor growth.

These results indicate that CTLs induced by immunization with F37A are functional CTLs that can attack OVA-expressing tumor cells.

9. F37A Exhibits not Only Capacity to Induce Cell-Mediated Immunity, but Also Induction of Humoral Immunity Serum was collected from immunized mice, and whether or not anti-OVA antibodies were produced was investigated by the ELISA method using OVA as an antigen (FIG. 11c).

The group immunized with the OVA-I peptide did not show production of anti-OVA antibodies irrespective of whether an adjuvant was used or not.

On the other hand, the F37A immunization group showed production of anti-OVA antibodies by use of the adjuvant MPL or CFA. However, the amount of the antibodies produced was obviously lower than that in the OVA protein immunization group.

From the results on the CTL induction capacity and the antibody productivity, it was found that, although native OVA protein has a capacity to induce both cell-mediated immunity and humoral immunity, it is more likely to induce humoral immunity.

On the other hand, it was found that, although F37A has a capacity to induce both cell-mediated immunity and humoral immunity, it is more likely to induce cell-mediated immunity rather than humoral immunity.

Figure 12:
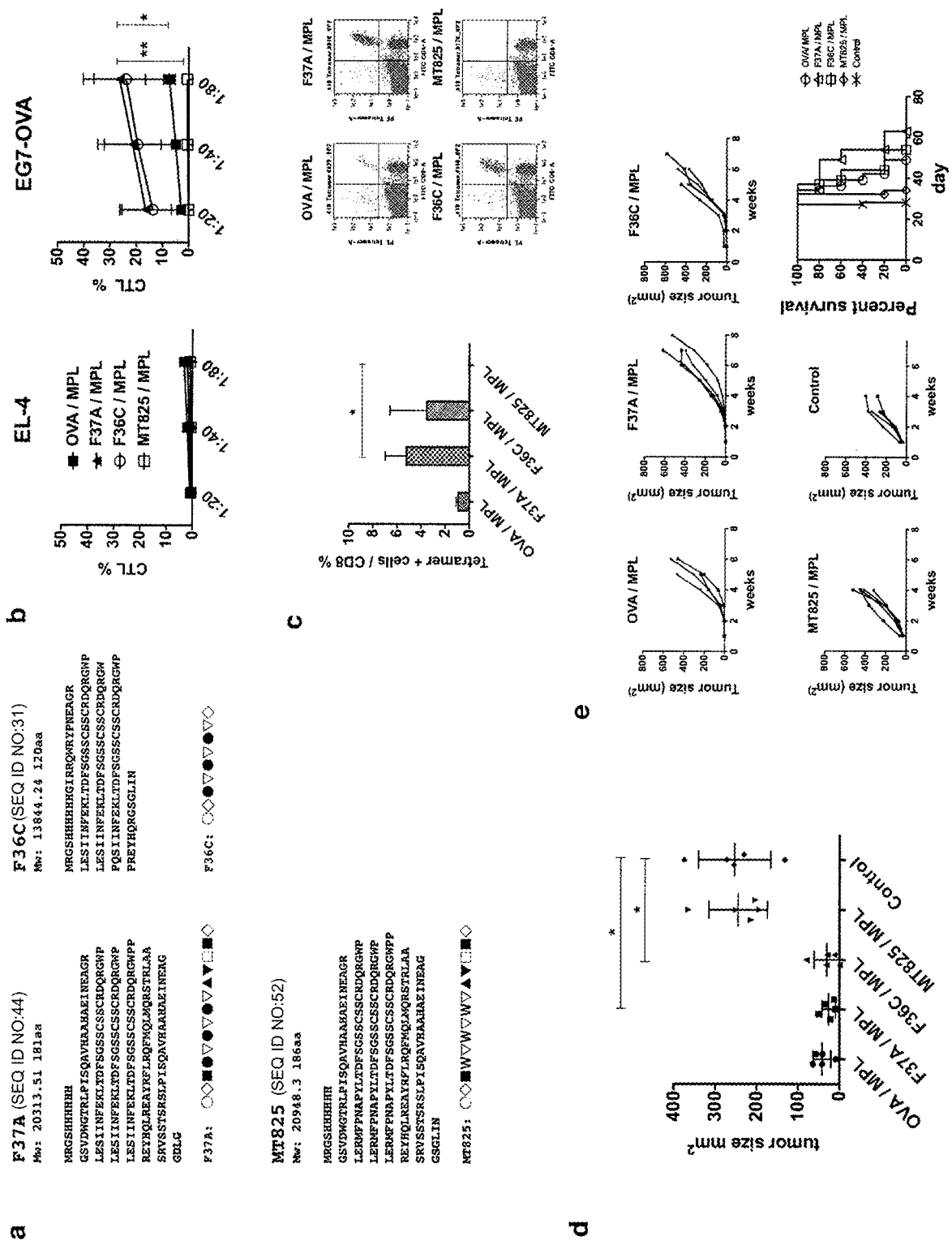
FIG. 12 shows the results of a study on involvement of class I epitopes and class II epitopes in the antigenicity of F37A. (a) The amino acid sequences of F37A, F36C, and MT825. (b) Results of investigation of the CTL activity by a $^{51}$Cr release assay in mice immunized together with the MPL adjuvant. (c) Results of a tetramer assay. (d) Results of observation of tumor growth in mice which received the immunization and subsequent tumor cell transplantation. (e) Graphs showing tumor growth in each individual of the immunized mice to which tumor cells were transplanted.

10. MHC Class II Epitope in F37A is not Indispensable for OVA-Specific CTL Induction, and MHC Class I Epitope Functions for Induction of Cell-Mediated Immunity In order to investigate whether the MHC class II epitope sequence OVA-II is involved in the OVA-specific CTL induction by F37A, mice were immunized with F36C artificial protein, which had no MHC class II epitope. In addition, in order to clarify that the MHC class I epitope sequence OVA-I present in F37A functions for induction of cell-mediated immunity, mice were immunized with MT825 artificial protein, in which all three OVA-I sequences were replaced with WT1 MHC class I epitopes. In the immunization, 100 µg of an antigen was intraperitoneally administered together with the adjuvant MPL (20 µg/mouse) three times at two-week intervals (FIG. 12a).

11. F36C, which has Same Characteristic Sequence Pattern (●∇●∇●∇) as that of F37A but does not have MHC Class II Epitope Sequence, can Induce CTLs As a result of a CTL assay of the immunized mice, the F37A immunization group showed a significantly higher level of induction of CTLs compared to the MT825 immunization group and the OVA immunization group (FIG. 12b). F36C, which had the same characteristic sequence pattern (●∇●∇●∇) as that of F37A but did not have the MHC class II epitope sequence, also showed a tendency to induce CTLs. MT825, which had no OVA-I, did not induce CTLs at all. From these results, it was suggested that induction of OVA-specific CTLs does not necessarily require the MHC class II epitope sequence.

12. OVA-I Sequence Functions for OVA-Specific CTL Induction by F37A

Since MT825 showed no CTL induction capacity, it was found that the OVA-I (OVA MHC class I epitope, SIINFEKL) sequence in F37A is indispensable for the OVA-specific CTL induction.

13. F37A Strongly Induces OVA-Specific CTLs (Tetramer Assay)

The presence of OVA-I peptide (SIINFEKL)-specific CD8-positive T cells in the immunized mice was confirmed by an assay using a tetramer reagent specific to the OVA-I sequence. The tetramer reagent is a tetramer containing the epitope peptide OVA-I bound to an MHC class I molecule, and cells expressing OVA-I-specific T cell receptors (TCRs) of T cells can be quantified with the reagent.

The results of the tetramer assay are shown in FIG. 12c. F37A showed a significantly higher level of induction of tetramer-positive cells compared to the MT825 immunization group. OVA and F36C also showed a tendency to induce the tetramer.

From these results, it was suggested that the CTLs which attack the OVA tumor cells described above are tetramer-positive CD8 cells specific to the OVA-I sequence of F37A.

14. F37A and F36C have Capacity to Suppress Tumor Growth

To mice immunized in the same manner as described above, EG7-OVA cells ($2\times10^6$ cells) were inoculated, and the tumor diameter was measured. At Week 3 after the tumor inoculation, the F37A and F36C immunization groups showed significant suppression of the tumor growth (FIG. 12d). FIG. 12e shows the tumor growth in each mouse. The OVA immunization group also showed a tendency to suppress the tumor growth.

As a result of comparison of the survival curve among the mice, prolonged survival was found in the OVA immunization group, F37A immunization group, and F36C immunization group. Among these, F37A showed the strongest effect of prolonging the survival (FIG. 12e, right end in the bottom row).

From these results, it was revealed that F37A can suppress the tumor growth more strongly than native OVA protein.

Although the tumor growth suppression was also found in F36C, which had no MHC class II sequence, a stronger tumor suppression capacity was found in F37A, which had MHC class II sequences. It was therefore suggested that, while an MHC class II sequence is not necessarily required in the induction phase (induction of CTLs), an antigen having both MHC class I and MHC class II sequences exhibits a stronger effect in the effector phase (when the immunity functions to attack the tumor).

F37A, which had a structure in which a sequence composed of an MHC class I sequence and a spacer sequence defined by CyberGene which were linked to each other was tandemly repeated three times and an MHC class II epitope was present at both of the N-terminus and the C-terminus, most strongly induced cell-mediated immunity both in vitro and in vivo and suppressed the tumor growth. Thus, it is thought that F37A provide us with a characteristic structure that functions as an antigen for vaccines which strongly induce cell-mediated immunity.

15. Analysis of Mechanism of Antigen Presentation Caused by F37A

At present, little is known about the intracellular pathway of cross-presentation, in which a foreign antigen is incorporated into antigen-presenting cells and an antigen epitope is presented on MHC class I molecules. The mechanism of antigen presentation caused by F37A, which is capable of inducing strong cell-mediated immunity through cross-presentation, was investigated.

F37A (SEQ ID NO:44), which shows the antigen-presenting capacity, comprises three MHC class I epitopes and two class II epitopes, and comprises a tandem repeat structure in which the class I epitope and the spacer sequence are linked to each other alternately and repeatedly three times. On the other hand, C131B (SEQ ID NO:64) comprises three MHC class I epitopes and three class II epitopes, but its molecular context (e.g. combination of the order of epitope sequences) is different from that of F37A. C131B does not comprise the tandem repeat structure described above, and shows no antigen-presenting capacity (FIG. 13A).

Figure 13:
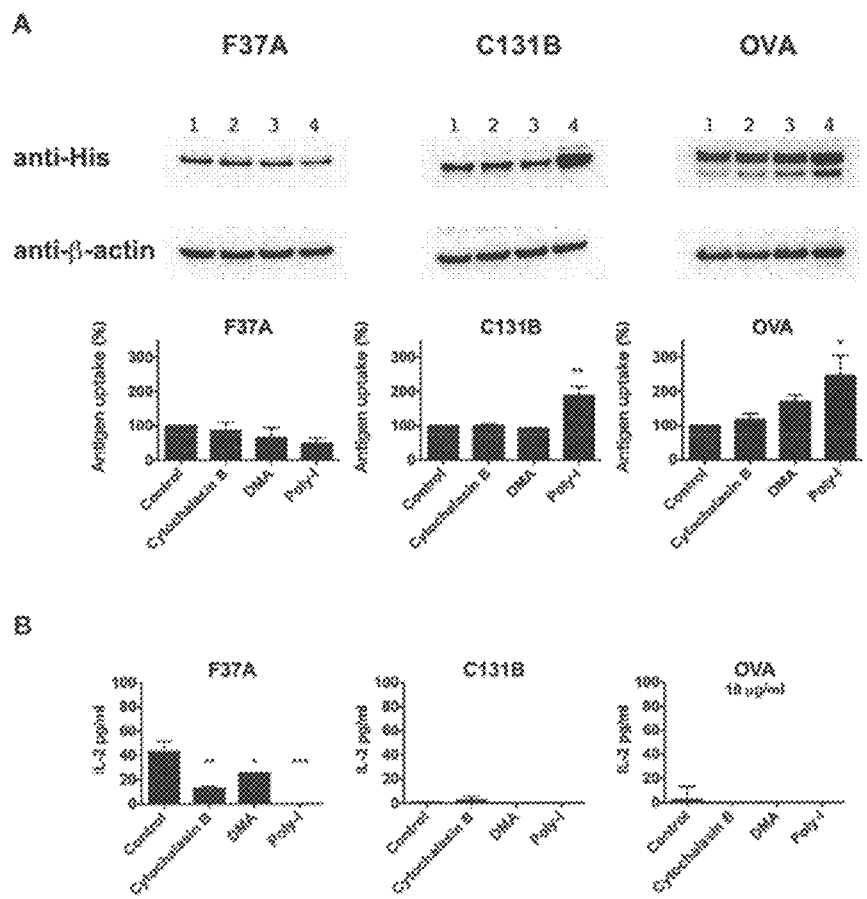
FIG. 13 shows a schematic diagram showing the structures of F37A and C131B. (A) DC2.4 cells, which are antigen-presenting cells, were treated with no inhibitor, or with cytochalasin B (phagocytosis inhibitor), DMA (pinocytosis inhibitor), or Poly-I (scavenger receptor A inhibitor). Thereafter, an antigen (F37A, C131B, or OVA) was added to the cells, and the cells were then cultured. The cultured cells were provided as samples for Western blotting using an anti-His-tag antibody and an anti-OVA antibody to measure the level of antigen incorporation into the antigen-presenting cells (lane 1, untreated control; lane 2, treatment with cytochalasin B; lane 3, treatment with DMA; lane 4, treatment with Poly-I). The band intensity for each antigen incorporated into the cells was measured by densitometry, and quantified using β-actin as a reference. The quantified values were represented as graphs. (B) DC2.4 cells, which are antigen-presenting cells, were treated with no inhibitor, or with cytochalasin B, DMA, or Poly-I. Thereafter, an antigen (F37A, C131B, or OVA) was added to the cells, and the cells were then cultured. Subsequently, OVA-specific T cell hybridoma cells (RF33.70 cells) were added to the culture to perform co-culture. By measuring the amount of IL-2 produced into the culture supernatant, the OVA-specific antigen-presenting capacity was evaluated.
Figure 14:
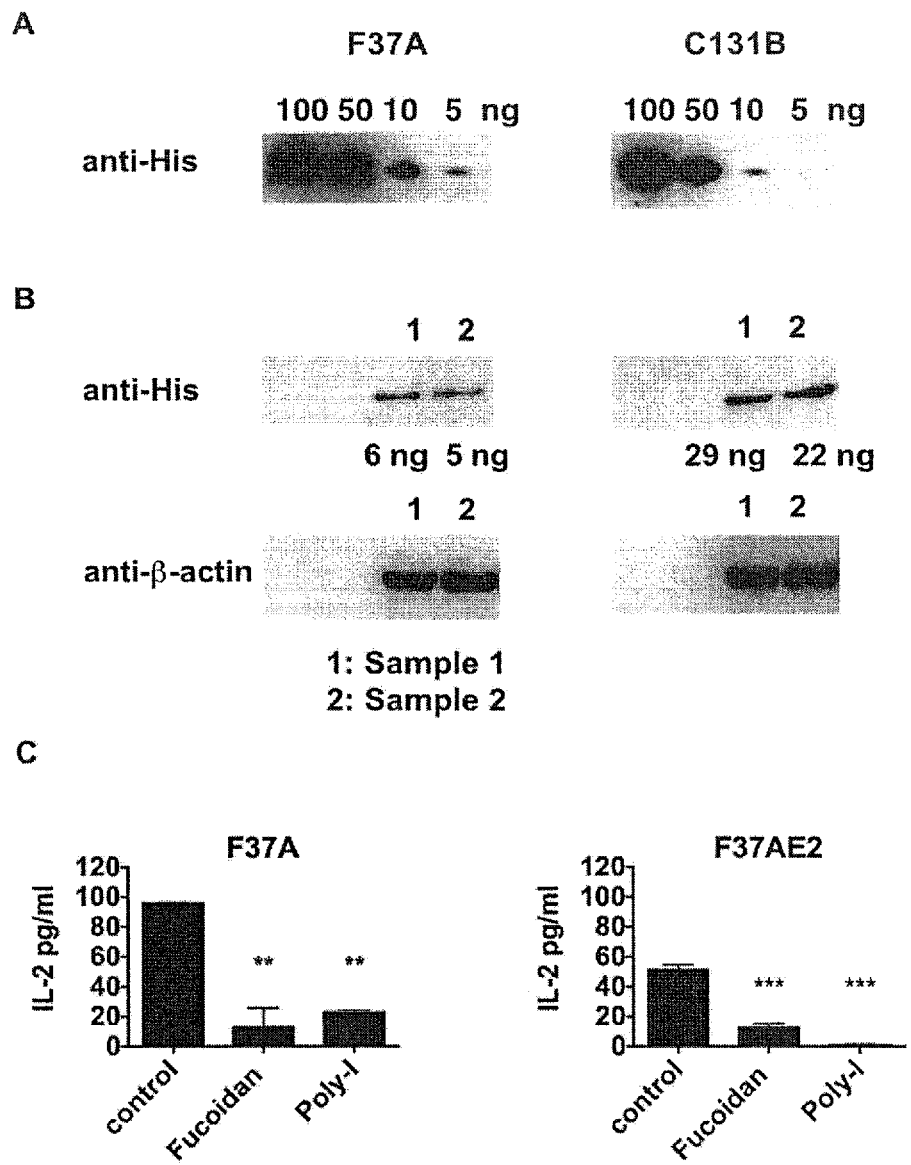
FIG. 14 (A) Results obtained by subjecting known amounts (100 ng, 50 ng, 10 ng, and 5 ng) of each of the F37A antigen and the C131B antigen to electrophoresis, carrying out WB (Western blotting) using an anti-His-tag antibody, and then detecting the antigens by autoradiography. The band intensities were measured by densitometry, and calibration curves were prepared based on the antigen concentrations and the band intensities (diagrams showing the calibration curves are not shown). (B) An antigen (F37A or C131B) was added to DC2.4 cells, which are antigen-presenting cells, and the cells were then cultured. By Western blotting using an anti-His-tag antibody and an anti-OVA antibody, the level of antigen incorporation into the antigen-presenting cells was measured. Based on the calibration curves obtained in A, the levels of F37A and C131B antigen incorporations into the antigen-presenting cells were semi-quantified. Two samples were subjected to the incorporation experiment for each of F37A and C131B. The amounts of F37A incorporated were 6 ng and 5 ng. The amounts of C131B incorporated were 29 ng and 22 ng.

First, the uptake of F37A and C131B by antigen-presenting cells was investigated. As a result, the uptake of F37A by antigen-presenting cells was found to be lower than the uptake of C131B (FIG. 14A, 14B). The uptake of C131B tended to be larger than the uptake of F37A. However, as shown in FIG. 13, C131B did not show antigen-presenting capacity at all. Thus, it was suggested that the uptake of F37A by antigen-presenting cells has no influence on the antigen-presenting function of F37A.

Subsequently, the fact that the mode of uptake of F37A by antigen-presenting cells is associated with the enhancement of the antigen-presenting capacity was investigated.

Examples of the mode of antigen uptake in cross-presentation that have been reported so far include macropinocytosis, non-specific phagocytosis, and receptor-mediated phagocytosis. Native antigen OVA is uptaken through mannose receptors of antigen-presenting cells (Burgdorf S, Kautz A, Bohnert V, Knolle P A, Kurts C (2007) Distinct pathways of antigen uptake and intracellular routing in CD4 and CD8 T cell activation. Science 316: 612-616.).

Since F37A was prepared using *E. coli*, it is not glycosylated. Therefore, it is thought that, unlike native antigen OVA, F37A is uptaken by antigen-presenting cells by a mechanism other than the pathway through the mannose receptor.

Antigen presenting cells (DC2.4 cells) were preliminarily treated with cytochalasin B (phagocytosis inhibitor), 5-(N, N-dimethyl)amiloride (DMA, pinocytosis inhibitor), or Poly-I (class A scavenger receptor (SRA) inhibitor), and an antigen (F37A, C131B, or OVA) was then added to the treated cells as well as untreated cells. Thereafter, the cells were cultured, and evaluated for the uptake of the antigen and for the antigen-presenting capacities in vitro.

As a result, the uptake of F37A by the antigen-presenting cells tended to be suppressed by Poly-I. On the other hand, the uptake of C131B and OVA was enhanced relative to poly-I (FIG. 13A), although the mechanism of this phenomenon is unclear. The antigen-presenting capacity of F37A was suppressed by cytochalasin B, DMA, and Poly-I. In particular, Poly-I strongly suppressed the antigen presentation (FIG. 13B). In the cases of the F37AE2 antigen (SEQ ID NO:45), which had the same amino acid sequence as F37A except for the 5 amino acids in the C-terminus, antigen presentation was suppressed by an SRA inhibitor fucoidan (FIG. 14C).

SRA is a cell membrane receptor expressed in macrophages, dendritic cells and the like, and responsible for uptake and processing of oxidized LDL and the like. It is also known that a protein composed of HSP (heat shock protein) bound to an antigen is uptaken by antigen-presenting cells through SRA, and induces cell-mediated immunity through cross-presentation (Murshid A, Gong J, Calderwood S K (2012) The role of heat shock proteins in antigen cross presentation. Front Immunol 3: 63.). Taking these facts into account, it was suggested that the uptake of F37A by antigen-presenting cells through SRA, which is due to the difference in the molecular context between F37A and C131B, leads to exhibition of the strong antigen-presenting capacity of F37A.

The invention claimed is:

1. A composition comprising as an effective component a polypeptide having the amino acid sequence selected from the amino acid sequences shown in SEQ ID NOs:54-63.

2. The composition of claim 1, which further comprising an adjuvant that activates the Toll-like receptor pathway.

3. The composition of claim 1, wherein said polypeptide has the amino acid sequence shown in SEQ ID NO: 54.

4. The composition of claim 1, wherein said polypeptide has the amino acid sequence shown in SEQ ID NO: 55.

5. The composition of claim 1, wherein said polypeptide has the amino acid sequence shown in SEQ ID NO: 56.

6. The composition of claim 1, wherein said polypeptide has the amino acid sequence shown in SEQ ID NO: 57.

7. The composition of claim 1, wherein said polypeptide has the amino acid sequence shown in SEQ ID NO: 58.

8. The composition of claim 1, wherein said polypeptide has the amino acid sequence shown in SEQ ID NO: 59.

9. The composition of claim 1, wherein said polypeptide has the amino acid sequence shown in SEQ ID NO: 60.

10. The composition of claim 1, wherein said polypeptide has the amino acid sequence shown in SEQ ID NO: 61.

11. The composition of claim 1, wherein said polypeptide has the amino acid sequence shown in SEQ ID NO: 62.

12. The composition of claim 1, wherein said polypeptide has the amino acid sequence shown in SEQ ID NO: 63.

* * * * *